(12) United States Patent
Boukharov et al.

(10) Patent No.: US 9,988,642 B2
(45) Date of Patent: Jun. 5, 2018

(54) IDENTIFICATION AND USE OF TARGET GENES FOR CONTROL OF PLANT PARASITIC NEMATODES

(71) Applicant: Monsanto Technology LLC, St. Louis, MO (US)

(72) Inventors: Andrey A. Boukharov, Chesterfield, MO (US); Zijin Du, Chesterfield, MO (US); Liang Guo, Cary, NC (US); Michelle C. Hresko, Chesterfield, MO (US); David K. Kovalic, Clayton, MO (US); Zhaolong Li, St. Louis, MO (US); Maolong Lu, St. Louis, MO (US); James P. McCarter, St. Louis, MO (US); Nancy M. Miller, Fenton, MO (US); Mark Vaudin, Comberton (GB); Deryck J. Williams, University City, MO (US); Wei Wu, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days. days.

(21) Appl. No.: 14/714,068

(22) Filed: May 15, 2015

(65) Prior Publication Data
US 2015/0252366 A1 Sep. 10, 2015

Related U.S. Application Data

(60) Continuation of application No. 14/011,647, filed on Aug. 27, 2013, now Pat. No. 9,388,409, which is a division of application No. 11/673,351, filed on Feb. 9, 2007, now Pat. No. 8,519,225, application No. 14/714,068, filed on May 15, 2015, which is a continuation-in-part of application No. 13/374,480, filed on Dec. 29, 2011, now abandoned, which is a continuation of application No. 11/360,355, filed on Feb. 23, 2006, now Pat. No. 8,088,976.

(60) Provisional application No. 60/772,265, filed on Feb. 10, 2006, provisional application No. 60/655,875, filed on Feb. 24, 2005.

(51) Int. Cl.
| | |
|---|---|
| C12N 15/82 | (2006.01) |
| C07K 14/435 | (2006.01) |
| A61K 31/713 | (2006.01) |
| C12N 15/113 | (2010.01) |
| A23L 33/105 | (2016.01) |
| A01N 57/16 | (2006.01) |
| C12Q 1/68 | (2018.01) |

(52) U.S. Cl.
CPC ......... *C12N 15/8285* (2013.01); *A01N 57/16* (2013.01); *A23L 33/105* (2016.08); *A61K 31/713* (2013.01); *C07K 14/435* (2013.01); *C07K 14/4354* (2013.01); *C12N 15/113* (2013.01); *C12N 15/1137* (2013.01); *C12N 15/8261* (2013.01); *C12N 15/8273* (2013.01); *C12Q 1/6888* (2013.01); *A23V 2002/00* (2013.01); *C12N 2310/11* (2013.01); *Y02A 40/164* (2018.01)

(58) Field of Classification Search
CPC .................................................. C12N 15/8285
USPC ......................................................... 800/279
See application file for complete search history.

(56) References Cited

U.S. PATENT DOCUMENTS

| | | | |
|---|---|---|---|
| 6,506,559 | B1 | 1/2003 | Fire et al. |
| 7,576,261 | B2 | 8/2009 | Hussey et al. |
| 7,622,301 | B2 | 11/2009 | Ren et al. |
| 7,659,444 | B2 | 2/2010 | Ren et al. |
| 7,803,984 | B2 | 9/2010 | Trick et al. |
| 8,067,671 | B2 | 11/2011 | Boukharov et al. |
| 2003/0061626 | A1 | 3/2003 | Plaetinck et al. |
| 2003/0150017 | A1 | 8/2003 | Mesa et al. |
| 2004/0098761 | A1 | 5/2004 | Trick et al. |
| 2004/0133943 | A1 | 7/2004 | Plaetinck et al. |
| 2005/0188438 | A1 | 8/2005 | Ren et al. |
| 2006/0037101 | A1 | 2/2006 | Ren et al. |
| 2007/0271630 | A1 | 11/2007 | Boukharov et al. |
| 2009/0093620 | A1 | 4/2009 | Kovalic |
| 2009/0188005 | A1 | 7/2009 | Boukharov et al. |

(Continued)

FOREIGN PATENT DOCUMENTS

| | | |
|---|---|---|
| WO | WO 01/37654 | 5/2001 |
| WO | WO 03/052110 | 6/2003 |

(Continued)

OTHER PUBLICATIONS

Yibrah et al. 1993, Hereditas 118:273-2890.*

(Continued)

*Primary Examiner* — Li Zheng
(74) *Attorney, Agent, or Firm* — Dentons US LLP; Amanda Carmany-Rampey

(57) ABSTRACT

The invention relates to identifying and evaluating target coding sequences for control of plant parasitic nematodes by inhibiting one or more biological functions, and their use. The invention provides methods and compositions for identification of such sequences and for the control of a plant-parasitic nematode population. By feeding one or more recombinant double stranded RNA molecules provided by the invention to the nematode, a reduction in disease may be obtained through suppression of nematode gene expression. The invention is also directed to methods for making transgenic plants that express the double stranded RNA molecules, and the plant cells and plants obtained thereby.

16 Claims, 6 Drawing Sheets

(56) References Cited

U.S. PATENT DOCUMENTS

2014/0325702 A1 10/2014 Boukharov et al.
2016/0376606 A1 12/2016 Boukharov et al.

FOREIGN PATENT DOCUMENTS

WO WO 2005/019408 3/2005
WO WO 2007/095469 8/2007

OTHER PUBLICATIONS

Thomas et al. 2001, The Plant Journal 25(4):417-425.*
Gao et al. Mol. Plant Microbe Interact. 14 (10), 1247-1254 (2001).*
U.S. Appl. No. 12/101,830, filed Apr. 11, 2008, Boukharov et al.
U.S. Appl. No. 60/395,153, filed Jul. 10, 2002, Trick et al.
Aboobaker et al., "Medical significance of caenorhabditis elegans," *Annals of Medicine*, 32:23-30, 2000.
Aboobaker et al., "Use of RNA interference to investigate gene function in the human filarial nematode parasite brugio malayi," *Mol. Biochem. Parasitol.*, 129:41-51, 2003.
Ashrafi et al., "Genome-wide RNAi analysis of caenorhabditis elegans fat regulatory genes," *Nature*, 421:268-272, 2003.
Bargmann, "Neurobiology of the caenorhabditis elegans genome," *Science*, 282:2028-2033, 1998.
Barker et al., "Plant and soil nematodes: societal impact and focus for the future," The Committee on National Needs and Priorities in Nematology, Cooperative State Research Service, U.S. Department of Agriculture and Society of Nematologists, 1994.
Burglin et al., "Caenorhabditis elegans as a model for parasitic nematodes," *Intl. J. for Parasitology*, 28:395-411, 1998.
Davis et al., "Nematode parasitism genes," *Annu. Rev. Phytopathol.*, 38:365-396, 2000.
Dong et al., "Genetic analysis of parasitism in the soybean cyst nematode heterodera glycines," *Genetics*, 146:1311-1318, 1997.
Elbashir et al., "RNA interference is mediated by 21- and 22-nucleotide RNAs," *Genes Dev.*, 5(2):188-200, 2001.
EST Accession No. CB278684, dated Feb. 26, 2003.
EST Accession No. CB281513, dated Feb. 27, 2003.
EST Accession No. CB374668, dated Mar. 18, 2003.
EST Accession No. CB375671, dated Mar. 18, 2003.
Fairbairn et al., "Plant delivered RNAi (PD-RNAi): a novel strategy to control plant parasitic nematodes by inactivating nematode genes in planta," (Annual Meeting Abstract #372), American Society for Plant Biology, 2005.
Fire et al. "Potent and specific genetic interference by double-stranded RNA in caenorhabditis elegans," *Nature*, 391:806-811, 1998.
Foster et al., "Wolbachia genome of brugia malayi: endosymbiont evolution within a human pathogenic nematode," *PLOIS Biol.*, 3(4):599-614, 2005.
Fraser et al., "Functional genomic analysis of C. elegans chromosome I by systematic RNA interference," *Nature*, 408:325-330, 2000.
Geary et al., "Caenorhabditis elegans: how good a model for veterinary parasites," *Veterinary Parasitology*, 101:371-386, 2001.
GenBank Accession No. CB351902, dated Dec. 22, 2003.
GenBank Accession No. CB351909, dated Dec. 22, 2003.
GenBank Accession No. CB374546, dated Mar. 13, 2008.
GenBank Accession No. CB376018, dated Mar. 18, 2003.
GenBank Accession No. CB825016, dated Apr. 16, 2003.
Gonczy et al., "Functional genomic analysis of cell division in C. elegans using RNAi of genes on chromosome III," *Nature*, 408(16):331-336, 2000.
Hamilton et al., "A species of small antisense RNA in post-transcriptional gene silencing in plants," *Science*, 286:950-952, 1999.
Hamilton et al., "Two classes of short interfering RNA in RNA silencing," *The EMBO J.*, 21(17):4671-4679, 2002.
Harris et al., "Wormbase: a multi-species resource for nematode biology and genomics," *Nucleic Acids Research*, 32:D411-D417, 2004.
Hussein et al., "Suppression of secreted acetylcholinesterase expression in nippostrongylus brasiliensis by RNA interference," *Mol. Biochem. Parasitol.*, 122:91-94, 2002.
Imhof et al., "Fitness effects of advantageous mutations in evolving *Escherichia coli* populations," *Proc. Natl Acad. Sci. USA*, 98:1113-1117, 2001.
Kamath et al., "Effectiveness of specific RNA-mediated interference through ingested double-stranded RNA in caenorhabditis elegans," *Genome Biol.* 2(1):Research 0002.1-0002-10, 2001.
Kamath et al., "Systematic functional analysis of the caenorhabditis elegans genome using RNAi," *Nature*, 421:231-237, 2003.
Kwa et al., "Beta-tubulin genes from the parasitic nematode haemonchus contortus modulate drug resistance in caenorhabditis elegans," *J. Mol. Biol.*, 246:500-510, 1995.
Lee et al., "Regulation of gene expression, cellular localization, and in vivo function of caenorhabditis elegans DNA topoisomerase I," *Genes to Cells*, 6:303-312, 2001.
Lustigman et al., "RNA interference targeting cathepsin L and Z-like cysteine proteases of onchocerca volvulus confirming their essential function during L3 molting," *Mol. Biochem. Parasitol.*, 138:165-170, 2004.
Maeda et al., "Large-scale analysis of gene function in caenorhabditis elegans by high-throughput RNAi," *Curr. Biol.*, 11(3):171-176, 2001.
Martin, "Modes of action of anthelmintic drugs," *Vet J.*, 154:11-34, 1997.
Martinez et al., "Single-stranded antisense siRNAs guide target RNA cleavage in RNAi," *Cell*, 110:563-574, 2002.
McCarter et al., "Analysis and functional classification of transcripts from the nematode meloidogyne incognita," *Genome Biology*, 4:R26.1-R26.19, 2003.
McCarter et al., "Nematode gene sequences: update for Dec. 2003," *J. of Nematology*, 35(4):465-469, 2003.
McCarter, "Genomic filtering: an approach to discovering novel antiparasitics," *Trends in Parasitology*, 20(10):462-468, 2004.
McManus et al., "Gene silencing in mammals by small interfering RNAs," *Nature Reviews*, 3:737-747, 2002.
Mitreva et al., "A survey of SL1-spliced transcripts from the root-lesion nematode pratylenchus penetrans," *Mol. Gen. Genomics*, 272:138-148, 2004.
Mitreva et al., "Comparative genomics of gene expression in the parasitic and free-living nematodes strongyloides stercoralis and caenorhabditis elegans," *Genome Research*, 14:209-220, 2004.
Montgomery et al., "RNA as a target of double-stranded RNA-mediated genetic interference in caenorhabditis elegans," *Proc. Natl. Acad. Sci. USA*, 95:15502-15507, 1998.
Nucleotide Sequence Alignment between SEQ ID No. 1289 and GenBank Accession No. CB351902, dated Dec. 22, 2003.
Nucleotide Sequence Alignment between SEQ ID No. 1289 and GenBank Accession No. CB351909, dated Dec. 22, 2003.
Nucleotide Sequence Alignment between SEQ ID No. 1289 and GenBank Accession No. CB376018, dated Mar. 18, 2003.
Nucleotide Sequence Alignment between SEQ ID No. 1289 and GenBank Accession No. CB825016, dated Apr. 16, 2003.
Nucleotide Sequence Alignment between SEQ ID No. 1513 and GenBank Accession No. CB351902, dated Dec. 22, 2003.
Nucleotide Sequence Alignment between SEQ ID No. 1513 and GenBank Accession No. CB351909, dated Dec. 22, 2003.
Nucleotide Sequence Alignment between SEQ ID No. 1513 and GenBank Accession No. CB376018, dated Mar. 18, 2003.
Nucleotide Sequence Alignment between SEQ ID No. 1513 and GenBank Accession No. CB825016, dated Apr. 16, 2003.
Omura et al., "An anthelmintic compound, nafuredin, shows selective inhibition of complex I in helminth mitochondria," *Proc. Natl. Acad. Sci. USA*, 98:60-62, 2001.
Papp et al., "Dosage sensitivity and the evolution of gene families in yeast," *Nature*, 424:194-197, 2003.
Papp et al., "Metabolic network analysis of the causes and evolution of enzyme dispensability in yeast," *Nature*, 429:661-664, 2004.

(56) References Cited

OTHER PUBLICATIONS

Parkinson et al., "A transcriptomic analysis of the phylum nematoda," *Nature Genetics*, 36:1259-1267, 2004.
Piano et al., "Gene clustering based on RNAi phenotypes of ovary-enriched genes in C. elegans," *Curr. Biol.*, 12:1959-1964, 2002.
Piano et al., "RNAi analysis of genes expressed in the ovary of caenorhabditis elegans," *Curr. Biol.*, 10:1619-1622, 2000.
Qiu et al., "A computational study of off-target effects of RNA interference," *Nucleic Acids Res.*, 33(6):1834-1847, 2005.
Redmond et al., "Expression of haemonchus contortus pepsinogen in caenorhabditis elegans," *Mol. Biochem. Parasitol.*, 112:125-131, 2001.
Ruvkun, "The taxonomy of developmental control in caenorhabditis elegans," *Science*, 282:2033-2041, 1998.
Scholl et al., "Horizontally transferred genes in plant parasitic nematodes: a high-throughput genomic approach," *Genome Biology*, 4:R39.1-R39.12, 2003.
Schwarz et al., "Asymmetry in the assembly of the RNAi enzyme complex," *Cell*, 115:199-208, 2003.
Silhavy et al., "A viral protein suppresses RNA silencing and binds silencing-generated, 21- to 25-nucleotide double-stranded," *The EMBO J.*, 21(12):3070-3080, 2002.
Simmer et al., "Genome-wide RNAi of C. elegans using the hypersensitive rrf-3 strain reveals novel gene functions," *PLOS Biol.*, 1(1):77-84, 2003.
Smith et al., "Total silencing by intron-spliced hairpin RNAs," *Nature*, 407:319-320, 2000.
Sonnichsen et al., "Full-genome RNAi profiling of early embryogenesis in caenorhabditis elegans," *Nature*, 434:462-469, 2005.
Thomas et al., "Size constraints for targeting post-transcriptional gene silencing and for RNA-directed methylation in nicotiana benthamiana using a potato virus X vector," *The Plant J.*, 25(4):417-425, 2001.
Urwin et al., "Ingestion of double-stranded RNA by preparasitic juvenile cyst nematodes leads to RNA interference," *Mol. Plant Microbe Interact.*, 15:747-752, 2002.
Winston et al., "Systemic RNAi in C. elegans requires the putative transmembrane protein SID-1," *Science*, 295:2456-2459, 2002.
Winzeler et al., "Functional characterization of the S. cerevisiae genome by gene deletion and parallel analysis," *Science*, 285:901-906, 1999.
Zheng et al., "Conservation and diversification of Wnt signaling function during the evolution of nematode vulva development," *Natl. Genet.*, 37:300-304, 2005.
Gao et al., "Identification of Putative Parasitism Genes Expressed in the Esophegeal Glad Cells of the Soybean Cyst Nematode *Heterodera glycines*," *Molecular Plant-Microbe Interactions*, 14(10):1247-1254, 2001.
USPTO: Non-Final Office Action regarding U.S. Appl. No. 14/011,647, dated Jul. 27, 2015.
Response to Non-Final Office Action regarding U.S. Appl. No. 14/011,647, dated Oct. 2, 2015.
Yamada et al., "Accelerated off-target search algorithm for siRNA," *Bioinformatics* 21(8):1316-1324, 2005.
Notice of Allowance and Fees Due regarding U.S. Appl. No. 14/011,647, dated Mar. 14, 2016.
Response to Final Office Action regarding U.S. Appl. No. 14/011,647, dated Feb. 24, 2016.
USPTO: Final Office Action regarding U.S. Appl. No. 14/011,647, dated Oct. 27, 2015.
U.S. Appl. No. 15/194,355, filed Jun. 27, 2016, Boukharov et al.
USPTO: Non-Final Office Action regarding U.S. Appl. No. 15/194,355, dated Apr. 11, 2018.

\* cited by examiner

FIG. 1

| Locus | Description | N2 egg start | N2 L4 start | Outcome |
|---|---|---|---|---|
| control | actin | mobile adults, sterile | P0-WT, few progeny | positive control |
| control | GFP | WT, >200 progeny<br>WT, >200 progeny | WT, >200 progeny<br>WT, >200 progeny | negative control |
| R03E1.2 | VAC1 | WT, 20e | P0-WT, few progeny | Phenotype, not Po lethal |
| Y57E12AL.a | | WT,75e | P0-WT, red. brood | Phenotype, not Po lethal |
| C34G6.6 | PAN1 | dead, 0e | mobile adult, LVL | Po Lethal From Egg Start |
| F52B11.3 | PAN2 | dead, 0e | mobile adult, LVL | Po Lethal From Egg Start |
| F54D11.1 | MT | P0-WT, LVA<br>P0-WT, LVA<br>P0-WT, LVA | P0-WT, LVA<br>P0-WT, LVA<br>P0-WT, LVA | Phenotype, not Po lethal |
| T25C8.2 | act-5 | P0 very sick, sterile<br>P0 sick, sterile or few F1s all LVA<br>dead, 0e | P0-WT, LVL-LVA<br>P0 sick, sterile or few F1s all LVA<br>P0 WT, F1 LVL/LVA | Po Lethal From Egg Start |
| Y57G11C.15 | Transport protein Sec61 | very sick, sterile<br>very sick, sterile, dead | mobile adult, sterile<br>RUP, dead | Po Lethal From Egg & L4 Start |
| C47E12.5 | uba-1 | dead, 0e<br>dead, 0e | P0-WT, LVL<br>P0 WT, F1 LVL | Po Lethal From Egg Start |
| Y41E3.1** | | WT<br>WT<br>30% reduced brood | WT<br>WT<br>WT | No Effect yet |
| Y57E12AL.6 | | bag-o-worms+larvae<br>P0 red brood, sick F1 LVA | mobile adult, F1 LVA<br>mobile adult, F1 LVA | In progress |
| C32E12.4 | | mobile adults, sterile<br>WT | WT<br>WT | In progress |
| Y48B6A.1* | | WT<br>WT<br>WT | WT<br>WT<br>WT | No Effect yet |
| Y48B6A.1* | | | | In Progress |
| R07E4.6* | kin-2 | Very DPY, sick, sterile<br>Very DPY, sterile, dead<br>Very DPY, sterile, dead | P0 DPY, red brood, F1 25% DPY<br>P0 DPY, red brood, F1 75% DPY<br>P0 DPY, red brood, F1 90% DPY | Po Lethal/Dpy From Egg & L4 Start |
| K11D9.2a | sca-1 | P0 WT, red. brood - F1 LVA<br>P0 sterile, gro, sick | P0 WT, red. brood - F1 LVA<br>P0 mobile, red eggs, F1 LVA | Po Sick From Egg Start? |
| ZK20.3** | | WT<br>WT | WT<br>WT | No Effect yet |
| K07B1.7** | | WT<br>WT | WT<br>WT | No Effect yet |
| C38D4.6 | | P0 WT, F1 LVL | P0 WT, F1 LVL | Phenotype, not Po lethal |
| T02E1.5** | dhs-3 | WT<br>WT | WT<br>WT | No Effect yet |
| F17E9.5*** | | WT | WT | In Progress |
| C25D7.2*** | | WT | WT | In Progress |
| K06B4.1 | | WT | WT | In Progress |
| F08B1.1a | | 85% reduced brood | WT | Phenotype, not Po lethal |
| C34F11.6 | | WT | WT | In Progress |
| T14G10.5 | | | | In Progress |
| F28D9.8 | | to be done | to be done | In Progress |
| W09G12.7 | | | | In Progress |
| C37C3.2 | | to be done | to be done | In Progress |

FIG. 2

| Rank SCN Targets v2.0, 4/15/05 | locus | gene name | Brief Identification | top % ID | top bit | min e-val | RNAi Phenotype Rank | LET LVL LVA | MLT BLI RUP | STE EMB | GRO SCK UNC PRL PRZ | WT | WT % of Weighted Reports | Divergence#PO RNAi Phenotype | Divergence Intestinal RNAi Phenotype | total H.g ESTs | J2, J3, J4 H.g ESTs | Total ESTs Other Species |
|---|---|---|---|---|---|---|---|---|---|---|---|---|---|---|---|---|---|---|
| 1 C02C6.1 | dyn-1 | dynamin | 75.32 | 339 | 1.00E-92 | 3 | 2.3 | 1 | 2.6 | 1.6 | 0 | 0.0% | | | 1 | 1 | 0 |
| 2 Y57G11C.15 | sec61 alph | protein transport protein | 95.04 | 499.2 | 3.00E-142 | >44 | 0 | 0 | 3 | 1 | 0 | 0.0% | PO leth: 80% Red | ND | ND | ND | |
| 3 C47E12.5 | uba-1 | ubiquitin-activating enz | 56.28 | 329 | 1.00E-124 | >44 | 0 | 0 | 4.7 | 2 | 0 | 0.0% | PO leth: 40-100% R | ND | ND | ND | |
| 4 R07E4.6 | kin-2 | regulatory subunit of a | 85.05 | 328.2 | 7.60E-91 | 34 | 2.2 | 0 | 0 | 1.6 | 0 | 0.0% | PO lethal, egg & L4 | | 1 | 0 | 0 |
| 5 ZK1151.1 | vab-10 | spectraplakins (VAB-10 | 58.85 | 547.7 | 9.00E-161 | 6 | 4 | 1.8 | 1.2 | 4 | 1 | 8.3% | | | 3 | 3 | 106 |
| 6 T14F9.1 | vha-15 | ATPase subunit | 61.68 | 213.4 | 3.50E-56 | 3 | 3 | 1 | 2.6 | 1 | 0.3 | 3.8% | | | 2 | 2 | 3 |
| 7 C34G6.6 | C34G6.6 | Zona pellucida-like dom | 57.58 | 217.6 | 2.40E-75 | 10 | 3.2 | 0 | 3.2 | 1 | 0 | 0.0% | Po lethal, egg start | | 1 | 1 | 1 |
| 8 Y48B6A.3 | Y48B6A.3 | XRN 5'-3' exonuclease | 73.27 | 482.3 | 8.00E-137 | 3 | 3.6 | 1 | 2.6 | 2 | 0 | 0.0% | | | 2 | 0 | 6 |
| 9 Y23H5A.7 | crs-1 | aminoacyl-tRNA synthe | 40.15 | 178.7 | 9.90E-66 | 6 | 2.2 | 1 | 1 | 1 | 0 | 0.0% | | | 1 | 0 | 0 |
| 10 F20B6.2 | vha-12 | vacuolar ATP synthase | 77.6 | 521 | 3.00E-150 | 10 | 2.3 | 0 | 2.6 | 2 | 0 | 0.0% | | | 5 | 3 | 1 |
| 11 K07D4.3 | rpn-11 | non-ATPase subunit of | 91.93 | 407.9 | 6.00E-115 | 10 | 2 | 0 | 2.6 | 1 | 0 | 0.0% | | | 1 | 0 | 0 |
| 12 F25H5.4 | eft-2 | Elongation factor Tu far | 85.47 | 1015.6 | 0.00E+00 | 39 | 1.2 | 0 | 2.8 | 0 | 0 | 0.0% | | | 8 | 4 | 0 |
| 13 C36B1.4 | pas-4 | proteasome A-type sub | 74.29 | 320.9 | 7.40E-89 | 10 | 2.3 | 0 | 2.8 | 1.6 | 0 | 0.0% | | | 1 | 1 | 32 |
| 14 F25H2.9 | pas-5 | proteasome zeta chain | 64.54 | 319.3 | 2.10E-88 | 10 | 2.9 | 0 | 2.8 | 1.6 | 0 | 0.0% | | | 0 | 0 | 11 |
| 15 F56C11.1 | bli-3 | large homolog of dual c | 68.6 | 129 | 1.50E-29 | 5 | 5.4 | 6.5 | 1 | 0.6 | 0 | 0.0% | | | 3 | 3 | 0 |
| 16 C07H6.5 | cgh-1 | ATP-dependent RNA h | 80.2 | 326.2 | 3.40E-90 | 25 | 1 | 1 | 7 | 0 | 0.3 | 3.2% | | | 2 | 1 | 0 |
| 17 F49D11.1 | F49D11.1 | WD domain, G-beta rep | 64.04 | 790.4 | 0.00E+00 | 26 | 1.2 | 0 | 3.2 | 1.6 | 0 | 0.0% | | | 1 | 0 | 0 |
| 18 C56G2.6 | let-767 | short-chain dehydroger | 52.17 | 294.3 | 9.90E-81 | 10 | 2.3 | 0 | 2 | 2.6 | 0 | 0.0% | | | 11 | 11 | 0 |
| 19 CD4.6 | pas-6 | protease | 58.18 | 271.6 | 5.40E-74 | 26 | 1.2 | 0 | 3.6 | 1.6 | 0 | 0.0% | | | 2 | 2 | 1 |
| 20 K01G5.4 | ran-1 | GTP-binding protein | 94.19 | 344 | 6.00E-107 | 10 | 2 | 0 | 5.6 | 2 | 0 | 0.0% | | | 0 | 0 | 49 |
| 21 T25C8.2 | act-5 | Actins | 92.51 | 713.8 | 0.00E+00 | >44 | 0 | 0 | 3.7 | 1 | 0 | 0.0% | PO leth: 70-90% Re | | 2 | 2 | 1034 |
| 22 C54G4.8 | cyc-1 | cytochrome C1, heme | 58.54 | 120.9 | 5.70E-28 | 10 | 2.2 | 0 | 3.2 | 1 | 0 | 0.0% | | 50-80% Re | 0 | 0 | 7 |
| 23 C52E4.4 | rpt-1 | 26S protease regulator | 75.23 | 679.5 | 0.00E+00 | 26 | 1 | 0 | 3.6 | 1 | 0 | 0.0% | | | 0 | 0 | 32 |
| 24 H06I04.4 | ubl-1 | ubiquitin | 51.46 | 167.9 | 4.20E-43 | 10 | 3.1 | 0 | 7.6 | 2 | 0 | 0.0% | | | 0 | 0 | 31 |
| 25 Y49A3A.2 | vha-13 | ATP synthase alpha an | 86.95 | 1006.1 | 0.00E+00 | 26 | 1 | 0 | 3.2 | 2 | 0 | 0.0% | | | 11 | 2 | 6 |
| 26 M01E5.5 | top-1 | DNA topoisomerase I | 72.57 | 333.6 | 4.20E-92 | 20 | 1.2 | 2 | 0 | 1.8 | 0.3 | 5.7% | | | 1 | 0 | 1 |
| 27 ZK1127.5 | ZK1127.5 | RNA 3'-terminal phosph | 54.62 | 406.8 | 2.00E-114 | 10 | 2.6 | 0 | 3.6 | 3 | 0 | 0.0% | | | 3 | 2 | 0 |
| 28 C26E6.4 | C26E6.4 | DNA-directed RNA poly | 82.78 | 627.5 | 0.00E+00 | 26 | 1 | 0 | 4.6 | 1 | 0 | 0.0% | | | 8 | 6 | 0 |
| 29 F43D9.3 | F43D9.3 | Sly1, vesicle trafficking | 57.79 | 218 | 2.00E-57 | 10 | 2 | 0 | 3 | 3 | 0 | 0.0% | | | 1 | 0 | 0 |
| 30 F52B11.3 | F52B11.3 | PAN domain;Zona pellu | 66.67 | 103.6 | 3.10E-22 | 15 | 2.3 | 0 | 1.6 | 1.6 | 0 | 0.0% | PO lethal, egg start | | 1 | 0 | 2 |
| 31 C30C11.4 | C30C11.4 | Msi3p | 49.09 | 221 | 3.00E-58 | 3 | 2 | 1.6 | 3 | 4.2 | 0 | 0.0% | | | 53 | 20 | 81 |
| 32 F01G10.1 | F01G10.1 | transketolase | 82.93 | 542.3 | 5.00E-155 | 26 | 1 | 0 | 2.7 | 2 | 0 | 0.0% | | | 5 | 5 | 88 |
| 33 C23H3.4 | C23H3.4 | aminotransferase | 56 | 111.3 | 6.00E-42 | 15 | 2.6 | 0 | 1.6 | 2.6 | 0 | 0.0% | 80% Red | | 1 | 1 | 0 |
| 34 K01C8.10 | cct-4 | T-complex protein | 74.59 | 623.2 | 2.00E-179 | 42 | 0.6 | 1 | 4.2 | 0 | 0 | 0.0% | | | 17 | 10 | 11 |
| 35 F54B3.3 | F54B3.3 | ATPases associated wi | 61.9 | 129 | 4.80E-47 | 10 | 2.6 | 0 | 3.6 | 1 | 0 | 0.0% | | | 0 | 0 | 0 |
| 36 T08B2.9 | frs-1 | phenylalanyl-tRNA synt | 68.91 | 425.2 | 9.00E-124 | 26 | 1.2 | 0 | 8.5 | 1 | 0 | 0.0% | | | 2 | 2 | 49 |
| 37 F53G12.3 | F53G12.3 | partial homolog of dual | 69.77 | 130.6 | 5.00E-30 | 9 | 3.4 | 3.8 | 0 | 0.6 | 0 | 0.0% | | | 3 | 3 | 1 |
| 38 C01H6.5 | nhr-23 | nuclear hormone recep | 83.58 | 121.7 | 1.20E-41 | 14 | 4.2 | 1 | 0 | 2.2 | 1 | 11.9% | | | 2 | 2 | 0 |
| 39 ZK792.6 | let-60 | LET-60 RAS protein | 77.17 | 294.3 | 4.70E-81 | 10 | 3.4 | 0 | 2 | 1.2 | 1 | 13.2% | | | 1 | 0 | 0 |
| 40 W02F12.5 | W02F12.5 | dihydrolipoamide succi | 67.5 | 156.4 | 2.30E-38 | 26 | 1.3 | 0 | 2.6 | 1 | 0 | 0.0% | | | 1 | 0 | 3 |
| 41 Y32F6A.3 | pap-1 | POLY(A) POLYMERAS | 60.44 | 404.4 | 2.00E-113 | 10 | 1.6 | 0 | 3.3 | 2 | 0 | 0.0% | | | 3 | 1 | 0 |
| 42 M28.5 | M28.5 | ribosomal protein (L7AI | 93.33 | 218.4 | 1.70E-58 | 10 | 2.6 | 0 | 2.6 | 1 | 0 | 0.0% | | | 2 | 2 | 64 |
| 43 Y105E8A.9 | apt-1 | gamma subunit of adap | 74.11 | 342.8 | 2.00E-105 | 10 | 2.2 | 0 | 3.2 | 2 | 0 | 0.0% | | | 1 | 0 | 4 |
| 44 C54D1.5 | C54D1.5 | Laminin EGF-like (Dom | 62.22 | 213 | 2.00E-149 | 26 | 1.6 | 0 | 3.6 | 1 | 0 | 0.0% | | | 3 | 3 | 16 |
| 45 T20H4.3 | prs-1 | Prolyl-tRNA synthetase | 73.26 | 300.4 | 2.00E-106 | 10 | 3.3 | 0 | 4.6 | 2 | 0 | 0.0% | | | 2 | 0 | 1 |
| 46 F40F8.10 | rps-9 | ribosomal protein S9 | 79.57 | 297.4 | 5.80E-82 | 10 | 2.3 | 0 | 4.2 | 1 | 0 | 0.0% | | | 1 | 0 | 4 |
| 47 K04G7.4 | K04G7.4 | NADH dehydrogenase | 63.16 | 225.7 | 6.40E-60 | 10 | 2.6 | 0 | 2.6 | 1 | 0 | 0.0% | | | 5 | 3 | 2 |
| 48 Y55H10A.1 | Y55H10A.1 | cadherin | 53.73 | 96.67 | 4.60E-21 | 33 | 1 | 0 | 1.6 | 1 | 0 | 0.0% | 80% Red | | 6 | 5 | 0 |
| 49 F29G9.3 | apt-2 | clathrin coat assembly | 89.55 | 266.9 | 6.10E-73 | 10 | 2.9 | 0 | 2.6 | 1.6 | 0 | 0.0% | | | 0 | 0 | 2 |
| 50 F27C1.7 | F27C1.7 | ATPase | 55.36 | 214.9 | 5.00E-57 | 24 | 2.3 | 0 | 2.8 | 0 | 0 | 0.0% | | | 2 | 2 | 0 |
| 51 Y55F3AR.3 | Y55F3AR.3 | TCP-1/cpn60 chaperon | 52 | 204.1 | 7.00E-147 | 26 | 1.3 | 0 | 2.6 | 3.8 | 0 | 0.0% | | | 17 | 10 | 0 |
| 52 F10C1.2 | ifb-1 | Intermediate filament p | 60.14 | 593.6 | 2.00E-170 | 12 | 1.9 | 2 | 1.6 | 1.6 | 0 | 0.0% | | | 1 | 0 | 3 |
| 53 F28H1.3 | ars-2 | aminoacyl-tRNA synthe | 49.58 | 307 | 2.00E-140 | 26 | 1.3 | 0 | 3.8 | 1.6 | 0 | 0.0% | | | 1 | 1 | 2 |
| 54 C52E4.6 | cyl-1 | Cyclin, N-terminal dom | 56 | 226.1 | 5.40E-60 | 10 | 2.6 | 0 | 2.6 | 2 | 0 | 0.0% | | | 1 | 1 | 0 |
| 55 T01C3.7 | fib-1 | fibrillarin | 79.73 | 221.5 | 9.30E-59 | 10 | 2.6 | 0 | 3.6 | 2 | 0 | 0.0% | | | 1 | 1 | 0 |
| 56 T05H4.6 | T05H4.6 | eukaryotic peptide chai | 74.75 | 298.5 | 3.00E-116 | 26 | 1.3 | 0 | 2.6 | 1.3 | 0 | 0.0% | | | 1 | 1 | 11 |
| 57 K08B4.1 | lag-1 | DNA-binding protein | 62 | 104.4 | 3.50E-23 | 17 | 1.6 | 2 | 2.6 | 0 | 0 | 0.0% | | | 1 | 1 | 0 |
| 58 C29F9.7 | pat-4 | integrin-linked kinase | 68.42 | 110.2 | 2.10E-37 | 10 | 3.2 | 0 | 4.3 | 2.7 | 0 | 0.0% | | | 4 | 3 | 0 |
| 59 T01H3.1 | T01H3.1 | proteolipid protein PPA | 75.81 | 180.6 | 5.20E-76 | 26 | 1 | 0 | 2.2 | 1 | 0 | 0.0% | 60% Red | | 0 | 0 | 0 |
| 60 B0361.10 | B0361.10 | synaptobrevin | 80 | 97.44 | 1.00E-35 | 15 | 3.2 | 0 | 1.6 | 2.6 | 0 | 0.0% | | | 1 | 0 | 4 |
| 61 F25B4.6 | F25B4.6 | hydroxymethylglutaryl-C | 57.96 | 276.9 | 2.60E-75 | 10 | 2.9 | 0 | 2.6 | 2.6 | 0 | 0.0% | | | 1 | 0 | 6 |
| 62 C04H5.6 | mog-4 | Helicases conserved C | 80.25 | 270 | 7.20E-73 | 10 | 2 | 0 | 3 | 1 | 0 | 0.0% | | | 1 | 0 | 0 |
| 63 T10F2.1 | grs-1 | Glycyl-tRNA synthetase | 70.38 | 565 | 1.00E-168 | 39 | 1.6 | 0 | 5.6 | 0 | 0.3 | 4.0% | | | 2 | 0 | 0 |
| 64 R74.1 | lrs-1 | leucyl-tRNA synthetase | 62.5 | 267.3 | 2.10E-72 | 10 | 2.3 | 0 | 3 | 1 | 0 | 0.0% | | | 1 | 0 | 3 |
| 65 T10E9.7 | T10E9.7 | NADH-ubiquinone oxidc | 74.19 | 249.2 | 5.50E-67 | 10 | 2.2 | 0 | 2.6 | 1 | 0 | 0.0% | | | 1 | 1 | 0 |
| 66 C50F2.3 | C50F2.3 | HAT (Half-A-TPR) repe | 66.96 | 231.9 | 6.00E-69 | 10 | 2 | 0 | 5.2 | 1 | 0 | 0.0% | | | 2 | 2 | 1 |
| 67 T25G3.3 | T25G3.3 | Yeast nonsense-media | 61.63 | 120 | 2.00E-60 | 10 | 2.2 | 0 | 3.6 | 2.6 | 0.3 | 3.4% | | | 1 | 0 | 0 |
| 68 R06A4.4 | imb-2 | importin beta, nuclear t | 55.63 | 108 | 2.60E-23 | 10 | 2 | 0 | 2.3 | 2.2 | 0 | 0.0% | | | 1 | 0 | 9 |
| 69 F19B6.2 | ufd-1 | Ubiquitin fusion degrad | 55.15 | 209.9 | 2.70E-55 | 10 | 2.9 | 0 | 2.6 | 2.6 | 0 | 0.0% | | | 4 | 2 | 0 |
| 70 F48E8.5 | paa-1 | Protein phosphatase 2A | 73.68 | 560.8 | 1.00E-160 | 16 | 1 | 1 | 5.3 | 1 | 0 | 0.0% | | | 3 | 1 | 0 |

FIG. 3A

| # | ID | Name | Description | Col5 | Col6 | Col7 | Col8 | Col9 | Col10 | Col11 | Col12 | Col13 | Col14 | Col15 | Col16 | Col17 |
|---|---|---|---|---|---|---|---|---|---|---|---|---|---|---|---|---|
| 71 | F18C12.2 | rme-8 | DNA-J like domain;Dna | 62.44 | 305.4 | 4.00E-149 | 16 | 1.8 | 1 | 3.2 | 2.2 | 0 | 0.0% | | 1 | 0 | 0 |
| 72 | F49C12.13 | vha-17 | ATP synthase subunit I | 72.34 | 124.8 | 1.40E-30 | 33 | 1.2 | 0 | 1.6 | 1 | 0 | 0.0% | 55% Red | 3 | 3 | 22 |
| 73 | F55A12.7 | apm-1 | clathrin coat assembly | 80.28 | 186 | 1.60E-47 | 34 | 3.2 | 0 | 0 | 3.6 | 0 | 0.0% | 50-60% Re | 1 | 0 | 0 |
| 74 | W01B11.3 | W01B11.3 | Putative snoRNA bindir | 69.18 | 217 | 8.00E-68 | 10 | 3.2 | 0 | 3 | 1 | 0 | 0.0% | | 2 | 0 | 1 |
| 75 | C37C3.6 | | unknown function | 81.69 | 142 | 5.00E-33 | 11 | 1.6 | 2 | 2 | 3.6 | 0 | 0.0% | | 1 | 1 | 3 |
| 76 | R13A5.12 | lpd-7 | BRCA1 C Terminus (BI | 56.67 | 199.9 | 4.60E-52 | 10 | 5.2 | 0 | 3.7 | 2 | 0 | 0.0% | | 1 | 0 | 1 |
| 77 | C42D4.8 | rpc-1 | DNA-directed RNA poly | 88.06 | 207.2 | 7.90E-54 | 10 | 2.6 | 0 | 3 | 1 | 0 | 0.0% | | 3 | 0 | 0 |
| 78 | F39B2.6 | rps-26 | 40S ribosomal protein | 85.09 | 204.9 | 1.60E-54 | 10 | 2.9 | 0 | 4.2 | 1 | 0 | 0.0% | | 4 | 2 | 0 |
| 79 | F28C6.3 | cpf-1 | cpf-1, mRNA cleavage | 66.38 | 306 | 9.00E-84 | 18 | 1 | 1 | 1 | 2 | 0 | 0.0% | | 3 | 1 | 4 |
| 80 | T17E9.2 | T17E9.2 | Myristoyl-CoA;protein N | 64.15 | 144.4 | 8.00E-60 | 10 | 2 | 0 | 4.6 | 2.2 | 0 | 0.0% | | 1 | 0 | 0 |
| 81 | K07A1.12 | lin-53 | chromatin assembly fa | 69.04 | 297 | 4.90E-86 | 24 | 2.3 | 0 | 3.2 | 0 | 0 | 0.0% | | 1 | 0 | 0 |
| 82 | D2085.1 | pyr-1 | glutamine-dependent c | 55.48 | 160 | 2.00E-40 | 18 | 1 | 1 | 1 | 2 | 0 | 0.0% | | 1 | 0 | 90 |
| 83 | Y52B11A.9 | Y52B11A.9 | Zinc finger, C2H2 type; | 81.97 | 113.2 | 1.30E-27 | 18 | 1 | 1.6 | 1.7 | 2.4 | 0 | 0.0% | | 1 | 1 | 0 |
| 84 | C30C11.2 | rpn-3 | Diphenol oxidase A2 | 43.81 | 220.3 | 3.20E-58 | 10 | 2 | 0 | 6.6 | 1 | 0 | 0.0% | | 0 | 0 | 0 |
| 85 | R160.1 | dpy-23 | clathrin coat assembly | 87.55 | 416.4 | 3.00E-117 | 14 | 2.6 | 1 | 0 | 1.6 | 0 | 0.0% | | 1 | 0 | 1 |
| 86 | F53G12.10 | rpl-7 | ribosomal protein | 76.79 | 339.3 | 1.90E-94 | 26 | 1.2 | 0 | 4.8 | 1 | 0 | 0.0% | | 15 | 11 | 10 |
| 87 | F55F8.5 | F55F8.5 | WD domain, G-beta rej | 51.11 | 143.7 | 3.20E-35 | 10 | 2.2 | 0 | 2 | 2.7 | 0 | 0.0% | | 1 | 0 | 2 |
| 88 | T27F2.1 | skp-1 | Drosophila puff specific | 76.36 | 88.2 | 1.30E-60 | 16 | 1.7 | 1 | 4.6 | 1 | 0 | 0.0% | | 1 | 0 | 0 |
| 89 | C47B2.4 | pbs-2 | Proteasome A-type anc | 50.36 | 135.6 | 5.00E-33 | 10 | 2.2 | 0 | 2.8 | 2.2 | 0 | 0.0% | | 1 | 0 | 12 |
| 90 | B0303.15 | B0303.15 | Ribosomal protein L11 | 60.23 | 201.8 | 3.50E-53 | 10 | 2.3 | 0 | 2 | 2 | 0 | 0.0% | | 2 | 2 | 146 |
| 91 | W10G6.3 | mua-6 | intermediate filament p | 68.92 | 772.7 | 0.00E+00 | 14 | 4.4 | 1 | 0 | 4.4 | 2 | 16.9% | | 1 | 0 | 0 |
| 92 | C39F7.4 | rab-1 | RAS-related protein | 87.88 | 346.7 | 9.40E-97 | 15 | 2 | 0 | 1.6 | 1 | 0 | 0.0% | | 7 | 4 | 146 |
| 93 | T26A5.7 | set-1 | SET domain;Nuclear pr | 48.59 | 179.9 | 1.90E-46 | 10 | 2 | 0 | 2 | 3.6 | 1 | 11.6% | | 1 | 1 | 0 |
| 94 | F14B4.3 | F14B4.3 | DNA-directed RNA poly | 76.12 | 327.4 | 3.00E-137 | 15 | 3.8 | 0 | 1 | 1 | 0 | 0.0% | | 2 | 1 | 2 |
| 95 | Y43F4B.5 | Y43F4B.5 | Phosphoglucomutase a | 61.85 | 444.5 | 1.00E-125 | 15 | 2.6 | 0 | 1 | 1 | 0.3 | 6.1% | | 0 | 0 | 0 |
| 96 | D1054.15 | tag-135 | beta transducin like prc | 67.47 | 120.9 | 4.00E-53 | 24 | 2 | 0 | 2.6 | 0 | 0 | 0.0% | | 1 | 0 | 0 |
| 97 | Y37D8A.10 | Y37D8A.10 | Microsomal signal pept | 50.41 | 124 | 8.20E-30 | 10 | 2.9 | 0 | 5.6 | 1.6 | 0 | 0.0% | | 2 | 2 | 0 |
| 98 | K02F2.2 | K02F2.2 | S-adenosylhomocystei | 82.67 | 339.3 | 4.00E-94 | 15 | 3.9 | 0 | 1 | 3.2 | 0 | 0.0% | | 2 | 2 | 27 |
| 99 | M57.2 | M57.2 | Protein prenyltransfera | 47.03 | 192.6 | 8.20E-50 | 18 | 1.2 | 1 | 1 | 2.6 | 0.3 | 4.9% | | 2 | 0 | 0 |
| 100 | T01D1.2 | etr-1 | RNA-binding protein | 58.76 | 238.7 | 1.30E-63 | 26 | 1 | 0 | 2.3 | 1 | 0 | 0.0% | | 2 | 2 | 0 |
| 101 | R06C7.8 | bub-1 | Eukaryotic protein kina | 41.26 | 146 | 1.50E-35 | 25 | 1 | 1 | 4.2 | 0.6 | 0 | 0.0% | | 1 | 0 | 0 |
| 102 | Y47D3A.26 | smc-3 | SMC proteins Flexible I | 57.03 | 263.5 | 5.90E-73 | 22 | 0 | 2 | 3 | 2.2 | 0 | 0.0% | | 1 | 0 | 0 |
| 103 | F22B5.1 | evl-20 | GTP-binding ADP-ribos | 45.51 | 157.9 | 5.20E-40 | 28 | 0 | 1.6 | 2.3 | 1.6 | 0 | 0.0% | | 9 | 7 | 57 |
| 104 | F25B5.4 | ubq-1 | Ubiquitin family;Ubiquit | 44.85 | 567.8 | 1.00E-162 | 24 | 2 | 0 | 3.6 | 0 | 0 | 0.0% | | 6 | 3 | 0 |
| 105 | F42C5.8 | rps-8 | 40S ribosomal protein | 72.97 | 300.8 | 6.00E-83 | 26 | 1.9 | 0 | 5.2 | 2 | 0 | 0.0% | | 19 | 15 | 7 |
| 106 | C17H12.14 | vha-8 | ATPase | 74.07 | 318.5 | 3.10E-88 | 15 | 2.3 | 0 | 1.6 | 1 | 0 | 0.0% | | 3 | 3 | 0 |
| 107 | B0564.1 | B0564.1 | ribonuclease PH like | 51.05 | 256.9 | 1.20E-69 | 15 | 2.6 | 0 | 1 | 2 | 0 | 0.0% | | 5 | 2 | 8 |
| 108 | R03G5.1 | eft-4 | elongation factor EF-1- | 89.76 | 847.4 | 0.00E+00 | 26 | 1.3 | 0 | 6.3 | 1.6 | 0 | 0.0% | | 0 | 0 | 16 |
| 109 | C47D12.6 | trs-1 | threonyl-tRNA synthet | 73.08 | 482 | 8.30E-136 | 24 | 2.6 | 0 | 2.6 | 0 | 0.3 | 5.5% | | 2 | 2 | 126 |
| 110 | Y47G6A.10 | spg-7 | ATPase | 86.14 | 466.1 | 5.00E-132 | 24 | 2.8 | 0 | 7.7 | 0.6 | 0 | 0.0% | | 2 | 2 | 0 |
| 111 | K07C5.6 | K07C5.6 | Zinc finger, CCHC clas | 62.21 | 290.8 | 2.50E-79 | 16 | 1 | 1 | 3.3 | 1 | 0 | 0.0% | | 1 | 0 | 0 |
| 112 | B0511.10 | eif-3.E | PCI domain;Proteasom | 73.53 | 196.8 | 2.50E-60 | 39 | 1.8 | 0 | 3.9 | 0 | 0 | 0.0% | | 1 | 1 | 8 |
| 113 | T02H6.11 | T02H6.11 | ubiquinol-cytochrome c | 45.53 | 120.6 | 5.00E-29 | 10 | 2.6 | 0 | 3.3 | 1 | 0 | 0.0% | | 17 | 6 | 10 |
| 114 | F13B10.2 | rpl-3 | 60S ribosomal protein | 77.02 | 384.8 | 7.00E-108 | 26 | 1.6 | 0 | 7.2 | 1 | 0 | 0.0% | | 73 | 72 | 0 |
| 115 | K12H4.3 | K12H4.3 | Brix domain;Brix | 65.52 | 82.8 | 2.10E-25 | 10 | 2.6 | 0 | 3 | 3 | 0 | 0.0% | | 0 | 0 | 5 |
| 116 | C01G8.5 | erm-1 | membrane protein | 72.13 | 167.2 | 3.60E-42 | 15 | 2.9 | 0 | 1.2 | 3.2 | 0 | 0.0% | | 1 | 0 | 0 |
| 117 | F36A2.6 | rps-15 | 40S ribosomal protein | 87.5 | 208 | 3.20E-55 | 15 | 3.2 | 0 | 1.6 | 1 | 0 | 0.0% | | 17 | 15 | 18 |
| 118 | W07E6.4 | prp-21 | splicing factor | 64.2 | 234.6 | 2.10E-62 | 22 | 0 | 2 | 3.6 | 1 | 0 | 0.0% | | 2 | 1 | 12 |
| 119 | C41G7.1 | smn-1 | Human muscular atropl | 57.5 | 110.9 | 8.80E-26 | 10 | 2.2 | 0 | 2 | 3.2 | 0 | 0.0% | | 0 | 0 | 0 |
| 120 | C34C12.8 | C34C12.8 | GRPE protein | 50.32 | 163.7 | 1.40E-41 | 15 | 2.6 | 0 | 1 | 1 | 0 | 0.0% | | 1 | 0 | 0 |
| 121 | C45G9.5 | C45G9.5 | unknown function | 39.78 | 160.6 | 1.70E-40 | 15 | 3.6 | 0 | 1.6 | 1 | 0 | 0.0% | | 1 | 1 | 0 |
| 122 | W08E3.1 | snr-2 | small nuclear ribonucle | 64.63 | 200.7 | 5.60E-53 | 25 | 1.9 | 1 | 3.8 | 0 | 0 | 0.0% | | 8 | 6 | 0 |
| 123 | JC8.3 | rpl-12 | Ribosomal protein L11 | 86.06 | 297.7 | 3.60E-82 | 26 | 1 | 0 | 3.6 | 2 | 0 | 0.0% | | 8 | 8 | 10 |
| 124 | F22D6.3 | nrs-1 | asparaginyl-tRNA synth | 65.61 | 290 | 3.50E-79 | 24 | 2.2 | 0 | 4.2 | 0 | 0.3 | 4.5% | | 3 | 2 | 0 |
| 125 | B0491.5 | B0491.5 | unknown function | 45.12 | 120.6 | 2.00E-28 | 24 | 3.3 | 0 | 2.3 | 0 | 0 | 0.0% | | 2 | 2 | 12 |
| 126 | F57B10.10 | dad-1 | DAD family;Defender a | 86.36 | 106 | 3.30E-24 | 10 | 2.2 | 0 | 2.2 | 1.6 | 0 | 0.0% | | 1 | 1 | 0 |
| 127 | H28O16.1 | | unknown function | 84.62 | 720.3 | 0.00E+00 | 26 | 1.3 | 0 | 2.2 | 1 | 0 | 0.0% | | 0 | 0 | 0 |
| 128 | T23F6.4 | rbd-1 | RNA recognition motif. | 50.57 | 109.8 | 1.10E-24 | 15 | 2.2 | 0 | 1 | 1 | 0 | 0.0% | | 1 | 1 | 1 |
| 129 | F23F12.6 | rpt-3 | rpt-3 encodes a triple A | 87.06 | 443.4 | 2.00E-125 | 26 | 1 | 0 | 3.6 | 1 | 0 | 0.0% | | 4 | 3 | 1 |
| 130 | Y39G10AR.8 | Y39G10AR | Elongation factor Tu dc | 81.44 | 344 | 1.70E-95 | 24 | 2.2 | 0 | 2.2 | 0 | 0 | 0.0% | | 1 | 0 | 0 |
| 131 | R12E2.3 | rpn-8 | Mov34/MPN/PAD-1 fan | 69.05 | 241.1 | 1.20E-64 | 24 | 2.3 | 0 | 4.8 | 0 | 0 | 0.0% | | 2 | 1 | 13 |
| 132 | K10B2.1 | lin-23 | Transducin beta chain | 90.2 | 559.3 | 4.00E-160 | 33 | 1.6 | 0 | 1.6 | 2 | 0 | 0.0% | | 1 | 0 | 16 |
| 133 | F01F1.8 | cct-6 | TCP-1/cpn60 chaperon | 74.06 | 397.5 | 2.00E-111 | 26 | 1.6 | 0 | 5.2 | 1.6 | 0 | 0.0% | | 9 | 0 | 94 |
| 134 | F08D12.1 | F08D12.1 | signal recognition parti | 45.3 | 86.7 | 1.60E-21 | 15 | 2.2 | 0 | 1.6 | 2.6 | 0 | 0.0% | | 1 | 0 | 0 |
| 135 | C47E12.1 | srs-2 | seryl-tRNA synthetase | 83.7 | 381.7 | 8.00E-107 | 26 | 1.3 | 0 | 2.2 | 1.6 | 0 | 0.0% | | 1 | 0 | 0 |
| 136 | C47E12.4 | C47E12.4 | inorganic pyrophosphat | 61.27 | 370.5 | 1.00E-103 | 26 | 1.6 | 0 | 4.3 | 1 | 0 | 0.0% | | 5 | 2 | 0 |
| 137 | F56F3.5 | rps-1 | Ribosomal protein S3a | 69.23 | 367.5 | 7.00E-103 | 26 | 1.3 | 0 | 6.2 | 1 | 0 | 0.0% | | 10 | 4 | 41 |
| 138 | C06E1.10 | C06E1.10 | ATP-dependent RNA h | 60.59 | 394.8 | 2.00E-110 | 33 | 1.6 | 0 | 1 | 1 | 0 | 0.0% | | 9 | 7 | 3 |
| 139 | F10G8.3 | npp-17 | npp-17, mRNA export p | 59.16 | 408 | 3.00E-114 | 38 | 0 | 2 | 0 | 10 | 0 | 0.0% | | 5 | 2 | 6 |
| 140 | C17G10.2 | C17G10.2 | TPR domain | 53.49 | 92.82 | 6.00E-24 | 10 | 2 | 0 | 2.6 | 2.2 | 0 | 0.0% | | 1 | 0 | 4 |
| 141 | K07C5.4 | K07C5.4 | yeast protein L8167.9-li | 57.47 | 110 | 1.30E-24 | 10 | 2.6 | 0 | 2.7 | 2 | 0 | 0.0% | | 1 | 1 | 0 |
| 142 | R13G10.1 | dpy-27 | chromosome segregati | 54.14 | 130.6 | 2.10E-43 | 26 | 1 | 0 | 2 | 1.6 | 1 | 17.9% | | 1 | 1 | 0 |
| 143 | B0432.3 | B0432.3 | unknown function | 55.38 | 174.5 | 5.30E-46 | 15 | 2.6 | 0 | 1 | 2 | 0.3 | 5.1% | | 4 | 4 | 0 |
| 144 | K04G7.11 | K04G7.11 | unknown function | 56.78 | 261.2 | 5.50E-71 | 16 | 1 | 1.2 | 2 | 3.4 | 1 | 11.6% | | 3 | 2 | 0 |
| 145 | E04A4.8 | rpl-20 | ribosomal protein | 69.44 | 270.8 | 5.40E-74 | 26 | 1.2 | 0 | 5.2 | 2.6 | 0 | 0.0% | | 29 | 23 | 3 |
| 146 | T12A2.7 | T12A2.7 | Breast carcinoma ampl | 38.28 | 161 | 9.00E-41 | 10 | 2 | 0 | 2 | 2.3 | 1 | 13.7% | | 7 | 7 | 16 |
| 147 | C09D4.5 | rpl-19 | 60S ribosomal protein | 79.27 | 315.1 | 2.80E-87 | 24 | 3.9 | 0 | 3.8 | 0 | 0 | 0.0% | | 7 | 5 | 0 |
| 148 | C14B9.4 | plk-1 | Protein kinase | 57.07 | 208.8 | 7.00E-90 | 24 | 2 | 0 | 9.2 | 0 | 0 | 0.0% | | 2 | 2 | 0 |
| 149 | F25B3.6 | F25B3.6 | Plus-3 domain;Plus-3 | 38.08 | 140.6 | 3.90E-34 | 10 | 2.2 | 0 | 2.3 | 1.6 | 0 | 0.0% | | 3 | 2 | 0 |

FIG. 3B

| | | | | | | | | | | | | | | | |
|---|---|---|---|---|---|---|---|---|---|---|---|---|---|---|---|
| 150 | ZK622.3 | ZK622.3 | Generic methyltransfer | 49.74 | 189.1 | 7.40E-49 | 26 | 1.6 | 0 | 2 | 1.6 | 0 | 0.0% | | 1 | 1 | 0 |
| 151 | D1014.3 | D1014.3 | alpha-SNAP protein | 66.67 | 100 | 4.00E-21 | 26 | 1 | 0 | 5.2 | 3 | 0 | 0.0% | 30-80% Re | 4 | 1 | 5 |
| 152 | F26F4.10 | rrt-1 | arginyl tRNA synthetas | 38.85 | 159.1 | 9.60E-57 | 26 | 1.6 | 0 | 8.3 | 2 | 0 | 0.0% | | 2 | 1 | 1 |
| 153 | K04G2.1 | K04G2.1 | translational initiation fa | 65.71 | 211.5 | 6.20E-56 | 24 | 2.2 | 0 | 2.9 | 0 | 0 | 0.0% | | 1 | 1 | 1 |
| 154 | C47E8.4 | C47E8.4 | XAP5 protein | 53.36 | 208 | 1.10E-54 | 15 | 2 | 0 | 1 | 1 | 1 | 20.0% | | 1 | 1 | 16 |
| 155 | R03E1.2 | R03E1.2 | unknown function | 39.05 | 74.71 | 1.30E-14 | 37 | 2.2 | 0 | 0.6 | 0.6 | 0 | 0.0% | 75% Red | 1 | 0 | 3 |
| 156 | F38E11.5 | F38E11.5 | beta'-coat protein like | 82.5 | 150 | 4.00E-60 | 33 | 1 | 0 | 1.6 | 1 | 0 | 0.0% | | 1 | 0 | 1 |
| 157 | T09A5.11 | T09A5.11 | N-oligosaccharyl transf | 53.95 | 228 | 3.00E-76 | 33 | 1.6 | 0 | 1.6 | 2 | 0 | 0.0% | | 1 | 0 | 1 |
| 158 | F36A2.7 | F36A2.7 | unknown function | 48.82 | 129.8 | 1.30E-31 | 26 | 2.9 | 0 | 2.9 | 1.7 | 0 | 0.0% | | 0 | 0 | 3 |
| 159 | M88.2 | M88.2 | unknown function | 61.4 | 227.6 | 7.40E-61 | 10 | 2 | 0 | 2 | 1.6 | 1.3 | 18.8% | | 1 | 1 | 1 |
| 160 | ZC434.2 | rps-7 | 40S ribosomal protein | 60.11 | 244.2 | 6.10E-66 | 24 | 2.9 | 0 | 2.6 | 0 | 0 | 0.0% | | 15 | 14 | 50 |
| 161 | H15N14.2 | nsf-1 | vesicular-fusion protein | 52.94 | 243.8 | 2.10E-64 | 24 | 3 | 0 | 5.6 | 0 | 0 | 0.0% | | 1 | 0 | 0 |
| 162 | F59C6.5 | F59C6.5 | NADH ubiquinone oxid | 49.03 | 220.3 | 1.40E-58 | 24 | 2.2 | 0 | 3.2 | 0 | 0 | 0.0% | | 2 | 1 | 0 |
| 163 | LLC1.3 | LLC1.3 | dihydrolipoamide dehy | 72.66 | 193 | 4.00E-49 | 24 | 3.2 | 0 | 3.2 | 0 | 1 | 13.5% | | 3 | 1 | 1 |
| 164 | C10H11.9 | let-502 | Rho-associated kinase | 47.8 | 181.4 | 1.10E-55 | 24 | 2.2 | 0 | 3.8 | 0 | 0 | 0.0% | | 3 | 1 | 8 |
| 165 | F59A3.3 | F59A3.3 | KOW motif | 40.85 | 178.3 | 6.70E-46 | 24 | 2.2 | 0 | 2.7 | 0 | 0 | 0.0% | | 4 | 1 | 1 |
| 166 | D1007.12 | rpl-24.1 | 60S ribosomal protein l | 55.28 | 177.9 | 3.80E-46 | 24 | 2.9 | 0 | 3.8 | 0 | 0 | 0.0% | | 18 | 12 | 0 |
| 167 | F26H9.6 | rab-5 | RAS-related protein | 94.32 | 171 | 3.00E-43 | 26 | 2.9 | 0 | 2.2 | 0 | 0 | 0.0% | | 1 | 0 | 1 |
| 168 | Y71G12B.11 | Y71G12B. | FERM domain (Band 4 | 55.49 | 185.3 | 4.00E-70 | 10 | 4.2 | 0.6 | 2.8 | 4.8 | 2 | 13.9% | | 1 | 1 | 0 |
| 169 | C37A2.4 | cye-1 | cyclin | 39.74 | 137.5 | 2.30E-33 | 24 | 4.2 | 0 | 6.2 | 0 | 0 | 0.0% | | 2 | 1 | 2 |
| 170 | B0511.8 | B0511.8 | Mitochondrial 28S ribos | 40.77 | 336.7 | 3.20E-93 | 24 | 3.2 | 0 | 2.6 | 0 | 0 | 0.0% | | 0 | 0 | 0 |
| 171 | T22D1.10 | ruvb-2 | TIP49 C-terminus;AAA | 63.41 | 513.8 | 1.00E-146 | 26 | 1.6 | 0 | 3.6 | 3 | 0 | 0.0% | | 4 | 2 | 0 |
| 172 | F10B5.1 | rpl-10 | ribosomal protein L10 ( | 79.91 | 365.5 | 2.00E-102 | 26 | 1.3 | 0 | 5.6 | 1 | 0 | 0.0% | | 21 | 9 | 14 |
| 173 | F23F1.8 | | unknown function | 82.41 | 362.5 | 2.00E-128 | 26 | 1 | 0 | 4.2 | 3 | 0 | 0.0% | | 1 | 1 | 7 |
| 174 | F55F8.4 | F55F8.4 | unknown function | 79.88 | 285 | 1.20E-77 | 24 | 2 | 0 | 5.2 | 0 | 0 | 0.0% | | 2 | 0 | 0 |
| 175 | Y48G8AL.8 | rpl-17 | Ribosomal protein L22 | 76.47 | 292.4 | 1.80E-80 | 26 | 1.2 | 0 | 3.2 | 1 | 0 | 0.0% | | 4 | 2 | 0 |
| 176 | K08E4.1 | spt-5 | translation initiation pro | 46.32 | 242.3 | 1.00E-176 | 26 | 1 | 0 | 2.6 | 1 | 0 | 0.0% | | 1 | 0 | 0 |
| 177 | C08B11.3 | C08B11.3 | Zinc finger, C2H2 type | 39.15 | 147.1 | 8.70E-36 | 24 | 2 | 0 | 3.6 | 0 | 0 | 0.0% | | 1 | 1 | 0 |
| 178 | Y51H7C.6 | Y51H7C.6 | unknown function | 42.86 | 136.7 | 3.60E-32 | 12 | 1.8 | 3 | 1 | 9.8 | 3 | 16.1% | | 1 | 0 | 1 |
| 179 | C26D10.2 | hel-1 | translation initiation fac | 77.23 | 315.5 | 5.90E-87 | 26 | 1 | 0 | 3.6 | 1 | 0 | 0.0% | | 2 | 1 | 5 |
| 180 | D1054.14 | D1054.14 | PRP38 family;PRP38 | 65.79 | 312.8 | 2.70E-86 | 26 | 1 | 0 | 4.3 | 2 | 0 | 0.0% | | 1 | 1 | 0 |
| 181 | T14G10.5 | T14G10.5 | protein transport protei | 72.55 | 298.5 | 1.60E-81 | 26 | 1 | 0 | 2.6 | 3.2 | 0 | 0.0% | | 1 | 0 | 0 |
| 182 | F53G12.1 | rab-11.1 | RAS-related protein | 96.23 | 342.4 | 1.90E-95 | 24 | 2 | 0 | 2 | 0 | 1 | 20.0% | | 1 | 1 | 2 |
| 183 | D2013.5 | eat-3 | GTP-binding protein | 65.45 | 393 | 8.00E-109 | 26 | 1.6 | 0 | 3.6 | 1 | 0.3 | 4.6% | | 4 | 3 | 0 |
| 184 | R13A5.8 | rpl-9 | Ribosomal protein L9 | 81.54 | 280.8 | 5.60E-77 | 26 | 1.3 | 0 | 5 | 1 | 0 | 0.0% | | 15 | 10 | 0 |
| 185 | F09F7.3 | F09F7.3 | RNA polymerase beta | 65.69 | 352.8 | 0.00E+00 | 26 | 1.6 | 0 | 2.6 | 1 | 1 | 16.1% | | 1 | 0 | 1 |
| 186 | F38H4.9 | let-92 | serine/threonine protei | 84.38 | 292.7 | 2.90E-80 | 26 | 1.7 | 0 | 3.6 | 1 | 0 | 0.0% | | 1 | 1 | 1 |
| 187 | F01G12.5 | let-2 | alpha-2 type IV collage | 80.3 | 342.8 | 1.50E-94 | 26 | 1.6 | 0 | 2 | 1.2 | 1 | 17.2% | | 1 | 1 | 8 |
| 188 | B0464.1 | drs-1 | Aspartyl-tRNA synthet | 59.34 | 276.9 | 3.00E-75 | 26 | 1 | 0 | 5.6 | 1 | 0 | 0.0% | | 2 | 2 | 12 |
| 189 | B0336.2 | arf-1.2 | ARF | 95 | 351.7 | 2.40E-98 | 28 | 0 | 1 | 6.3 | 2.2 | 0 | 0.0% | | 9 | 7 | 0 |
| 190 | F29B9.6 | ubc-9 | ubiquitin-conjugating er | 76.97 | 279.6 | 1.00E-76 | 28 | 0 | 1 | 2.6 | 2.2 | 0 | 0.0% | | 4 | 2 | 0 |
| 191 | C53H9.2 | C53H9.2 | GTPase of unknown fu | 39.84 | 171 | 1.70E-42 | 26 | 1.2 | 0 | 3.2 | 1 | 0 | 0.0% | | 0 | 0 | 8 |
| 192 | C37C3.2 | C37C3.2 | eIF4-gamma/eIF5/eIF2 | 66.3 | 216.9 | 1.40E-81 | 26 | 1.3 | 0 | 4.2 | 2 | 0 | 0.0% | | 1 | 0 | 1 |
| 193 | C35B1.1 | ubc-1 | ubiquitin conjugating-p | 72.12 | 253 | 2.00E-67 | 34 | 2 | 0 | 0 | 1 | 1 | 25.0% | | 1 | 1 | 0 |
| 194 | C38C3.5 | unc-60 | actin depolymerizing fa | 67.7 | 217.2 | 9.10E-58 | 34 | 2.4 | 0 | 0 | 1 | 0 | 0.0% | | 5 | 3 | 0 |
| 195 | C48B6.2 | C48B6.2 | ribosomal protein | 58.62 | 191 | 5.50E-50 | 34 | 3.1 | 0 | 0 | 1 | 0 | 0.0% | | 2 | 2 | 0 |
| 196 | T09B4.9 | T09B4.9 | Tim44-like domain;Mitc | 56.25 | 253.8 | 2.10E-68 | 26 | 1.9 | 0 | 3.2 | 1 | 0 | 0.0% | | 1 | 1 | 5 |
| 197 | T26G10.1 | T26G10.1 | RNA helicase | 66.67 | 279.3 | 5.50E-76 | 10 | 2.6 | 0 | 3.7 | 1 | 2 | 21.5% | | 1 | 0 | 36 |
| 198 | F54C9.5 | rpl-5 | 60S ribosomal protein l | 65.88 | 277.7 | 8.70E-76 | 26 | 1.3 | 0 | 4.6 | 1 | 0 | 0.0% | | 1 | 0 | 3 |
| 199 | H06I04.3 | H06I04.3 | FtsJ-like methyltransfer | 48.9 | 149.8 | 2.20E-60 | 10 | 4.8 | 0 | 2 | 1 | 2.3 | 22.8% | | 1 | 1 | 1 |
| 200 | T19A6.2 | ngp-1 | AUTOANTIGEN NGP- | 74.65 | 106.7 | 8.00E-46 | 26 | 1.6 | 0 | 2 | 1 | 0 | 0.0% | | 4 | 2 | 11 |
| 201 | M106.1 | mix-1 | mitotic chromosome ar | 49.07 | 99.8 | 2.00E-36 | 26 | 1 | 0 | 4 | 1 | 0 | 0.0% | | 2 | 0 | 64 |
| 202 | W08D2.7 | W08D2.7 | Human myeloid cell lin | 55.68 | 265.8 | 5.00E-76 | 26 | 1.6 | 0 | 2.6 | 3.6 | 0 | 0.0% | | 0 | 0 | 44 |
| 203 | C27H6.2 | ruvb-1 | Yeast hypothetical 50.5 | 67.62 | 276.2 | 4.40E-75 | 26 | 1.6 | 0 | 2.6 | 2 | 0.3 | 4.6% | | 4 | 2 | 0 |
| 204 | T04A8.11 | T04A8.11 | 50S ribosomal protein l | 56.74 | 273.1 | 1.40E-74 | 26 | 1.6 | 0 | 2.3 | 1 | 0 | 0.0% | | 6 | 6 | 68 |
| 205 | R10E11.8 | vha-1 | ATP synthase subunit | 81.18 | 255.4 | 2.10E-69 | 26 | 1 | 0 | 4.2 | 1 | 0 | 0.0% | | 7 | 5 | 12 |
| 206 | K08E5.3 | mua-3 | LDL receptor related pr | 63.36 | 192 | 9.00E-48 | 15 | 4.2 | 0 | 1 | 3.2 | 2 | 19.2% | | 1 | 1 | 48 |
| 207 | F43G9.10 | F43G9.10 | MICROFIBRILLAR-AS | 69.88 | 129.4 | 3.10E-30 | 26 | 1 | 0 | 4.9 | 1 | 0 | 0.0% | | 1 | 0 | 2 |
| 208 | R144.2 | R144.2 | Regulation of nuclear p | 52.21 | 124 | 1.00E-30 | 26 | 1 | 0 | 3.6 | 1 | 0 | 0.0% | | 1 | 0 | 4 |
| 209 | Y54E2A.11 | eif-3.B | Translation initiation fac | 55.79 | 160.6 | 4.40E-40 | 26 | 1.6 | 0 | 2.6 | 2 | 0 | 0.0% | | 1 | 0 | 38 |
| 210 | F39H11.5 | pbs-7 | Yeast NIP80 protein lik | 42.63 | 142.9 | 2.50E-35 | 26 | 1.2 | 0 | 4.8 | 2.2 | 0 | 0.0% | | 2 | 2 | 0 |
| 211 | T02G5.9 | krs-1 | lysyl-tRNA synthetase | 81.97 | 109 | 6.40E-33 | 26 | 1.3 | 0 | 2.6 | 1.7 | 0 | 0.0% | | 1 | 1 | 0 |
| 212 | C34E10.2 | gop-2 | Conserved hypothetica | 79.25 | 292 | 5.70E-80 | 26 | 1 | 0 | 4.6 | 1.6 | 0.3 | 4.0% | | 2 | 1 | 3 |
| 213 | C25F6.2 | dlg-1 | guanylate kinase | 58.84 | 334.3 | 3.00E-92 | 31 | 2 | 0 | 1 | 0 | 0 | 0.0% | WT | 2 | 2 | 46 |
| 214 | F43E2.8 | hsp-4 | heat shock protein | 79.24 | 1031.6 | 0.00E+00 | 33 | 1.3 | 0 | 1.6 | 1 | 0 | 0.0% | | 1 | 0 | 0 |
| 215 | Y39E4B.1 | Y39E4B.1 | Possible metal-binding | 79.17 | 272.3 | 8.60E-74 | 26 | 1 | 0 | 3 | 2.2 | 0 | 0.0% | | 1 | 1 | 29 |
| 216 | F18H3.5 | cdk-4 | cdk-4, cyclin-dependen | 47.03 | 213 | 1.00E-55 | 29 | 1 | 1 | 0 | 9 | 1 | 8.3% | | 3 | 3 | 12 |
| 217 | C41C4.8 | C41C4.8 | P97 protein | 88.16 | 415.2 | 1.00E-116 | 33 | 1 | 0 | 1 | 1.2 | 0 | 0.0% | | 1 | 0 | 1 |
| 218 | R09B3.5 | mag-1 | MAGO NASHI PROTE | 80.82 | 251.1 | 3.30E-68 | 26 | 1.9 | 0 | 2.9 | 1 | 0 | 0.0% | | 1 | 1 | 0 |
| 219 | F13D11.2 | hbl-1 | C2H2-type zinc finger | 66.67 | 114 | 5.90E-48 | 31 | 2.2 | 0 | 1.6 | 0.6 | 0 | 0.0% | | 1 | 0 | 146 |
| 220 | Y53G8AL.2 | Y53G8AL. | unknown function | 60.29 | 241.9 | 8.40E-65 | 26 | 1.2 | 0 | 3.2 | 4 | 0 | 0.0% | | 1 | 0 | 8 |
| 221 | Y53F4B.22 | Y53F4B.22 | actin-like protein | 53.66 | 412.5 | 3.00E-116 | 33 | 1.9 | 0.6 | 1.6 | 2.6 | 0 | 0.0% | | 367 | 10 | 0 |
| 222 | Y71F9AL.17 | Y71F9AL.1 | coatomer, alpha chain | 64.06 | 260.8 | 5.30E-70 | 26 | 1 | 0 | 2.8 | 1.6 | 0 | 0.0% | | 3 | 3 | 1 |
| 223 | W09C5.8 | W09C5.8 | Cytochrome C oxidase | 76.36 | 176.8 | 1.00E-45 | 26 | 1.2 | 0 | 2.2 | 2 | 0.3 | 5.3% | | 7 | 5 | 0 |
| 224 | C47E8.7 | unc-112 | mitogen inducible MIG- | 58.9 | 383.3 | 4.00E-107 | 33 | 1 | 0 | 1.6 | 3 | 0 | 0.0% | | 3 | 1 | 10 |
| 225 | C53D5.6 | imb-3 | importin beta, nuclear t | 48.48 | 152.9 | 1.40E-37 | 26 | 1.2 | 0 | 5.8 | 2 | 0.3 | 3.2% | | 3 | 0 | 0 |
| 226 | Y47G6A.8 | cm-1 | endonuclease | 46.34 | 116.7 | 1.60E-26 | 28 | 0 | 1.3 | 4.2 | 1.9 | 0 | 0.0% | | 1 | 0 | 37 |
| 227 | C47B2.5 | eif-6 | eIF-6, Translation initia | 73.33 | 279 | 1.00E-75 | 34 | 3 | 0 | 0 | 1 | 0 | 0.0% | | 2 | 1 | 63 |
| 228 | E02H1.1 | E02H1.1 | rRNA methyltransferas | 73.47 | 342 | 4.00E-95 | 33 | 1.3 | 0 | 1 | 1 | 0 | 0.0% | | 3 | 2 | 0 |
| 229 | C32E8.2 | rpl-13 | ribosomal protein L13 | 70 | 231.1 | 5.80E-62 | 26 | 1.3 | 0 | 2.2 | 1 | 0 | 0.0% | | 6 | 2 | 0 |

FIG. 3C

| # | ID | Gene | Description | Val1 | Val2 | Val3 | Val4 | Val5 | Val6 | Val7 | Val8 | Val9 | Val10 | Note | V12 | V13 | V14 |
|---|---|---|---|---|---|---|---|---|---|---|---|---|---|---|---|---|---|
| 230 | F53A3.3 | rps-22 | 40S ribosomal protein | 88.24 | 230.7 | 3.40E-62 | 26 | 1.3 | 0 | 3 | 2 | 0 | 0.0% | | 12 | 12 | 0 |
| 231 | C26E6.8 | ula-1 | component of the enzyr | 56.47 | 101.3 | 3.00E-38 | 30 | 0 | 1.6 | 1.7 | 1 | 1 | 18.9% | | 1 | 0 | 1 |
| 232 | ZK742.1 | imb-4 | importin beta, nuclear t | 93.59 | 179 | 5.60E-99 | 33 | 1.6 | 0 | 1.6 | 1.6 | 0 | 0.0% | | 1 | 0 | 4 |
| 233 | F33D4.5 | F33D4.5 | Ribosomal protein L1p/ | 48.12 | 250 | 2.60E-67 | 26 | 1.3 | 0 | 2.3 | 1 | 0 | 0.0% | | 0 | 0 | 1 |
| 234 | H37A05.1 | H37A05.1 | lipin, N-terminal conser | 71.88 | 236.9 | 1.90E-72 | 26 | 1 | 0 | 2 | 1 | 0 | 0.0% | | 1 | 0 | 0 |
| 235 | ZK909.2 | kin-1 | Protein kinase C termir | 80.87 | 191 | 4.00E-131 | 36 | 1 | 1 | 0 | 0 | 0 | 0.0% | | 1 | 0 | 0 |
| 236 | C06A1.1 | C06A1.1 | transitional endoplasmi | 89.47 | 417.5 | 2.00E-117 | 27 | 1 | 1 | 1 | 0 | 0 | 0.0% | | 1 | 0 | 54 |
| 237 | F28D1.10 | gex-3 | Drosophila dhem transi | 45.95 | 105.1 | 1.70E-22 | 26 | 1.6 | 0 | 2.6 | 1.6 | 0 | 0.0% | | 1 | 0 | 0 |
| 238 | F49C12.8 | rpn-7 | PCI domain;Proteasom | 57.07 | 230.7 | 1.90E-61 | 26 | 1 | 0 | 8.2 | 1 | 0 | 0.0% | | 1 | 1 | 59 |
| 239 | ZC518.2 | sec-24.2 | Yeast YIK9 like | 51.83 | 224.6 | 3.40E-59 | 26 | 1 | 0 | 2.6 | 2.2 | 0 | 0.0% | | 1 | 0 | 18 |
| 240 | F26A3.2 | F26A3.2 | Cap binding protein | 68.63 | 232.6 | 1.20E-62 | 39 | 1.6 | 0 | 2 | 0 | 0 | 0.0% | | 5 | 2 | 1 |
| 241 | Y110A2AL.8 | ptc-3 | Patched family;Patchec | 48.98 | 198.7 | 1.00E-74 | 34 | 5.4 | 0 | 0.6 | 7.8 | 1 | 6.8% | | 3 | 3 | 27 |
| 242 | T23F2.1 | T23F2.1 | glycosyltransferase | 51.66 | 142.9 | 2.50E-34 | 29 | 1 | 1 | 0 | 1.8 | 0 | 0.0% | | 0 | 0 | 0 |
| 243 | C26D10.1 | ran-3 | regulator of chromoson | 62.75 | 198.4 | 1.50E-51 | 26 | 1 | 0 | 3 | 1 | 0 | 0.0% | | 4 | 1 | 0 |
| 244 | Y38A8.2 | pbs-3 | Proteasome A-type and | 43.14 | 189.1 | 2.50E-49 | 26 | 1 | 0 | 2.6 | 1 | 0 | 0.0% | | 12 | 7 | 92 |
| 245 | F55A12.8 | F55A12.8 | Putative ATPase (DUF) | 61.4 | 244.6 | 3.30E-65 | 33 | 1.2 | 0 | 1.2 | 2 | 0 | 0.0% | 20% Red | 2 | 0 | 0 |
| 246 | D2013.7 | eif-3.F | MOV-34 protein | 45.53 | 222.6 | 3.30E-59 | 33 | 1.6 | 0 | 1.6 | 1 | 0 | 0.0% | | 4 | 2 | 0 |
| 247 | F29D11.1 | lrp-1 | low density lipid recept | 73.56 | 147.1 | 1.60E-34 | 34 | 2.8 | 0 | 0 | 4.2 | 0 | 0.0% | | 1 | 0 | 0 |
| 248 | F56H1.4 | rpt-5 | ATPase | 83.61 | 686.8 | 0.00E+00 | 39 | 1 | 0 | 6.8 | 0 | 0 | 0.0% | | 8 | 6 | 146 |
| 249 | K08E3.5 | K08E3.5 | UTP--GLUCOSE-1-PH | 57.45 | 188.7 | 1.10E-48 | 26 | 1.3 | 0 | 4.3 | 1 | 0 | 0.0% | | 3 | 2 | 0 |
| 250 | D2024.6 | cap-1 | F-actin capping protein | 52.94 | 185.3 | 5.60E-48 | 26 | 1 | 0 | 3.7 | 1 | 0 | 0.0% | | 1 | 0 | 0 |
| 251 | T27B1.2 | T27B1.2 | zinc finger | 50 | 149.8 | 3.00E-36 | 31 | 2.2 | 0 | 1.6 | 0.6 | 0 | 0.0% | | 1 | 1 | 4 |
| 252 | C03C10.3 | mr-2 | Ribonuclease-diphosph | 76.19 | 366.7 | 2.00E-105 | 42 | 0 | 1 | 4.6 | 0 | 0 | 0.0% | WT | 1 | 0 | 8 |
| 253 | C04F12.4 | rpl-14 | ribosomal protein L14 | 65.93 | 179.9 | 7.40E-47 | 26 | 1.9 | 0 | 2.2 | 1 | 0 | 0.0% | | 9 | 5 | 0 |
| 254 | K02A11.1 | gfi-2 | ankyrin motifs | 55.19 | 185 | 7.00E-76 | 42 | 0.6 | 1 | 1.2 | 0.6 | 0.3 | 8.1% | | 1 | 0 | 0 |
| 255 | T28D9.10 | snr-3 | small nuclear ribonucle | 77.27 | 175.3 | 1.60E-45 | 26 | 1.3 | 0 | 2.3 | 1 | 0 | 0.0% | | 5 | 2 | 10 |
| 256 | Y56A3A.32 | wah-1 | Pyridine nucleotide-dis | 50 | 86.3 | 1.20E-26 | 26 | 1 | 0 | 2 | 1.6 | 1 | 17.9% | | 1 | 0 | 3 |
| 257 | F55A11.2 | syn-3 | epimorphin protein | 65.45 | 174.5 | 1.60E-44 | 26 | 1.6 | 0 | 2.3 | 2.3 | 0 | 0.0% | 10-15% Re | 2 | 1 | 0 |
| 258 | W09G12.5 | W09G12.5 | GTP-binding protein | 68.75 | 147 | 4.00E-36 | 33 | 1.2 | 0 | 1.6 | 1 | 0 | 0.0% | | 2 | 2 | 1 |
| 259 | R05D11.3 | ran-4 | nuclear transport factor | 61.54 | 172.2 | 1.50E-44 | 26 | 1.2 | 0 | 3.2 | 1.6 | 0 | 0.0% | | 3 | 1 | 0 |
| 260 | C18D1.1 | die-1 | Zinc finger, C2H2 type | 72.22 | 112.1 | 3.00E-30 | 33 | 1 | 0 | 1.6 | 1 | 0.3 | 7.7% | | 1 | 0 | 5 |
| 261 | M03F4.7 | M03F4.7 | calcium binding protein | 78.46 | 115.9 | 2.10E-26 | 29 | 1.2 | 1 | 0 | 1.6 | 0.3 | 7.3% | | 3 | 3 | 2 |
| 262 | C09H10.3 | nuo-1 | NADH-ubiquinone oxid | 80 | 207.2 | 2.60E-54 | 41 | 1.6 | 0 | 1.6 | 0 | 0 | 0.0% | | 1 | 0 | 14 |
| 263 | C56C10.3 | C56C10.3 | SNF7 | 58.82 | 82.8 | 4.90E-30 | 33 | 1.6 | 0 | 1.6 | 1 | 0 | 0.0% | | 3 | 0 | 0 |
| 264 | H19M22.2 | let-805 | Fibronectin type III dom | 55.02 | 241.5 | 1.10E-63 | 26 | 1.6 | 0 | 2.8 | 2 | 2 | 23.8% | 45-55% Re | 2 | 0 | 1 |
| 265 | C41D11.2 | eif-3.H | PF01398 (Mov34/MPN | 53.92 | 218.8 | 6.30E-58 | 33 | 1 | 0 | 1.6 | 2.8 | 0 | 0.0% | | 6 | 5 | 6 |
| 266 | F26E4.9 | cco-1 | cytochrome C oxidase | 57.85 | 164.9 | 2.30E-42 | 26 | 1.2 | 0 | 3.2 | 2 | 0 | 0.0% | | 1 | 0 | 1 |
| 267 | F37E3.1 | F37E3.1 | CAP-binding protein | 34.86 | 79.34 | 6.70E-15 | 3 | 2.8 | 1 | 3 | 3.6 | 0 | 0.0% | | 1 | 0 | 0 |
| 268 | F12F6.6 | sec-24.1 | Yeast hypothetical YIK | 44.59 | 118.2 | 1.90E-26 | 15 | 2 | 0 | 1.6 | 1 | 0 | 0.0% | | 0 | 0 | 27 |
| 269 | R09B3.4 | ubc-12 | Ubiquitin-conjugating e | 62.78 | 239.6 | 1.30E-64 | 28 | 0 | 1 | 2.2 | 2.2 | 0.3 | 5.3% | | 8 | 8 | 0 |
| 270 | Y65B4BR.5 | Y65B4BR.1 | UBA/TS-N domain;NAC | 63.68 | 236.9 | 9.90E-64 | 28 | 0.6 | 1 | 3.6 | 4.4 | 0 | 0.0% | | 13 | 11 | 4 |
| 271 | R07E5.10 | R07E5.10 | Apoptosis protein RP-8 | 35.37 | 105.9 | 5.60E-24 | 10 | 2 | 0 | 3 | 1.6 | 0 | 0.0% | | 1 | 0 | 0 |
| 272 | F32H2.1 | gei-11 | protooncogene C-MYB | 36.59 | 91.3 | 4.00E-33 | 10 | 2 | 0 | 2.7 | 1 | 0 | 0.0% | | 1 | 0 | 0 |
| 273 | ZC513.4 | vrs-1 | valyl-tRNA synthetase | 77.78 | 149.1 | 1.70E-36 | 26 | 1.3 | 0 | 2.6 | 1 | 0 | 0.0% | | 2 | 2 | 0 |
| 274 | C27A2.6 | dsh-2 | DIX domain, a DEP dor | 43.56 | 86.27 | 9.40E-18 | 16 | 1 | 1.6 | 2.7 | 2 | 0 | 0.0% | | 1 | 1 | 7 |
| 275 | Y110A7A.13 | chp-1 | two CHORD domains, i | 62.79 | 162.5 | 4.60E-41 | 26 | 1 | 0 | 2.2 | 1 | 0 | 0.0% | | 1 | 0 | 0 |
| 276 | T08G11.4 | T08G11.4 | SAM binding motif | 64.71 | 86.66 | 6.20E-18 | 10 | 2.2 | 0 | 2.2 | 2.2 | 0 | 0.0% | | 1 | 1 | 2 |
| 277 | C17E4.5 | pab-3 | RNA binding protein (R | 55.7 | 85.11 | 5.10E-18 | 10 | 3.9 | 0 | 3.9 | 4.2 | 0 | 0.0% | | 1 | 0 | 38 |
| 278 | C15H11.9 | C15H11.9 | Human HA0609 proteir | 54.6 | 179.5 | 3.80E-46 | 26 | 1.6 | 0 | 3 | 2 | 0.3 | 4.3% | | 5 | 3 | 0 |
| 279 | T01C3.1 | T01C3.1 | WD domain, G-beta re | 36.51 | 130.6 | 4.90E-31 | 30 | 0 | 1.6 | 1 | 3.2 | 0.3 | 4.9% | | 3 | 1 | 3 |
| 280 | Y47D3B.1 | Y47D3B.1 | DUF23;Rhodopsin-like | 41.57 | 114 | 4.70E-73 | 37 | 2 | 0 | 0 | 0 | 1 | 33.3% | | 4 | 2 | 0 |
| 281 | ZK430.1 | ZK430.1 | unknown function | 30 | 109.4 | 1.30E-23 | 15 | 2.2 | 0 | 1.6 | 3 | 0 | 0.0% | | 1 | 0 | 1 |
| 282 | T23D8.3 | T23D8.3 | domain - Low temperat | 36.23 | 96.29 | 5.40E-21 | 15 | 3.5 | 0 | 1 | 1 | 0 | 0.0% | | 1 | 1 | 1 |
| 283 | C27A2.2 | rpl-22 | ribosomal protein L22 | 67.24 | 160.6 | 4.40E-41 | 26 | 1.3 | 0 | 3.3 | 1 | 0 | 0.0% | | 4 | 4 | 46 |
| 284 | K02D10.5 | K02D10.5 | synaptosomal associat | 47.24 | 158.3 | 7.20E-40 | 26 | 1.7 | 0 | 4.2 | 1 | 0 | 0.0% | | 1 | 0 | 2 |
| 285 | W01G7.3 | W01G7.3 | RNA polymerases L / 1 | 75.56 | 156.4 | 7.20E-40 | 26 | 1 | 0 | 5.3 | 1.6 | 0 | 0.0% | | 12 | 10 | 0 |
| 286 | T26A5.9 | dlc-1 | Dynein light chain type | 94.59 | 176 | 5.90E-16 | 28 | 0 | 1 | 4.6 | 1.2 | 0 | 0.0% | | 7 | 7 | 22 |
| 287 | F55C5.8 | F55C5.8 | signal recognition partic | 45.45 | 141.4 | 2.30E-34 | 28 | 0.6 | 1 | 2.9 | 1 | 0 | 0.0% | | 0 | 0 | 0 |
| 288 | C14A4.14 | C14A4.14 | unknown function | 75 | 251.1 | 1.30E-67 | 31 | 2.6 | 0 | 1.6 | 0 | 0 | 0.0% | | 4 | 4 | 0 |
| 289 | B0035.11 | B0035.11 | Yeast LEO1 protein like | 55.88 | 75.9 | 1.00E-13 | 10 | 2.7 | 0 | 3.3 | 3.2 | 0 | 0.0% | | 1 | 0 | 1 |
| 290 | T10F2.4 | T10F2.4 | WD domain, G-beta re | 45.68 | 328.6 | 8.30E-91 | 35 | 0 | 2 | 4.3 | 0 | 0 | 0.0% | | 7 | 4 | 0 |
| 291 | W06E11.1 | W06E11.1 | Sin-like protein conserv | 41.46 | 72.4 | 1.00E-13 | 10 | 3.6 | 0 | 2 | 3 | 0.3 | 3.4% | | 1 | 0 | 0 |
| 292 | F57B10.1 | F57B10.1 | bZIP transcription facto | 73.33 | 70.9 | 1.40E-19 | 10 | 4.1 | 0 | 2.2 | 1.6 | 1 | 11.2% | | 1 | 1 | 10 |
| 293 | K09H9.6 | lpd-6 | Brix domain;Brix | 51.2 | 197.6 | 2.50E-51 | 34 | 3.9 | 0 | 0 | 2 | 0 | 0.0% | | 1 | 0 | 0 |
| 294 | M04B2.1 | mep-1 | zinc-finger protein | 73.81 | 97.1 | 3.40E-20 | 15 | 2 | 0 | 1 | 1.6 | 0.3 | 6.1% | | 1 | 0 | 0 |
| 295 | C53A5.1 | C53A5.1 | unknown function | 57.14 | 75.48 | 2.10E-15 | 33 | 1.3 | 0 | 1.6 | 1 | 0 | 0.0% | | 3 | 2 | 0 |
| 296 | Y71F9AM.4 | Y71F9AM. | Sec34-like family;Sec3 | 52.31 | 95.52 | 1.90E-20 | 16 | 1.2 | 1 | 2 | 2.2 | 0 | 0.0% | | 1 | 0 | 7 |
| 297 | T05H4.12 | T05H4.12 | Mitochondrial ATP synt | 34.62 | 72.79 | 1.20E-14 | 26 | 1 | 0 | 2.6 | 1 | 0 | 0.0% | | 18 | 17 | 7 |
| 298 | H43I07.2 | H43I07.2 | RNA polymerase Rpb3 | 39.83 | 85.5 | 3.80E-17 | 15 | 2.6 | 0 | 1 | 1 | 0 | 0.0% | | 1 | 1 | 1 |
| 299 | F57H12.1 | arf-3 | GTP-binding protein | 87.57 | 319.3 | 1.30E-88 | 3 | 2.3 | 1 | 2.2 | 2.6 | 0 | 0.0% | | 2 | 2 | 39 |
| 300 | C32F10.5 | hmg-3 | single-strand recognitic | 54.55 | 145.2 | 8.50E-35 | 10 | 3.2 | 0 | 3.6 | 1 | 0 | 0.0% | | 19 | 17 | 1 |

FIG. 3D

IDENTIFICATION AND USE OF TARGET GENES FOR CONTROL OF PLANT PARASITIC NEMATODES

This application is a continuation of U.S. application Ser. No. 14/011,647, filed Aug. 27, 2013, which is a divisional of U.S. application Ser. No. 11/673,351, filed Feb. 9, 2007 (now U.S. Pat. No. 8,519,225), which claims the benefit of and priority to U.S. Provisional Application Ser. No. 60/772,265, filed Feb. 10, 2006. The present application is also a continuation-in-part of U.S. application Ser. No. 13/374,480, filed Dec. 29, 2011, which is a continuation of U.S. application Ser. No. 11/360,355, filed Feb. 23, 2006 (now U.S. Pat. No. 8,088,976), which claims the benefit of priority of U.S. Provisional Application Ser. No. 60/655,875, filed Feb. 24, 2005, all of the disclosures of which are incorporated herein by reference in their entireties.

BACKGROUND OF THE INVENTION

1. Field of the Invention

The present invention relates generally to genetic control of plant disease caused by plant-parasitic nematodes. More specifically, the present invention relates to identification of target coding sequences, and to use of recombinant DNA technologies for post-transcriptionally repressing or inhibiting expression of target coding sequences in the cells of a plant-parasitic nematode to provide a plant protective effect.

2. Description of Related Art

Plants are subject to multiple potential disease causing agents, including plant-parasitic nematodes, which are active, flexible, elongate, organisms that live on moist surfaces or in liquid environments, including films of water within soil and moist tissues within other organisms. There are numerous plant-parasitic nematode species, including various cyst nematodes (e.g. *Heterodera* sp.), root knot nematodes (e.g. *Meloidogyne* sp.), lesion nematodes (e.g. *Pratylenchus* sp.), dagger nematodes (e.g. *Xiphinema* sp.) and stem and bulb nematodes (e.g. *Ditylenchus* sp.), among others. Tylenchid nematodes (members of the order Tylenchida), including the families Heteroderidae, Meloidogynidae, and Pratylenchidae, are the largest and most economically important group of plant-parasitic nematodes. Other important plant-parasitic nematodes include Dorylaimid nematodes (e.g. *Xiphinema* sp.), among others. Nematode species grow through a series of lifecycle stages and molts. Typically, there are five stages and four molts: egg stage; J1 (i.e. first juvenile stage); M1 (i.e. first molt); J2 (second juvenile stage; sometimes hatch from egg); M2; J3; M3; J4; M4; A (adult). Juvenile ("J") stages are also sometimes referred to as larval ("L") stages. Gene expression may be specific to one or more lifecycle stages.

Some species of nematodes have evolved as very successful parasites of both plants and animals and are responsible for significant economic losses in agriculture and livestock and for morbidity and mortality in humans. Nematode parasites of plants can inhabit all parts of plants, including roots, developing flower buds, leaves, and stems. Plant parasites are classified on the basis of their feeding habits into the broad categories migratory ectoparasites, migratory endoparasites, and sedentary endoparasites. Sedentary endoparasites, which include the root knot nematodes (*Meloidogyne*) and cyst nematodes (*Globodera* and *Heterodera*) induce feeding sites ("syncytia") and establish long-term infections within roots that are often very damaging to crops. It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al., 1994).

Compositions, methods, and agents for controlling infestations by nematodes have been provided in several forms. Biological and cultural control methods, including plant quarantines, have been attempted in numerous instances. In some crops, plant resistance genes have been identified that allow nematode resistance or tolerance. Chemical compositions such as nematocides have typically been applied to soil in which plant parasitic nematodes are present. However, there is an urgent need for safe and effective nematode controls. Factors relating to the disadvantages of current control strategies include heightened concern for the sustainability of agriculture, and new government regulations that may prevent or severely restrict the use of many available agricultural chemical antihelminthic agents.

Chemical agents are often not selective, and exert their effects on non-target organisms, effectively disrupting populations of beneficial microorganisms, for a period of time following application of the agent. Chemical agents may persist in the environment and only be slowly metabolized. Nematocidal soil fumigants such as chloropicrin and methyl bromide and related compounds are highly toxic, and methyl bromide has been identified as an ozone-depleting compound. Thus its registration for use in the United States is not being renewed. These agents may also accumulate in the water table or the food chain, and in higher trophic level species. These agents may also act as mutagens and/or carcinogens to cause irreversible and deleterious genetic modifications. Thus, alternative methods for nematode control, such as genetic methods, are increasingly being studied.

The organism *Caenorhabditis elegans*, a bacteriovorous nematode, is the most widely studied nematode genetic model. Public and private databases hold a wealth of information on its genetics and development, but practically applying this information for control of plant-parasitic nematodes remains a challenge (McCarter et al. 2003; McCarter 2004). It has previously been impractical to routinely identify a large number of target genes in nematodes other than *C. elegans*, such as plant-parasitic nematodes, for subsequent functional analysis e.g. by RNAi analysis. Therefore, there has existed a need for improved methods of identifying target genes, suppression of expression of which leads to control of nematode infestation.

Many genes in *C. elegans* have orthologs in metazoan animals including insects and vertebrates as well as other nematodes. In recent years, a greatly expanded expressed sequence tag (EST) collection has been generated from over 30 parasitic nematode species of plants and animals (Parkinson et al., 2004). As of 2005 there were approximately 560,874 nucleotide sequences in Genbank from nematodes other than *Caenorhabditis* species and public projects are underway to generate draft sequences of *Meloidogyne hapla* (root knot nematode), *Haemonchus contortus* (parasite of sheep), *Trichinella spiralis* (parasite of humans and other mammals) (430,000 sequence traces submitted), and *Pristionchus pacificus* (free living nematode) (149,000 sequence traces submitted). 20,109 ESTs are available from *Heterodera glycines* representing portions of approximately 9,000 genes (see, e.g., U.S. patent application Ser. No. 11/360,355, filed Feb. 23, 2006). Conserved genes are expected to often retain the same or very similar functions in different nematodes. This functional equivalence has been demonstrated in some cases by transforming *C. elegans* with homologous genes from other nematodes (Kwa et al., 1995; Redmond et al. 2001). Such equivalence has been shown in cross phyla comparisons for conserved genes and is expected to be more robust among species within a phylum.

RNA interference (RNAi) is a process utilizing endogenous cellular pathways whereby a double stranded RNA (dsRNA) specific target gene results in the degradation of the mRNA of interest. In recent years, RNAi has been used to perform gene "knockdown" in a number of species and experimental systems, from the nematode C. elegans, to plants, to insect embryos and cells in tissue culture (Fire et al., 1998; Martinez et al., 2002; McManus and Sharp, 2002). RNAi works through an endogenous pathway including the Dicer protein complex that generates ~21-nucleotide small interfering RNAs (siRNAs) from the original dsRNA and the RNA-induced silencing complex (RISC) that uses siRNA guides to recognize and degrade the corresponding mRNAs. Only transcripts complementary to the siRNA are cleaved and degraded, and thus the knock-down of mRNA expression is usually sequence specific. The gene silencing effect of RNAi persists for days and, under experimental conditions, can lead to a decline in abundance of the targeted transcript of 90% or more, with consequent decline in levels of the corresponding protein.

dsRNA-mediated gene suppression by RNAi can be achieved in C. elegans by feeding, by soaking the nematodes in solutions containing double stranded or small interfering RNA molecules, and by injection of the dsRNA molecules (Kamath et al., 2001; Maeda et al., 2001. Several large-scale surveys of C. elegans genes by RNAi have been performed so that RNAi knockdown information is available for >90% of C. elegans genes (Gonczy et al., 2000; Fraser et al., 2000; Piano et al., 2000; Maeda et al., 2001; Kamath et al., 2003; Simmer et al., 2003; Ashrafi et al., 2003; Sonnichsen et al., 2005).

To date, only limited published technical or patent information exists on RNAi-mediated gene suppression in plant parasitic nematodes, wherein the double-stranded (dsRNA) or small interfering (siRNA) molecules are taken up from artificial growth media (in vitro) or from plant tissue (in planta). RNAi has been observed to function in several parasitic nematodes including the plant parasites *Heterodera glycines* and *Globodera pallida* (Urwin et al., 2002; US Publication US2004/0098761; US Publication US2003/0150017; US Publication US2003/0061626; US Publication US2004/0133943; Fairbairn et al. 2005), *Meloidogyne javanica* (WO2005/019408), and the mammalian parasites *Nippostrongylus brasiliensis* (Hussein et al., 2002), *Brugia malayi* (Aboobaker et al., 2003), and *Onchocerca volvulus* (Lustigman et al., 2004). Production of parasite-specific dsRNA in plant cells has been suggested as a direct strategy for control of plant parasitic nematodes including the soybean cyst nematode, *Heterodera glycines* (e.g. Fire et al., 1998; US Publication US2004/0098761; WO 03/052110 A2; US Publication US2005/0188438). US Publication US2006/0037101 describes use of *H. glycines* sequences, such as from pas5, to modulate SCN gene expression. However, no systematic method for identifying target nematode genes for use in such strategies has been reported, and only a limited number of plant-parasitic nematode genes have been proposed as potential targets for RNAi-mediated gene suppression studies.

BRIEF DESCRIPTION OF THE FIGURES

FIG. 1: *C. elegans* RNAi Phenotype Ranking System
FIG. 2: Results of *C. elegans* P0 RNAi feeding studies
FIG. 3A-3D: Top 300 List of *H. glycines* Gene Targets Based on *C. elegans* orthologs

SUMMARY OF THE INVENTION

The present invention is directed toward compositions and methods for controlling diseases caused by plant-parasitic nematodes. The present invention provides exemplary nucleic acid compositions that are homologous to at least a portion of one or more native nucleic acid sequences in a target plant-parasitic nematode. In certain embodiments, the nematode is selected from *Heterodera* sp., *Meloidogyne* sp., *Globodera* sp., *Helicotylenchus* sp., *Ditylenchus* sp., *Pratylenchus* sp., *Paratylenchus* sp., *Rotylenchus* sp., *Tylenchulus* sp., *Tylenchorhynchus* sp., *Hoplolaimus* sp., *Belonolaimus* sp., *Anguina* sp., *Subanguina* sp. and *Nacobbus* sp. In particular, the nematode may be a *Heterodera* sp., such as *H. glycines*. Specific examples of such nucleic acids provided by the invention are given in the attached sequence listing as SEQ ID NOs:301-1026, SEQ ID NOs:1269-1702, and SEQ ID NOs:1920-1929. However, in certain embodiments, the invention does not comprise SEQ ID NOs:525, 569, 797, 1293 or 1516.

Thus, in one aspect, the invention provides an isolated polynucleotide selected from the group consisting of: (a) a fragment of at least 21 contiguous nucleotides of a nucleic acid sequence of any of SEQ ID NOs:301-1026, SEQ ID NOs:1269-1702, and SEQ ID NOs:1920-1929, as set forth in the sequence listing, wherein uptake by a plant-parasitic nematode of a double stranded ribonucleotide sequence comprising at least one strand that is complementary to said fragment inhibits the growth of said nematode; and (b) a complement of the sequence of (a). In another aspect, the invention provides this isolated polynucleotide, further defined as operably linked to a heterologous promoter. However, in certain embodiments, the invention does not comprise SEQ ID NOs:525, 569, 797, 1293 or 1516. In yet another aspect, the invention provides this isolated polynucleotide further defined as comprised on a plant transformation vector. As used herein uptake by a plant-parasitic nematode includes ingestion of one or more sequences by the nematode, for example, by feeding. In specific non-limiting embodiments, uptake may be achieved by contacting a plant-parasitic nematode with a composition comprising one or more nucleic acid(s) according to the invention. For instance, uptake may also be achieved by soaking of plant-parasitic nematodes with a solution comprising the nucleic acid(s).

The invention is also directed to a double stranded ribonucleotide sequence produced from the expression of the above polynucleotide, wherein the taking up of said ribonucleotide sequence by a plant-parasitic nematode inhibits the growth of said nematode. The invention further provides a double stranded ribonucleotide sequence produced by preparing a recombinant polynucleotide sequence comprising a first, a second and a third polynucleotide sequence, wherein the first polynucleotide sequence comprises an isolated polynucleotide, uptake of which by a plant-parasitic nematode inhibits the growth, feeding, or development of said nematode, wherein the third polynucleotide sequence is linked to the first polynucleotide sequence by the second polynucleotide sequence, and wherein the third polynucleotide sequence is substantially the reverse complement of the first polynucleotide sequence such that the first and the third polynucleotide sequences hybridize when transcribed into a ribonucleic acid to form the double stranded ribonucleotide molecule stabilized by the linked second ribonucleotide sequence. Inhibition of nematode growth, feeding, or development may be accomplished by inhibiting expression of a nucleotide sequence in the plant-parasitic nematode that is substantially complementary to the sequence of the first polynucleotide.

The invention further provides a plant transformation vector comprising the above mentioned nucleotide sequence, wherein the sequence is operably linked to a heterologous promoter functional in a plant cell, and to cells transformed with the vector. The cells may be prokaryotic or eukaryotic. In particular, they may be plant cells. Plants and seeds derived from such transformed plant cells are also contemplated. The invention further provides a commodity product produced from such a plant, wherein said commodity product comprises a detectable amount of the polynucleotide of claim 1 or a ribonucleotide expressed therefrom. Methods to produce such a commodity product are also contemplated, by obtaining such transformed plants and preparing food or feed from them. In particular, the food or feed is defined as oil, meal, protein, starch, flour or silage.

The invention also relates to methods for controlling a population of a plant-parasitic nematode, such as *H. glycines*, comprising providing an agent comprising a double stranded ribonucleotide sequence that functions upon being taken up by the nematode to inhibit a biological function within said nematode, wherein the agent comprises a nucleotide sequence selected from the group consisting of SEQ ID NOs:301-1026, SEQ ID NOs:1269-1702, and SEQ ID NOs:1920-1929, and complements thereof. However, in certain embodiments, the invention does not relate to use of SEQ ID NOs:525, 569, 797, 1293 or 1516. The polynucleotide sequence may exhibit from about 95 to about 100% nucleotide sequence identity along at least from about 19 to about 25 contiguous nucleotides to a target coding sequence derived from said nematode. The target sequence may encode a protein, the predicted function of which is selected from the group consisting of: DNA replication, cell cycle control, transcription, RNA processing, translation, ribosome function, tRNA synthesis, tRNA function, protein trafficking, secretion, protein modification, protein stability, protein degradation, energy production, mitochondrial function, intermediary metabolism, cell structure, signal transduction, endocytosis, ion regulation and transport.

The invention further provides a method for reducing the number of *Heterodera* feeding sites established in the root tissue of a host plant, comprising providing in the host plant of a *Heterodera* sp. a transformed plant cell expressing a polynucleotide sequence of any of SEQ ID NOs:301-1026, SEQ ID NOs:1269-1702, and SEQ ID NOs:1920-1929, wherein the polynucleotide is expressed to produce a double stranded ribonucleic acid that functions upon being taken up by the *Heterodera* sp. to inhibit the expression of a target sequence within said nematode and results in a decrease in the number of feeding sites established, relative to growth on a host lacking the transformed plant cell.

The present invention also relates to a method for improving the yield of a crop produced from a crop plant subjected to plant-parasitic nematode infection, said method comprising the steps of: a) introducing a polynucleotide selected from SEQ ID NOs:301-1026, SEQ ID NOs:1269-1702, and SEQ ID NOs:1920-1929, into said crop plant; b) cultivating the crop plant to allow the expression of said polynucleotide, wherein expression of the polynucleotide inhibits plant-parasitic nematode infection or growth and loss of yield due to plant-parasitic nematode infection. However, in certain embodiments, the invention does not comprise use of a polynucleotide selected from the group consisting of SEQ ID NOs:525, 569, 797, 1293 or 1516. In particular, the crop plant may be soybean (*Glycine max*), and the plant-parasitic nematode is a Tylenchid nematode such as *H. glycines*.

The invention additionally provides a method for modulating the expression of a target gene in a plant-parasitic nematode cell, the method comprising: (a) transforming a plant cell with a vector comprising a nucleic acid sequence encoding a dsRNA selected from the group consisting of SEQ ID NOs:301-1026, SEQ ID NOs:1269-1702, and SEQ ID NOs:1920-1929, operatively linked to a promoter and a transcription termination sequence; (b) culturing the transformed plant cell under conditions sufficient to allow for development of a plant cell culture comprising a plurality of transformed plant cells; (c) selecting for transformed plant cells that have integrated the nucleic acid sequence into their genomes; (d) screening the transformed plant cells for expression of the dsRNA encoded by the nucleic acid sequence; and (e) selecting a plant cell that expresses the dsRNA. However, in certain embodiments, the invention does not relate to use of SEQ ID NOs:525, 569, 797, 1293 or 1516. Plants may also be regenerated from such plant cells. In particular, "modulating expression" may comprise inhibiting expression.

The invention also contemplates a method of identifying genes likely to be essential in the lifecycle of a target nematode, comprising: (a) ranking a *Caenorhabditis elegans* gene according to one or more criteria selected from the group consisting of: potency of reported RNAi phenotype; level of confidence in the reported phenotype; and likelihood of effect of RNAi at multiple stages in a nematode's lifecycle, such that a phenotype score is obtained, wherein a high rank indicates a *C. elegans* gene with a higher likelihood of demonstrating a detectable RNAi phenotype compared to the likelihood of such a phenotype in a lower ranked gene; (b) identifying possible orthologs of a *C. elegans* gene in the genome of the target nematode by performing a sequence similarity search in a protein or nucleic acid database such that a protein or nucleic acid sequence from a nematode other than *C. elegans* that has a threshold BLAST e-value of $e^{-10}$ when compared with a *C. elegans* sequence is deemed a possible ortholog of the *C. elegans* sequence; (c) identifying, among the possible orthologs of step (b), those genes from a nematode other than *C. elegans* that demonstrate a phenotype score in step (a) among the top 3.5% of all *C. elegans* genes. However, in certain embodiments, the invention does not comprise identification of SEQ ID NOs:525, 569, 797, 1293 or 1516.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention.

The present invention provides methods and compositions for genetic control of plant-parasitic nematode infestations. Methods for identifying genes essential to the lifecycle of a plant-parasitic nematode for use as a target for dsRNA-mediated control of a nematode population are also provided. DNA plasmid vectors encoding dsRNA molecules are designed to suppress nematode genes essential for growth and development. For example, the present invention provides methods and recombinant DNA technologies for post-transcriptionally repressing or inhibiting expression of a target coding sequence in a plant-parasitic nematode to provide a protective effect by allowing the plant-parasitic nematode to ingest one or more double stranded or small interfering ribonucleic acid (RNA) molecules transcribed from all or a portion of a target coding sequence, thereby controlling the infection. Therefore, the present invention relates to sequence-specific inhibition of expression of coding sequences using double-stranded RNA (dsRNA), including small interfering RNA (siRNA), to achieve the intended levels of nematode control.

In another aspect, the invention provides a method for evaluating the likelihood that a gene is useful as a target for dsRNA-mediated gene suppression for the purpose of controlling a nematode population. One challenge of achieving parasite control via RNAi is the selection of appropriate gene targets which will result in the disruption of the parasite's lifecycle following transcript knockdown. Since the throughput of systems to test candidate genes in *Heterodera glycines* is limited, prioritization of targets prior to testing is important. RNAi-based functional genomic screens are highly effective filters that can narrow target choices by an order of magnitude or more. In certain embodiments the nematode is a plant parasitic nematode. In another embodiment, the nematode is a Tylenchid plant-parasitic nematode. In another embodiment the nematode is a *Heterodera* sp. In yet another embodiment, the nematode is the soybean cyst nematode (*Heterodera glycines*).

A method for inhibiting target gene function within the plant pathogen soybean cyst nematode, *Heterodera glycines*, is also provided by the present invention, and can be accomplished by RNA interference, resulting in disruption of the pathogen's lifecycle. Optimal target genes for disruption include life-cycle essential genes where disruption results in high penetrance death of the parasite populations or "genetic death" by blocking of reproduction with minimal feeding damage to the plant, reduction in number of established feeding sites, and minimal viable escaping worms reaching the next generation. Another aspect of the present invention provides the nucleic acids of each of the 300 target genes predicted to be essential to *H. glycines* growth and/or development (FIG. 3). Features used to predict such targets include orthology to known *C. elegans* genes with strong and reproducible RNA interference phenotypes, and expression pattern in *H. glycines.*

In yet another aspect of the present invention, a set of isolated and purified nucleotide sequences as set forth in SEQ ID NOs:301-1026, SEQ ID NOs:1269-1702, and SEQ ID NOs:1920-1929, is provided. However, in certain embodiments, the invention does not comprise SEQ ID NOs:525, 569, 797, 1293 or 1516. The present invention provides a stabilized dsRNA molecule for the expression of one or more RNAs for inhibition of expression of a target gene in a plant-parasitic nematode, expressed from these sequences and fragments thereof. A stabilized dsRNA, including a dsRNA or siRNA molecule can comprise at least two coding sequences that are arranged in a sense and an antisense orientation relative to at least one promoter, wherein the nucleotide sequence that comprises a sense strand and an antisense strand are linked or connected by a spacer sequence of at least from about five to about one thousand nucleotides, wherein the sense strand and the antisense strand may be a different length, and wherein each of the two coding sequences shares at least 80% sequence identity, at least 90%, at least 95%, at least 98%, or 100% sequence identity, to any one or more nucleotide sequence(s) set forth in SEQ ID NOs:301-1026, SEQ ID NOs:1269-1702, and SEQ ID NOs:1920-1929.

In yet another aspect, the invention provides recombinant DNA constructs comprising a nucleic acid molecule encoding a dsRNA molecule described herein. The dsRNA may be formed by transcription of one strand of the dsRNA molecule from a nucleotide sequence which is at least from about 80% to about 100% identical to a nucleotide sequence selected from the group consisting of SEQ ID NOs:301-1026, SEQ ID NOs:1269-1702, and SEQ ID NOs:1920-1929. Such recombinant DNA constructs may be defined as producing dsRNA molecules capable of inhibiting the expression of endogenous target gene(s) in a plant-parasitic nematode cell upon ingestion. The construct may comprise a nucleotide sequence of the invention operably linked to a promoter sequence that functions in the host cell such as a plant cell. Such a promoter may be tissue-specific and may, for example, be specific to a tissue type which is the subject of plant-parasitic nematode attack. In the case of a root or foliar pathogen, respectively for example, it may be desired to use a promoter providing root or leaf-preferred expression, respectively.

Nucleic acid constructs in accordance with the invention may comprise at least one non-naturally occurring nucleotide sequence that can be transcribed into a single stranded RNA capable of forming a dsRNA molecule in vivo through intermolecular hybridization. Such dsRNA sequences self assemble and can be provided in the nutrition source of a plant-parasitic nematode to achieve the desired inhibition.

A recombinant DNA construct may comprise two different non-naturally occurring sequences which, when expressed in vivo as dsRNA sequences and provided in the tissues of the host plant of a plant-parasitic nematode, inhibit the expression of at least two different target genes in the plant-parasitic nematode. In certain embodiments, at least 2, 3, 4, 5, 6, 8 or 10 or more different dsRNAs are produced in a cell, or plant comprising the cell, that have a nematode-inhibitory effect. The dsRNAs may be expressed from multiple constructs introduced in different transformation events or could be introduced on a single nucleic acid molecule. The dsRNAs may be expressed using a single promoter or multiple promoters. In one embodiment of the invention, single dsRNAs are produced that comprise nucleic acids homologous to multiple loci within a plant-parasitic nematode.

In still yet another aspect, the invention provides a recombinant host cell having in its genome at least one recombinant DNA sequence that is transcribed to produce at least one dsRNA molecule that functions when ingested by a plant-parasitic nematode to inhibit the expression of a target gene in the nematode. The dsRNA molecule may be encoded by any of the nucleic acids described herein and as set forth in the sequence listing. The present invention also provides a transformed plant cell having in its genome at least one recombinant DNA sequence described herein. Transgenic plants comprising such a transformed plant cell are also provided, including progeny plants of any generation, seeds, and plant products, each comprising the recombinant DNA. The dsRNA molecules of the present invention may be found in the transgenic plant cell, for instance in the cytoplasm. They may also be found in an apoplastic space.

The invention also provides one or more stabilization sequences, or "clamps", which may be unrelated to the gene of interest. A clamp preferably comprises a GC rich region that serves to thermodynamically stabilize the dsRNA molecule, and may increase gene silencing.

Further provided by the invention is a fragment of a nucleic acid sequence selected from the group consisting of SEQ ID NOs:301-1026, SEQ ID NOs:1269-1702, and SEQ ID NOs:1920-1929. The fragment may be defined as causing the death, growth inhibition, or cessation of infection or feeding by a plant-parasitic nematode, when expressed as a dsRNA and taken up by the nematode. The fragment may, for example, comprise at least about 19, 21, 23, 25, 40, 60, 80, 100, 125 or more contiguous nucleotides of any one or more of the sequences in SEQ ID NOs:301-1026, SEQ ID NOs:1269-1702, and SEQ ID NOs:1920-1929, or a complement thereof. However, in certain embodiments, the invention does not comprise a fragment or complement of SEQ ID NOs:525, 569, 797, 1293 or 1516. One beneficial DNA segment for use in the present invention is at least from about 19 to about 23, or about 23 to about 100 nucleotides, but less than about 2000 nucleotides, in length. Particularly useful will be dsRNA sequences including about 23 to about 300 nucleotides homologous to a nematode target sequence. The invention also provides a ribonucleic acid expressed from any of such sequences including a dsRNA. A sequence selected for use in expression of a gene suppression agent can be constructed from a single sequence derived from one or more target plant-parasitic nematode species and intended for use in expression of an RNA that functions in the suppression of a single gene or gene family in the one or more target pathogens, or that the DNA sequence can be constructed as a chimera from a plurality of DNA sequences.

In another embodiment, the invention provides a method for modulating expression of a target gene in a nematode cell, the method comprising: (a) transforming a plant cell with a vector comprising a nucleic acid sequence encoding a dsRNA operatively linked to a promoter and a transcription termination sequence; (b) culturing the transformed plant cell under conditions sufficient to allow for development of a plant cell culture comprising a plurality of transformed plant cells; (c) selecting for transformed plant cells that have integrated the vector into their genomes; (d) screening the transformed plant cells for expression of the dsRNA encoded by the vector; (e) selecting a plant cell that expresses the dsRNA; (f) optionally regenerating a plant from the plant cell that expresses the dsRNA; whereby expression of the gene in the plant is sufficient to modulate the expression of a target gene in a cell of a plant parasitic nematode that contacts the transformed plant or plant cell. Modulation of gene expression may include partial or complete suppression of such expression.

In yet another aspect, the invention provides a method for suppression of gene expression in a plant-parasitic nematode, comprising the provision in the tissue of the host of the nematode a gene-suppressive amount of at least one dsRNA molecule transcribed from a nucleotide sequence as described herein, at least one segment of which is complementary to an mRNA sequence within the cells of the plant-parasitic nematode. The method may further comprise observing the death or growth inhibition of the plant-parasitic nematode, and the degree of host symptomatology. A dsRNA molecule, including its modified form such as an siRNA molecule, ingested by a pathogenic microorganism in accordance with the invention may be at least from about 80, 81, 82, 83, 84, 85, 86, 87, 88 89, 90, 91, 92, 93, 94, 95, 96, 97, 98, 99, or about 100% identical to a RNA molecule transcribed from a nucleotide sequence selected from the group consisting of SEQ ID NOs:301-1026, SEQ ID NOs: 1269-1702, and SEQ ID NOs:1920-1929.

Isolated and substantially purified nucleic acid molecules including, but not limited to, non-naturally occurring nucleotide sequences and recombinant DNA constructs for transcribing dsRNA molecules of the present invention are therefore provided, which suppress or inhibit the expression of an endogenous coding sequence or a target coding sequence in the plant-parasitic nematode when introduced thereto. Transgenic plants that (a) contain nucleotide sequences encoding the isolated and substantially purified nucleic acid molecules and the non-naturally occurring recombinant DNA constructs for transcribing the dsRNA molecules for controlling plant-parasitic nematode infections, and (b) display resistance and/or enhanced tolerance to the infections, are also contemplated. Compositions containing the dsRNA nucleotide sequences of the present invention for use in topical applications onto plants or onto animals or into the environment of an animal to achieve the elimination or reduction of plant-parasitic nematode infection are also included.

cDNA sequences encoding proteins or parts of proteins essential for survival, such as amino acid sequences involved in various metabolic or catabolic biochemical pathways, cell division, reproduction, energy metabolism, digestion, and the like may be selected for use in preparing double stranded RNA molecules to be provided in the host plant of a plant-parasitic nematode. As described herein, ingestion of compositions by a target organism containing one or more dsRNAs, at least one segment of which corresponds to at least a substantially identical segment of RNA produced in the cells of the target pathogen, can result in the death or other inhibition of the target. These results indicate that a nucleotide sequence, either DNA or RNA, derived from a plant-parasitic nematode can be used to construct plant cells resistant to infestation by the nematode. The host plant of the nematode, for example, can be transformed to contain one or more of the nucleotide sequences derived from the nematode as provided herein. The nucleotide sequence transformed into the host may encode one or more RNAs that form into a dsRNA sequence in the cells or biological fluids within the transformed host, thus making the dsRNA available if/when the plant-parasitic nematode forms a nutritional relationship with the transgenic host. This may result in the suppression of expression of one or more genes in the cells of the plant-parasitic nematode and ultimately death or inhibition of its growth or development.

The present invention relates generally to genetic control of plant-parasitic nematodes in host organisms. More particularly, the present invention includes methods for delivery of nematode control agents to plant-parasitic nematodes. Such control agents cause, directly or indirectly, an impairment in the ability of the plant-parasitic nematode to feed, grow or otherwise cause disease in a target host. The present invention provides in one embodiment a method comprising delivery of stabilized dsRNA molecules to plant-parasitic nematodes as a means for suppression of targeted genes in the plant-parasitic nematode, thus achieving desired control of plant disease in the nematode host.

In accomplishing the foregoing, the present invention provides a method of inhibiting expression of a target gene in a plant-parasitic nematode, resulting in the cessation of growth, development, reproduction, and/or feeding, and eventually may result in the death of the plant-parasitic nematode. The method comprises in one embodiment introducing partial or fully stabilized double-stranded RNA (dsRNA) nucleotide molecules, including its modified forms such as small interfering RNA (siRNA) sequences, into a nutritional composition for the plant-parasitic nematode, and making the nutritional composition or food source available to the plant-parasitic nematode. Ingestion of the nutritional composition containing the double stranded or siRNA molecules results in the uptake of the molecules by the cells of the nematode, resulting in the inhibition of expression of at least one target gene in the cells of the nematode Inhibition of the target gene exerts a deleterious effect upon the nematode. The methods and associated compositions may be used for limiting or eliminating infection or parasitization of a plant or plant cell by a nematode, in or on any host tissue or environment in which a the nematode is present by providing one or more compositions comprising the dsRNA molecules described herein in the host of the nematode.

In certain embodiments, dsRNA molecules provided by the invention comprise nucleotide sequences complementary to a sequence as set forth in any of SEQ ID NOs:301-1026, SEQ ID NOs:1269-1702, and SEQ ID NOs:1920-1929, the inhibition of which in a plant-parasitic nematode results in the reduction or removal of a protein or nucleotide sequence agent that is essential for the nematode's growth and development or other biological function. The nucleotide sequence selected may exhibit from about 80% to about 100% sequence identity to one of the nucleotide sequences as set forth in SEQ ID NOs:301-1026, SEQ ID NOs:1269-1702, and SEQ ID NOs:1920-1929, including the complement thereof. However, in certain embodiments, the invention does not comprise a sequence that exhibits 80-100% identity to SEQ ID NOs:525, 569, 797, 1293 or 1516. Such inhibition can be described as specific in that a nucleotide sequence from a portion of the target gene is chosen from which the inhibitory dsRNA or siRNA is transcribed. The method is effective in inhibiting the expression of at least one target gene and can be used to inhibit many different types of target genes in the plant-parasitic nematode.

The sequences identified as having a nematode-protective effect may be readily expressed as dsRNA molecules through the creation of appropriate expression constructs. For example, such sequences can be expressed as a hairpin and stem and loop structure by taking a first segment corresponding to a sequence selected from SEQ ID NOs: 301-1026, SEQ ID NOs:1269-1702, and SEQ ID NOs:1920-1929, or a fragment thereof, linking this sequence to a second segment spacer region that is not homologous or complementary to the first segment, and linking this to a third segment that transcribes an RNA, wherein at least a portion of the third segment is substantially complementary to the first segment. Such a construct forms a stem and loop structure by hybridization of the first segment with the third segment and a loop structure forms comprising the second segment (WO94/01550, WO98/05770, US 2002/0048814A1, and US 2003/0018993A1. dsRNA may be generated for instance in the form of a double stranded structure such as a stem loop structure (e.g. hairpin), whereby production of siRNA targeted for a nematode sequence is enhanced by co-expression of a fragment of the targeted gene, for instance on an additional plant expressible cassette, that leads to enhanced siRNA production, or reduces methylation to prevent transcriptional gene silencing of the dsRNA hairpin promoter (e.g. WO05/019408).

The methods and compositions of the present invention may be applied to any monocot and dicot plant, depending on the pathogen (e.g. nematode) control desired. Examples of such plants include, without limitation, alfalfa, artichoke, asparagus, barley, beans, beet, broccoli, cabbage, canola, carrot, cassava, cauliflower, corn, cotton, cucumber, grape, oat, onion, pea, peanut, potato, rice, rye, sorghum, soybean, spinach, squash, sugarbeet, sugarcane, sunflower, tobacco, tomato, turfgrass, and wheat plants.

Exemplary plant-parasitic nematodes from which plants may be protected by the present invention, and their corresponding plants, include, but are not limited to: alfalfa: *Ditylenchus dipsaci, Meloidogyne hapla, Meloidogyne incognita, Meloidogyne javanica, Pratylenchus* spp., *Paratylenchus* spp., *Xiphinema* spp.; banana: *Radopholus similis, Helicotylenchus multicinctus, M. incognita, M. arenaria, M. javanica, Pratylenchus coffeae, Rotylenchulus reniformis*; beans and peas: *Meloidogyne* spp., *Heterodera* spp., *Belonolaimus* spp., *Helicotylenchus* spp., *Rotylenchulus reniformis, Paratrichodorus anemones, Trichodorus* spp.; cassava: *Rotylenchulus reniformis, Meloidogyne* spp.; cereals: *Anguina tritici* (Emmer, rye, spelt wheat), *Bidera avenae* (oat, wheat), *Ditylenchus dipsaci* (rye, oat), *Subanguina radicicola* (oat, barley, wheat, rye), *Meloidogyne naasi* (barley, wheat, rye), *Pratylenchus* spp. (oat, wheat, barley, rye), *Paratylenchus* spp. (wheat), *Tylenchorhynchus* spp. (wheat, oat); chickpea: *Heterodera cajani, Rotylenchulus reniformis, Hoplolaimus seinhorsti, Meloidogyne* spp., *Pratylenchus* spp.; citrus: *Tylenchulus semipenetrans, Radopholus similis, Radopholus citrophilus, Hemicycliophora arenaria, Pratylenchus* spp., *Meloidogyne* spp., *Bolonolaimus longicaudatus, Trichodorus* spp., *Paratrichodorus* spp., *Xiphinema* spp.; clover: *Meloidogyne* spp., *Heterodera trifolii*; corn: *Pratylenchus* spp., *Paratrichodorus minor, Longidorus* spp., *Hoplolaimus columbus*; cotton: *Meloidogyne incognita, Belonolaimus longicaudatus, Rotylenchulus reniformis, Hoplolaimus galeatus, Pratylenchus* spp., *Tylenchorhynchus* spp., *Paratrichodorus minor*; grapes: *Xiphinema* spp., *Pratylenchus vulnus, Meloidogyne* spp., *Tylenchulus semipenetrans, Rotylenchulus reniformis*; grasses: *Pratylenchus* spp., *Longidorus* spp., *Paratrichodorus christiei, Xiphinema* spp., *Ditylenchus* spp.; peanut: *Pratylenchus* spp., *Meloidogyne hapla., Meloidogyne arenaria, Criconemella* spp., *Belonolaimus longicaudatus*; pigeon pea: *Heterodera cajani, Rotylenchulus reniformis, Hoplolaimus seinhorsti, Meloidogyne* spp., *Pratylenchus* spp.; potato: *Globodera rostochiensis, Globodera pallida, Meloidogyne* spp., *Pratylenchus* spp., *Trichodorus primitivus, Ditylenchus* spp., *Paratrichodorus* spp., *Nacobbus aberrans*; rice: *Aphelenchoides besseyi, Ditylenchus angustus, Hirchmanniella* spp., *Heterodera oryzae, Meloidogyne* spp.; small fruits: *Meloidogyne* spp.; *Pratylenchus* spp., *Xiphinema* spp., *Longidorus* spp., *Paratrichodorus christiei, Aphelenchoides* spp.; soybean: *Heterodera glycines, Meloidogyne incognita, Meloidogyne javanica, Belonolaimus* spp., *Hoplolaimus columbus*; sugar beet: *Heterodera schachtii, Ditylenchus dipsaci, Meloidogyne* spp., *Nacobbus aberrans, Trichodorus* spp., *Longidorus* spp., *Paratrichodorus* spp.; sugar cane: *Meloidogyne* spp., *Pratylenchus* spp., *Radopholus* spp., *Heterodera* spp., *Hoplolaimus* spp., *Helicotylenchus* spp., *Scutellonema* spp., *Belonolaimus* spp., *Tylenchorhynchus* spp., *Xiphinema* spp., *Longidorus* spp., *Paratrichodorus* spp.; tobacco: *Meloidogyne* spp., *Pratylenchus* spp., *Tylenchorhynchus claytoni, Globodera tabacum, Trichodorus* spp., *Xiphinema americanum, Ditylenchus dipsaci, Paratrichodorus* spp.; and tomato: *Pratylenchus* spp., *Meloidogyne* spp.

The invention also provides combinations of methods and compositions for controlling infection by plant-parasitic nematodes. One means provides a dsRNA method as described herein for protecting plants from plant-parasitic nematodes along with one or more chemical agents that exhibit features different from those exhibited by the dsRNA methods and compositions, and can interfere with nematode growth or development.

A. Nucleic Acid Compositions and Constructs

The invention provides recombinant DNA constructs for use in achieving stable transformation of particular host targets. Transformed host targets may express effective levels of preferred dsRNA or siRNA molecules from the recombinant DNA constructs. Pairs of isolated and purified nucleotide sequences may be provided from cDNA library and/or genomic library information. The pairs of nucleotide sequences may be derived from any nematode for use as thermal amplification primers to generate the dsRNA and siRNA molecules of the present invention.

As used herein, the term "nucleic acid" refers to a single or double-stranded polymer of deoxyribonucleotide or ribonucleotide bases read from the 5' to the 3' end. The "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA) and the term "deoxyribonucleic acid" (DNA) is inclusive of cDNA and genomic DNA and DNA-RNA hybrids. The words "nucleic acid segment", "nucleotide sequence segment", or more generally "segment" will be understood by those in the art as a functional term that includes both genomic sequences, ribosomal RNA sequences, transfer RNA sequences, messenger RNA sequences, operon sequences and smaller engineered nucleotide sequences that express or may be adapted to express, proteins, polypeptides or peptides.

Provided according to the invention are nucleotide sequences, the expression of which results in an RNA sequence which is substantially homologous to all or part of an RNA molecule of a targeted gene in a plant-parasitic nematode that comprises an RNA sequence encoded by a nucleotide sequence within the genome of the nematode. Thus, after ingestion of the stabilized RNA sequence downregulation of the nucleotide sequence of the target gene in the cells of the plant-parasitic nematode may be obtained resulting in a deleterious effect on the growth, viability, proliferation, or reproduction of the nematode.

As used herein, the term "substantially homologous" or "substantial homology", with reference to a nucleic acid sequence, includes a nucleotide sequence that hybridizes under stringent conditions to the coding sequence of any of SEQ ID NOs:301-1026, SEQ ID NOs:1269-1702, and SEQ ID NOs:1920-1929, as set forth in the sequence listing, or the complements thereof. Sequences that hybridize under stringent conditions to any of SEQ ID NOs:301-1026, SEQ ID NOs:1269-1702, and SEQ ID NOs:1920-1929, or the complements thereof, are those that allow an antiparallel alignment to take place between the two sequences, and the two sequences are then able, under stringent conditions, to form hydrogen bonds with corresponding bases on the opposite strand to form a duplex molecule that is sufficiently stable under the stringent conditions to be detectable using methods well known in the art. Substantially homologous sequences have preferably from about 70% to about 80% sequence identity, or more preferably from about 80% to about 85% sequence identity, or most preferable from about 90% to about 95% sequence identity, to about 99% sequence identity, to the referent nucleotide sequences as set forth in any of SEQ ID NOs:301-1026, SEQ ID NOs:1269-1702, and SEQ ID NOs:1920-1929, in the sequence listing, or the complements thereof.

As used herein, the term "ortholog" refers to a gene in two or more species that has evolved from a common ancestral nucleotide sequence, and may retain the same function in the two or more species.

As used herein, the term "sequence identity", "sequence similarity" or "homology" is used to describe sequence relationships between two or more nucleotide sequences. The percentage of "sequence identity" between two sequences is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

As used herein, a "comparison window" refers to a conceptual segment of at least 6 contiguous positions, usually about 50 to about 100, more usually about 100 to about 150, in which a sequence is compared to a reference sequence of the same number of contiguous positions after the two sequences are optimally aligned. The comparison window may comprise additions or deletions (i.e. gaps) of about 20% or less as compared to the reference sequence (which does not comprise additions or deletions) for optimal alignment of the two sequences Those skilled in the art should refer to the detailed methods used for sequence alignment in the Wisconsin Genetics Software Package Release 7.0, Genetics Computer Group, 575 Science Drive Madison, Wis., USA) or refer to Ausubel et al. (1998) for a detailed discussion of sequence analysis.

The present invention provides DNA sequences capable of being expressed as an RNA in a cell or microorganism to inhibit target gene expression in a cell, tissue or organ of a plant-parasitic nematode. The sequences comprise a DNA molecule coding for one or more different nucleotide sequences, wherein each of the different nucleotide sequences comprises a sense nucleotide sequence and an antisense nucleotide sequence. The sequences may be connected by a spacer sequence coding for a dsRNA molecule of the present invention. The spacer sequence can constitute part of the sense nucleotide sequence or the antisense nucleotide sequence and forms within the dsRNA molecule between the sense and antisense sequences. The sense nucleotide sequence or the antisense nucleotide sequence is substantially identical to the nucleotide sequence of the target gene or a derivative thereof or a complementary sequence thereto. The dsDNA molecule may be placed operably under the control of a promoter sequence that functions in the cell, tissue or organ of the host expressing the dsDNA to produce dsRNA molecules. In one embodiment, the DNA sequence may be derived from a nucleotide sequence as set forth in SEQ ID NOs:301-1026, SEQ ID NOs:1269-1702, and SEQ ID NOs:1920-1929, in the sequence listing.

The invention also provides a DNA sequence for expression in a cell of a plant that, upon expression of the DNA to RNA and ingestion by a plant-parasitic nematode achieves suppression of a target gene in a cell, tissue or organ of a plant-parasitic nematode. The dsRNA may comprise one or multiple structural gene sequences, wherein each of the structural gene sequences comprises a sense nucleotide sequence and an antisense nucleotide sequence that may be connected by a spacer sequence that forms a loop within the complementary and antisense sequences. The sense nucleotide sequence or the antisense nucleotide sequence is substantially identical to the nucleotide sequence of the target gene, derivative thereof, or sequence complementary thereto. The one or more structural gene sequences may be placed operably under the control of one or more promoter sequences, at least one of which is operable in the cell, tissue or organ of a prokaryotic or eukaryotic organism, particularly a plant cell. Methods to express a gene suppression molecule in plants are known (e.g. WO06073727 A2; US Publication 2006/0200878 A1), and may be used to express a nucleotide sequence of the present invention.

A gene sequence or fragment for plant-parasitic nematode control according to the invention may be cloned between two tissue specific promoters, such as two root specific promoters which are operable in a transgenic plant cell and therein expressed to produce mRNA in the transgenic plant cell that form dsRNA molecules thereto. Examples of root specific promoters are known in the art (e.g. the nematode-induced RB7 promoter; U.S. Pat. No. 5,459,252; Opperman et al. 1994). The dsRNA molecules contained in plant tissues are ingested by a plant-parasitic nematode so that the intended suppression of the target gene expression is achieved.

The cauliflower mosaic virus 35S promoter, an archetypal strong promoter common in transgenic plant applications, or a related promoter such as the E35S or the FMV promoter, may be employed for driving nematode resistance genes, particularly for cyst nematodes (see Example 8). Promoters have also been identified that direct gene expression at nematode-induced feeding structures within a plant (e.g. Gheysen and Fenoll, 2002). Thus, a promoter identified from among genes that are reproducibly expressed in feeding sites may be utilized. Examples of genes up-regulated in feeding sites (syncytia) formed by nematodes include Hs1pro-1 (Thurau et al. 2003), AtSUC2 normally expressed in companion cells (Juergensen et al. 2003), At17.1 expressed in vascular tissues and root tips (Mazarei et al. 2004), FGAM synthase (phosphoribosylformyl-glycinamidine synthase) (Vaghchhipawala et al. 2004), and ABI3 (De Meutter et al. 2005), among others. Syncytia formed in response to cyst nematodes have been described as symplastically isolated lacking plasmodesmata to surrounding tissues (Bockenhoff and Grundler 1994; Bockenhoff et al. 1996), however, it has been shown that macromolecules up to 30 kD can move from phloem companion cells into the syncytium (Hoth et al. 2005). Therefore, gene expression in the phloem may also be suited for delivery of effector molecules into feeding sites.

A nucleotide sequence provided by the present invention may comprise an inverted repeat separated by a "spacer sequence." The spacer sequence may be a region comprising any sequence of nucleotides that facilitates secondary structure formation between each repeat, where this is required. In one embodiment of the present invention, the spacer sequence is part of the sense or antisense coding sequence for mRNA. The spacer sequence may alternatively comprise any combination of nucleotides or homologues thereof that are capable of being linked covalently to a nucleic acid molecule. The spacer sequence may comprise, for example, a sequence of nucleotides of at least about 10-100 nucleotides in length, or alternatively at least about 100-200 nucleotides in length, at least 200-400 about nucleotides in length, or at least about 400-500 nucleotides in length.

The nucleic acid molecules or fragments of the nucleic acid molecules or other nucleic acid molecules in the sequence listing are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the complement of another nucleic acid molecule if they exhibit complete complementarity. Two molecules are said to be "minimally complementary" if they can hybridize to one another with sufficient stability to permit them to remain annealed to one another under at least conventional "low-stringency" conditions. Similarly, the molecules are said to be complementary if they can hybridize to one another with sufficient stability to permit them to remain annealed to one another under conventional "high-stringency" conditions. Conventional stringency conditions are described by Sambrook, et al. (1989), and by Haymes et al. (1985).

Departures from complete complementarity are therefore permissible, as long as such departures do not completely preclude the capacity of the molecules to form a double-stranded structure. Thus, in order for a nucleic acid molecule or a fragment of the nucleic acid molecule to serve as a primer or probe it needs only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology (1989). For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. A nucleic acid for use in the present invention may specifically hybridize to one or more of nucleic acid molecules from a nematode or complements thereof under such conditions. Preferably, a nucleic acid for use in the present invention will exhibit at least from about 80%, or at least from about 90%, or at least from about 95%, or at least from about 98% or even about 100% sequence identity with one or more nucleic acid molecules as set forth in SEQ ID NOs:301-1026, SEQ ID NOs:1269-1702, and SEQ ID NOs:1920-1929, in the sequence listing.

Nucleic acids of the present invention may also be synthesized, either completely or in part, especially where it is desirable to provide plant-preferred sequences, by methods known in the art. Thus, all or a portion of the nucleic acids of the present invention may be synthesized using codons preferred by a selected host. Species-preferred codons may be determined, for example, from the codons used most frequently in the proteins expressed in a particular host species. Other modifications of the nucleotide sequences may result in mutants having slightly altered activity.

dsRNA or siRNA nucleotide sequences comprise double strands of polymerized ribonucleotide and may include modifications to either the phosphate-sugar backbone or the nucleoside. Modifications in RNA structure may be tailored to allow specific genetic inhibition. In one embodiment, the dsRNA molecules may be modified through an enzymatic process so that siRNA molecules may be generated. The siRNA can efficiently mediate the down-regulation effect for some target genes in some pathogens. This enzymatic process may be accomplished by utilizing an RNAse III enzyme or a DICER enzyme, present in the cells of an insect, a vertebrate animal, a fungus or a plant in the eukaryotic RNAi pathway (Elbashir et al., 2001; Hamilton and Baulcombe, 1999). This process may also utilize a recombinant DICER or RNAse III introduced into the cells of a target insect through recombinant DNA techniques that are readily known to the skilled in the art. Both the DICER enzyme and RNAse III, being naturally occurring in a pathogen or being made through recombinant DNA techniques, cleave larger dsRNA strands into smaller oligonucleotides. The DICER enzymes specifically cut the dsRNA molecules into siRNA pieces each of which is about 19-25 nucleotides in length while the RNAse III enzymes normally cleave the dsRNA molecules into 12-15 base-pair siRNA. The siRNA molecules produced by the either of the enzymes have 2 to 3 nucleotide 3' overhangs, and 5' phosphate and 3' hydroxyl termini. The siRNA molecules generated by RNAse III enzyme are the same as those produced by Dicer enzymes in the eukaryotic RNAi pathway and are hence then targeted and degraded by an inherent cellular RNA-degrading mechanism after they are subsequently unwound, separated into single-stranded RNA and hybridize with the RNA sequences transcribed by the target gene. This process results in the effective degradation or removal of the RNA sequence encoded by the nucleotide sequence of the target gene in the pathogen. The outcome is the silencing of a particularly targeted nucleotide sequence within the pathogen. Detailed descriptions of enzymatic processes can be found in Hannon (2002).

A nucleotide sequence of the present invention can be recorded on computer readable media. As used herein, "computer readable media" refers to any tangible medium of expression that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; optical character recognition formatted computer files, and hybrids of these categories such as magnetic/optical storage media. A skilled artisan can readily appreciate that any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII text file, stored in a database application, such as DB2, Sybase, Oracle, or the like. The skilled artisan can readily adapt any number of data processor structuring formats (e.g. text file or database) in order to obtain computer readable medium having recorded thereon the nucleotide sequence information of the present invention.

Computer software is publicly available which allows a skilled artisan to access sequence information provided in a computer readable medium. Software that implements the BLAST (Altschul et al., 1990) and BLAZE (Brutlag, et al., 1993) search algorithms on a Sybase system can be used to identify open reading frames (ORFs) within sequences such as the Unigenes and EST's that are provided herein and that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As used herein, "a target structural motif," or "target motif," refers to any rationally selected sequence or combination of sequences in which the sequences or sequence(s) are chosen based on a three-dimensional configuration that is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

B. Recombinant Vectors and Host Cell Transformation

A recombinant DNA vector may, for example, be a linear or a closed circular plasmid. The vector system may be a single vector or plasmid or two or more vectors or plasmids that together contain the total DNA to be introduced into the genome of the bacterial host. In addition, a bacterial vector may be an expression vector. Nucleic acid molecules as set forth in SEQ ID NOs:301-1026 SEQ ID NOs:1269-1702, and SEQ ID NOs:1920-1929, or fragments thereof, can, for example, be suitably inserted into a vector under the control of a suitable promoter that functions in one or more microbial hosts to drive expression of a linked coding sequence or other DNA sequence. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more selectable marker genes, and an inducible promoter allowing the expression of exogenous DNA.

Expression and cloning vectors generally contain a selection gene, also referred to as a selectable marker. This gene encodes a protein necessary for the survival or growth of transformed host cells grown in a selective culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. Those cells that are successfully transformed with a heterologous protein or fragment thereof produce a protein conferring drug resistance and thus survive the selection regimen.

An expression vector for producing a mRNA can also contain an inducible promoter that is recognized by a host bacterial organism and is operably linked to the nucleic acid. Inducible promoters suitable for use with bacterial hosts include β-lactamase promoter, *E. coli*λ phage PL and PR promoters, and *E. coli* galactose promoter, arabinose promoter, alkaline phosphatase promoter, tryptophan (trp) promoter, and the lactose operon promoter and variations thereof and hybrid promoters such as the tac promoter. However, other known bacterial inducible promoters are suitable.

The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream (5' noncoding sequences), within, or downstream (3' non-translated sequences) of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, and polyadenylation recognition sequences and the like.

Construction of suitable vectors containing one or more of the above-listed components employs standard recombinant DNA techniques. Isolated plasmids or DNA fragments are cleaved, tailored, and re-ligated in the form desired to generate the plasmids required. Examples of available bacterial expression vectors include, but are not limited to, the multifunctional *E. coli* cloning and expression vectors such as Bluescript™ (Stratagene, La Jolla, Calif.), in which, for example, a nucleic acid, or fragment thereof, shown in FIG. 3 may be ligated into the vector in frame with sequences for the amino-terminal Met and the subsequent 7 residues of β-galactosidase so that a hybrid protein is produced; pIN vectors (Van Heeke and Schuster, 1989); and the like.

The present invention also contemplates transformation of a nucleotide sequence of the present invention into a plant to achieve nematode-inhibitory levels of expression of one or more dsRNA molecules. A transformation vector can be readily prepared using methods available in the art. The transformation vector comprises one or more nucleotide sequences that is/are capable of being transcribed to an RNA molecule and that is/are substantially homologous and/or complementary to one or more nucleotide sequences encoded by the genome of the target nematode, such that upon uptake of the RNA transcribed from the one or more nucleotide sequences by the target plant-parasitic nematode, there is down-regulation of expression of at least one of the respective nucleotide sequences of the genome of the nematode.

The transformation vector may be termed a dsDNA construct and may also be defined as a recombinant molecule, a disease control agent, a genetic molecule or a chimeric genetic construct. A chimeric genetic construct of the present invention may comprise, for example, nucleotide sequences encoding one or more antisense transcripts, one or more sense transcripts, one or more of each of the aforementioned, wherein all or part of a transcript there from is homologous to all or part of an RNA molecule comprising an RNA sequence encoded by a nucleotide sequence within the genome of a pathogen.

In one embodiment a plant transformation vector comprises an isolated and purified DNA molecule comprising a heterologous promoter operatively linked to one or more nucleotide sequences of the present invention. The nucleotide sequence is selected from the group consisting of SEQ ID NOs:301-1026, SEQ ID NOs:1269-1702, and SEQ ID NOs:1920-1929, as set forth in the sequence listing. The nucleotide sequence includes a segment coding all or part of an RNA present within a targeted nematode RNA transcript and may comprise inverted repeats of all or a part of a targeted nematode RNA. The DNA molecule comprising the expression vector may also contain a functional intron sequence positioned either upstream of the coding sequence or even within the coding sequence, and may also contain a five prime (5') untranslated leader sequence (i.e., a UTR or 5'-UTR) positioned between the promoter and the point of translation initiation.

A plant transformation vector may contain sequences from more than one gene, thus allowing production of more than one dsRNA for inhibiting expression of two or more genes in cells of a target nematode. One skilled in the art will readily appreciate that segments of DNA whose sequence corresponds to that present in different genes can be combined into a single composite DNA segment for expression in a transgenic plant. Alternatively, a plasmid of the present invention already containing at least one DNA segment can be modified by the sequential insertion of additional DNA segments between the enhancer and promoter and terminator sequences. In the disease control agent of the present invention designed for the inhibition of multiple genes, the genes to be inhibited can be obtained from the same plant-parasitic nematode species in order to enhance the effectiveness of the control agent. In certain embodiments, the genes can be derived from different plant-parasitic nematodes in order to broaden the range of nematodes against which the agent(s) is/are effective. When multiple genes are targeted for suppression or a combination of expression and suppression, a polycistronic DNA element can be fabricated as illustrated and disclosed in US Publication No. US 2004-0029283.

Promoters that function in different plant species are also well known in the art. Promoters useful for expression of polypeptides in plants include those that are inducible, viral, synthetic, or constitutive as described in Odell et al. (1985), and/or promoters that are temporally regulated, spatially regulated, and spatio-temporally regulated. Preferred promoters include the enhanced CaMV35S promoters, and the FMV35S promoter. A fragment of the CaMV35S promoter exhibiting root-specificity may also be preferred. For the purpose of the present invention, it may be preferable to achieve the highest levels of expression of these genes within the root tissues of plants. A number of root-specific promoters have been identified and are known in the art (e.g. U.S. Pat. Nos. 5,110,732; 5,837,848; 5,459,252; Hirel et al. 1992).

A recombinant DNA vector or construct of the present invention may comprise a selectable marker that confers a selectable phenotype on plant cells. Selectable markers may also be used to select for plants or plant cells that contain the exogenous nucleic acids encoding polypeptides or proteins of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene which codes for kanamycin resistance and can be selected for using kanamycin, G418, etc., a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, and tetracycline, and the like. Examples of such selectable markers are illustrated in U.S. Pat. Nos. 5,550,318; 5,633,435; 5,780,708 and 6,118,047.

A recombinant vector or construct of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al., 1987); an R-locus gene, which encodes a product that regulates the production of anthocyanin pigments (red color) in plant tissues (Dellaporta et al., 1988); a β-lactamase gene (Sutcliffe et al., 1978), a gene which encodes an enzyme for which various chromogenic substrates are known (e.g., PADAC, a chromogenic cephalosporin); a luciferase gene (Ow et al., 1986) a xylE gene (Zukowski et al., 1983) which encodes a catechol dioxygenase that can convert chromogenic catechols; an α-amylase gene (Ikatu et al., 1990); a tyrosinase gene (Katz et al., 1983) which encodes an enzyme capable of oxidizing tyrosine to DOPA and dopaquinone which in turn condenses to melanin; an α-galactosidase, which catalyzes a chromogenic α-galactose substrate.

Preferred plant transformation vectors include those derived from a Ti plasmid of *Agrobacterium tumefaciens* (e.g. U.S. Pat. Nos. 4,536,475, 4,693,977, 4,886,937, 5,501, 967 and EP 0 122 791). *Agrobacterium rhizogenes* plasmids (or "Ri") are also useful and known in the art. Other preferred plant transformation vectors include those disclosed, e.g., by Herrera-Estrella (1983); Bevan (1983), Klee (1985) and EP 0 120 516.

In general it may be preferred to introduce a functional recombinant DNA at a non-specific location in a plant genome. In special cases it may be useful to insert a recombinant DNA construct by site-specific integration. Several site-specific recombination systems exist which are known to function implants include cre-lox as disclosed in U.S. Pat. No. 4,959,317 and FLP-FRT as disclosed in U.S. Pat. No. 5,527,695.

Suitable methods for transformation of host cells for use with the current invention are believed to include virtually any method by which DNA can be introduced into a cell (see, for example, Miki et al., 1993), such as by transformation of protoplasts (U.S. Pat. No. 5,508,184; Omirulleh et al., 1993), by desiccation/inhibition-mediated DNA uptake (Potrykus et al., 1985), by electroporation (U.S. Pat. No. 5,384,253), by agitation with silicon carbide fibers (Kaeppler et al., 1990; U.S. Pat. No. 5,302,523; and U.S. Pat. No. 5,464,765), by *Agrobacterium*-mediated transformation (U.S. Pat. Nos. 5,563,055; 5,591,616; 5,693,512; 5,824,877; 5,981,840; 6,384,301) and by acceleration of DNA coated particles (U.S. Pat. Nos. 5,015,580; 5,550,318; 5,538,880; 6,160,208; 6,399,861; 6,403,865; Padgette et al. 1995), etc. Through the application of techniques such as these, the cells of virtually any species may be stably transformed. In the case of multicellular species, the transgenic cells may be regenerated into transgenic organisms.

The most widely utilized method for introducing an expression vector into plants is based on the natural transformation system of *Agrobacterium* (for example, Horsch et al., 1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. Descriptions of *Agrobacterium* vector systems and methods for *Agrobacterium*-mediated gene transfer are provided by numerous references, including Gruber et al. 1993; Miki et al., 1993, Moloney et al., 1989, and U.S. Pat. Nos. 4,940,838 and 5,464,763. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector (Broothaerts et al. 2005).

Methods for the creation of transgenic plants and expression of heterologous nucleic acids in plants in particular are known and may be used with the nucleic acids provided herein to prepare transgenic plants that exhibit reduced susceptibility to feeding by a target nematode. Plant transformation vectors can be prepared, for example, by inserting the dsRNA producing nucleic acids disclosed herein into plant transformation vectors and introducing these into plants. One known vector system has been derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences. The T-region may also contain a selectable marker for efficient recovery of transgenic plants and cells, and a multiple cloning site for inserting sequences for transfer such as a dsRNA encoding nucleic acid.

A transgenic plant formed using *Agrobacterium* transformation methods typically contains a single simple recombinant DNA sequence inserted into one chromosome and is referred to as a transgenic event. Such transgenic plants can be referred to as being heterozygous for the inserted exogenous sequence. A transgenic plant homozygous with respect to a transgene can be obtained by sexually mating (selfing) an independent segregant transgenic plant that contains a single exogenous gene sequence to itself, for example an F0 plant, to produce F1 seed. One fourth of the F1 seed produced will be homozygous with respect to the transgene. Germinating F1 seed results in plants that can be tested for heterozygosity, typically using a SNP assay or a thermal amplification assay that allows for the distinction between heterozygotes and homozygotes (i.e., a zygosity assay). Crossing a heterozygous plant with itself or another heterozygous plant results in only heterozygous progeny.

C. Nucleic Acid Expression and Target Gene Suppression

The present invention provides, as an example, a transformed host plant of a pathogenic target organism, transformed plant cells and transformed plants and their progeny. The transformed plant cells and transformed plants may be engineered to express one or more of the dsRNA or siRNA sequences, under the control of a heterologous promoter, described herein to provide a pathogen-protective effect. These sequences may be used for gene suppression in a pathogen, thereby reducing the level or incidence of disease caused by the pathogen on a protected transformed host organism. As used herein the words "gene suppression" are intended to refer to any of the well-known methods for reducing the levels of protein produced as a result of gene transcription to mRNA and subsequent translation of the mRNA.

Gene suppression is also intended to mean the reduction of protein expression from a gene or a coding sequence including posttranscriptional gene suppression and transcriptional suppression. Posttranscriptional gene suppression is mediated by the homology between all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi).

Transcriptional suppression is mediated by the presence in the cell of a dsRNA gene suppression agent exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in a plant-parasitic nematode that may ingest or contact plant material containing gene suppression agents, specifically designed to inhibit or suppress the expression of one or more homologous or complementary sequences in the cells of the nematode. Post-transcriptional gene suppression by anti-sense or sense oriented RNA to regulate gene expression in plant cells is disclosed in U.S. Pat. Nos. 5,107,065, 5,759,829, 5,283,184, and 5,231,020. The use of dsRNA to suppress genes in plants is disclosed in WO 99/53050, WO 99/49029, U.S. Publication No. 2003/0175965, and 2003/0061626, U.S. patent application Ser. No. 10/465,800, and U.S. Pat. Nos. 6,506,559, and 6,326,193.

A beneficial method of post transcriptional gene suppression versus a plant-parasitic nematode employs both sense-oriented and anti-sense-oriented, transcribed RNA which is stabilized, e.g., as a hairpin and stem and loop structure. A preferred DNA construct for effecting post transcriptional gene suppression is one in which a first segment encodes an RNA exhibiting an anti-sense orientation exhibiting substantial identity to a segment of a gene targeted for suppression, which is linked to a second segment encoding an RNA exhibiting substantial complementarity to the first segment. Such a construct forms a stem and loop structure by hybridization of the first segment with the second segment and a loop structure from the nucleotide sequences linking the two segments (see WO94/01550, WO98/05770, US 2002/0048814, and US 2003/0018993). Co-expression with an additional target gene segment may also be employed, as noted above (e.g. WO05/019408).

According to one embodiment of the present invention, there is provided a nucleotide sequence, for which in vitro expression results in transcription of a stabilized RNA sequence that is substantially homologous to an RNA molecule of a targeted gene in a plant-parasitic nematode that comprises an RNA sequence encoded by a nucleotide sequence within the genome of the nematode. Thus, after the plant-parasitic nematode ingests the stabilized RNA sequence, a down-regulation of the nucleotide sequence corresponding to the target gene in the cells of a target nematode is effected.

In certain embodiments of the invention, expression of a fragment of at least 21 contiguous nucleotides of a nucleic acid sequence of any of SEQ ID NOs:301-1026, SEQ ID NOs:1269-1702, and SEQ ID NOs:1920-1929 may be utilized, including expression of a fragment of up to 21, 36, 60, 100, 550, or 1000 contiguous nucleotides, or sequences displaying 90-100% identity with such sequences, or their complements. In specific embodiments, a nucleotide provided by the invention may comprise a sequence selected from the group described in Table 4, including a location on such sequence spanning nucleotides as described in Table 4. In yet other embodiments, a nucleotide provided by the invention may be described as comprising one or more of nucleotides 1-21, 22-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, 2001-2050, 2051-2100, 23-75, 76-125, 126-175, 176-225, 226-275, 276-325, 326-375, 376-425, 426-475, 476-525, 526-575, 576-625, 626-675, 676-725, 726-775, 776-825, 826-875, 876-925, 926-975, 976-1025, 1026-1075, 1076-1125, 1126-1175, 1176-1225, 1226-1275, 1276-1325, 1326-1375, 1376-1425, 1426-1475, 1476-1525, 1526-1575, 1576-1625, 1626-1675, 1676-1725, 1726-1775, 1776-1825, 1826-1875, 1876-1925, 1926-1975, 1976-2025, 2026-2075, 2076-2125, 1-550, 200-750, 300-850, 400-950, 500-1050, 600-1150, 700-1250, 800-1350, 900-1450, 1000-1550, 1100-1650, 1200-1750, 1300-1850, 1400-1950, 1500-2050, up to the full length of the sequence, of one or more of SEQ ID NOs:301-1026, SEQ ID NOs:1269-1702, and SEQ ID NOs:1920-1929. However, in certain embodiments, the invention does not comprise SEQ ID NOs:525, 569, 797, 1293 or 1516, or fragments thereof. Methods for selecting specific sub-sequences as targets for siRNA-mediated gene suppression are known in the art (e.g. Reynolds et al. 2004).

Inhibition of a target gene using the stabilized dsRNA technology of the present invention is sequence-specific in that nucleotide sequences corresponding to the duplex region of the RNA are targeted for genetic inhibition. RNA containing a nucleotide sequences identical to a portion of the target gene is preferred for inhibition. RNA sequences with insertions, deletions, and single point mutations relative to the target sequence have also been found to be effective for inhibition. In performance of the present invention, it is preferred that the inhibitory dsRNA and the portion of the target gene share at least from about 80% sequence identity, or from about 90% sequence identity, or from about 95% sequence identity, or from about 99% sequence identity, or even about 100% sequence identity. Alternatively, the duplex region of the RNA may be defined functionally as a nucleotide sequence that is capable of hybridizing with a portion of the target gene transcript. A less than full length sequence exhibiting a greater homology compensates for a longer less homologous sequence. The length of the identical nucleotide sequences may be at least about 25, 50, 100, 200, 300, 400, 500 or at least about 1000 bases. Normally, a sequence of greater than 20-100 nucleotides should be used, though a sequence of greater than about 200-300 nucleotides would be preferred, and a sequence of greater than about 500-1000 nucleotides would be especially preferred depending on the size of the target gene. The invention has the advantage of being able to tolerate sequence variations that might be expected due to genetic mutation, strain polymorphism, or evolutionary divergence. The introduced nucleic acid molecule may not need to be absolute homology, may not need to be full length, relative to either the primary transcription product or fully processed mRNA of the target gene. Therefore, those skilled in the art need to realize that, as disclosed herein, 100% sequence identity between the RNA and the target gene is not required to practice the present invention.

Inhibition of target gene expression may be quantified by measuring either the endogenous target RNA or the protein produced by translation of the target RNA and the consequences of inhibition can be confirmed by examination of the outward properties of the cell or organism. Techniques for quantifying RNA and proteins are well known to one of ordinary skill in the art.

In certain embodiments gene expression is inhibited by at least 10%, preferably by at least 33%, more preferably by at least 50%, and yet more preferably by at least 80%. In particularly preferred embodiments of the invention gene expression is inhibited by at least 80%, more preferably by at least 90%, more preferably by at least 95%, or by at least 99% within cells in the pathogen so a significant inhibition takes place. Significant inhibition is intended to refer to sufficient inhibition that results in a detectable phenotype (e.g., cessation of growth, feeding, development, mortality, etc.) or a detectable decrease in RNA and/or protein corresponding to the target gene being inhibited. Although in certain embodiments of the invention inhibition occurs in substantially all cells of the plant-parasitic nematode, in other preferred embodiments inhibition occurs in only a subset of cells expressing the gene.

dsRNA molecules may be synthesized either in vivo or in vitro. The dsRNA may be formed by a single self-complementary RNA strand or from two complementary RNA strands. Endogenous RNA polymerase of the cell may mediate transcription in vivo, or cloned RNA polymerase can be used for transcription in vivo or in vitro Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus.

A RNA, dsRNA, siRNA, or miRNA of the present invention may be produced chemically or enzymatically by one skilled in the art through manual or automated reactions or in vivo in another organism. RNA may also be produced by partial or total organic synthesis; any modified ribonucleotide can be introduced by in vitro enzymatic or organic synthesis. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593,874, 5,698,425, 5,712,135, 5,789,214, and 5,804,693). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

For transcription from a transgene in vivo or an expression construct, a regulatory region (e.g., promoter, enhancer, silencer, and polyadenylation) may be used to transcribe the RNA strand (or strands). Therefore, in one embodiment, the nucleotide sequences for use in producing RNA molecules may be operably linked to one or more promoter sequences functional in a microorganism, a fungus or a plant host cell. Ideally, the nucleotide sequences are placed under the control of an endogenous promoter, normally resident in the host genome. The nucleotide sequence of the present invention, under the control of an operably linked promoter sequence, may further be flanked by additional sequences that advantageously affect its transcription and/or the stability of a resulting transcript. Such sequences are generally located upstream of the operably linked promoter and/or downstream of the 3' end of the expression construct and may occur both upstream of the promoter and downstream of the 3' end of the expression construct, although such an upstream sequence only is also contemplated.

As used herein, the term "disease control agent", or "gene suppression agent" refers to a particular RNA molecule consisting of a first RNA segment and a second RNA segment linked by a third RNA segment. The first and the second RNA segments lie within the length of the RNA molecule and are substantially inverted repeats of each other and are linked together by the third RNA segment. The complementarity between the first and the second RNA segments results in the ability of the two segments to hybridize in vivo and in vitro to form a double stranded molecule, i.e., a stem, linked together at one end of each of the first and second segments by the third segment which forms a loop, so that the entire structure forms into a stem and loop structure, or even more tightly hybridizing structures may form into a stem-loop knotted structure. The first and the second segments correspond invariably and not respectively to a sense and an antisense sequence with respect to the target RNA transcribed from the target gene in the target pathogen that is suppressed by the ingestion of the dsRNA molecule. The control agent can also be a substantially purified (or isolated) nucleic acid molecule and more specifically nucleic acid molecules or nucleic acid fragment molecules thereof from a genomic DNA (gDNA) or cDNA library. Alternatively, the fragments may comprise smaller oligonucleotides having from about 15 to about 250 nucleotide residues, and more preferably, about 15 to about 30 nucleotide residues.

As used herein, the term "genome" as it applies to cells of a plant-parasitic nematode or a host encompasses not only chromosomal DNA found within the nucleus, but organelle DNA found within subcellular components of the cell. The DNA's of the present invention introduced into plant cells can therefore be either chromosomally integrated or organelle-localized. The term "genome" as it applies to bacteria encompasses both the chromosome and plasmids within a bacterial host cell. The DNA's of the present invention introduced into bacterial host cells can therefore be either chromosomally integrated or plasmid-localized.

As used herein, the term "plant-parasitic nematode" refers to those nematodes that may infect, colonize, parasitize, or cause disease on host plant material transformed to express or coated with a double stranded gene suppression agent. As used herein, a "nematode resistance" trait is a characteristic of a transgenic plant, transgenic animal, or other transgenic host that causes the host to be resistant to attack from a nematode that typically is capable of inflicting damage or loss to the host. Such resistance can arise from a natural mutation or more typically from incorporation of recombinant DNA that confers plant-parasitic nematode resistance. To impart nematode resistance to a transgenic plant a recombinant DNA can, for example, be transcribed into a RNA molecule that forms a dsRNA molecule within the tissues or fluids of the recombinant plant. The dsRNA molecule is comprised in part of a segment of RNA that is identical to a corresponding RNA segment encoded from a DNA sequence within a plant-parasitic nematode that prefers to cause disease on the host plant. Expression of the gene within the target plant-parasitic nematode is suppressed by the dsRNA, and the suppression of expression of the gene in the target plant-parasitic nematode results in the plant being resistant to the nematode. Fire et al. (U.S. Pat. No. 6,506,599) generically describes inhibition of pest infestation, providing specifics only about several nucleotide sequences that were effective for inhibition of gene function in the nematode species Caenorhabditis elegans. Similarly, US 2003/0061626 describes the use of dsRNA for inhibiting gene function in a variety of nematode pests. US 2003/0150017 describes using dsDNA sequences to transform host cells to express corresponding dsRNA sequences that are substantially identical to target sequences in specific pests, and particularly describe constructing recombinant plants expressing such dsRNA sequences for ingestion by various plant-parasitic nematode, facilitating down-regulation of a gene in the genome of the target organism and improving the resistance of the plant to the plant-parasitic nematode.

The modulatory effect of dsRNA is applicable to a variety of genes expressed in the plant-parasitic nematode including, for example, endogenous genes responsible for cellular metabolism or cellular transformation, including house keeping genes, transcription factors, molting-related genes, and other genes which encode polypeptides involved in cellular metabolism or normal growth and development.

As used herein, the phrase "inhibition of gene expression" or "inhibiting expression of a target gene in the cell of a plant-parasitic nematode" refers to the absence (or observable decrease) in the level of protein and/or mRNA product from the target gene. Specificity refers to the ability to inhibit the target gene without manifest effects on other genes of the cell and without any effects on any gene within the cell that is producing the dsRNA molecule. The inhibition of gene expression of the target gene in the plant-parasitic nematode may result in novel phenotypic traits in the nematode.

The present invention provides in part a delivery system for the delivery of the nematode control agents by ingestion of host cells or the contents of the cells. In accordance with another embodiment, the present invention involves generating a transgenic plant cell or a plant that contains a recombinant DNA construct transcribing the stabilized dsRNA molecules of the present invention. As used herein, "taking up" refers to the process of an agent coming in contact with cells of a target organism, such as a nematode. This may occur, for instance, by nematode feeding, by soaking, or by injection. As used herein, the phrase "generating a transgenic plant cell or a plant" refers to the methods of employing the recombinant DNA technologies readily available in the art (e.g., by Sambrook, et al., 1989) to construct a plant transformation vector transcribing the stabilized dsRNA molecules of the present invention, to transform the plant cell or the plant and to generate the transgenic plant cell or the transgenic plant that contain the transcribed, stabilized dsRNA molecules.

It is envisioned that the compositions of the present invention can be incorporated within the seeds of a plant species either as a product of expression from a recombinant gene incorporated into a genome of the plant cells, or incorporated into a coating or seed treatment that is applied to the seed before planting. The plant cell containing a recombinant gene is considered herein to be a transgenic event.

The present invention provides in part a delivery system for the delivery of disease control agents to plant-parasitic nematodes. The stabilized dsRNA or siRNA molecules of the present invention may be directly introduced into the cells of a plant-parasitic nematode. Methods for introduction may include direct mixing of RNA with host tissue for the plant-parasitic nematode, as well as engineered approaches in which a species that is a host is engineered to express the dsRNA or siRNA. In one embodiment, the RNA may be sprayed onto a plant surface. In still another embodiment, the dsRNA or siRNA may be expressed by microorganisms and the microorganisms may be applied onto a plant surface or introduced into a root, stem by a physical means such as an injection. In still another embodiment, a plant may be genetically engineered to express the dsRNA or siRNA in an amount sufficient to kill the plant-parasitic nematodes known to infest the plant.

It is also anticipated that dsRNAs produced by chemical or enzymatic synthesis may be formulated in a manner consistent with common agricultural practices and used as spray-on products for controlling plant disease. The formulations may include the appropriate stickers and wetters required for efficient foliar coverage as well as UV protectants to protect dsRNAs from UV damage. Such additives are commonly used in the bioinsecticide industry and are well known to those skilled in the art. Such applications could be combined with other spray-on insecticide applications, biologically based or not, to enhance plant protection from plant-parasitic nematodes The present invention also relates to recombinant DNA constructs for expression in a microorganism. Exogenous nucleic acids from which an RNA of interest is transcribed can be introduced into a microbial host cell, such as a bacterial cell or a fungal cell, using methods known in the art.

The nucleotide sequences of the present invention may be introduced into a wide variety of prokaryotic and eukaryotic microorganism hosts to produce the stabilized dsRNA or siRNA molecules. The term "microorganism" includes prokaryotic and eukaryotic species such as bacteria and fungi, as well as nematodes. Fungi include yeasts and filamentous fungi, among others. Illustrative prokaryotes, both Gram-negative and Gram-positive, include Enterobacteriaceae, such as *Escherichia*, *Erwinia*, and *Serratia*; Bacillaceae; Rhizobiaceae, such as *Rhizobium*; Spirillaceae, such as photobacterium, *Zymomonas*; Lactobacillaceae; Pseudomonadaceae, such as *Pseudomonas* and *Acetobacter*; Azotobacteraceae, Actinomycetales, and Nitrobacteraceae. Among eukaryotes are fungi, such as Phycomycetes and Ascomycetes, including *Saccharomyces* and *Schizosaccharomyces*; and Basidiomycetes, such as *Rhodotorula*, *Aureobasidium*, and the like.

D. Transgenic Plants

The present invention provides seeds and plants having one or more transgenic event. Combinations of events are referred to as "stacked" transgenic events. These stacked transgenic events can be events that are directed at the same target organism, or they can be directed at different target pathogens or pests. In one embodiment, a seed having the ability to express a nucleic acid provided herein also has the ability to express at least one other agent, including, but not limited to, an RNA molecule the sequence of which is derived from the sequence of an RNA expressed in a target pathogen such as a nematode and that forms a double stranded RNA structure upon expressing in the seed or cells of a plant grown from the seed, wherein the ingestion of one or more cells of the plant by the target results in the suppression of expression of the RNA in the cells of the target.

In certain embodiments, a seed having the ability to express a dsRNA the sequence of which is derived from a target plant-parasitic nematode also has a transgenic event that provides herbicide tolerance. One beneficial example of a herbicide tolerance gene provides resistance to glyphosate, N-(phosphonomethyl) glycine, including the isopropylamine salt form of such herbicide.

Benefits provided by the present invention may include, but are not limited to: the ease of introducing dsRNA into the plant-parasitic nematode cells, the low concentration of dsRNA which can be used, the stability of dsRNA, and the effectiveness of the inhibition. The ability to use a low concentration of a stabilized dsRNA avoids several disadvantages of anti-sense interference. The present invention is not limited to in vitro use or to specific sequence compositions, to a particular set of target genes, a particular portion of the target gene's nucleotide sequence, or a particular transgene or to a particular delivery method, as opposed to the some of the available techniques known in the art, such as antisense and co-suppression. Furthermore, genetic manipulation becomes possible in organisms that are not classical genetic models.

In order to achieve inhibition of a target gene selectively within a plant-parasitic nematode species that it is desired to control, the target gene should preferably exhibit a low degree of sequence identity with corresponding genes in a plant or a vertebrate animal. Preferably the degree of the sequence identity is less than approximately 80%. More preferably the degree of the sequence identity is less than approximately 70%. Most preferably the degree of the sequence identity is less than approximately 60%.

In addition to direct transformation of a plant with a recombinant DNA construct, transgenic plants can be prepared by crossing a first plant having a recombinant DNA construct with a second plant lacking the construct. For example, recombinant DNA for gene suppression can be introduced into first plant line that is amenable to transformation to produce a transgenic plant that can be crossed with a second plant line to introgress the recombinant DNA for gene suppression into the second plant line.

The present invention can be, in practice, combined with other disease control traits in a plant to achieve desired traits for enhanced control of plant disease. Combining disease control traits that employ distinct modes-of-action can provide protected transgenic plants with superior durability over plants harboring a single control trait because of the reduced probability that resistance will develop in the field.

The invention also relates to commodity products containing one or more of the sequences of the present invention, and produced from a recombinant plant or seed containing one or more of the nucleotide sequences of the present invention are specifically contemplated as embodiments of the present invention. A commodity product containing one or more of the sequences of the present invention is intended to include, but not be limited to, meals, oils, crushed or whole grains or seeds of a plant, or any food product comprising any meal, oil, or crushed or whole grain of a recombinant plant or seed containing one or more of the sequences of the present invention. The detection of one or more of the sequences of the present invention in one or more commodity or commodity products contemplated herein is defacto evidence that the commodity or commodity product is composed of a transgenic plant designed to express one or more of the nucleotides sequences of the present invention for the purpose of controlling plant disease using dsRNA mediated gene suppression methods.

E. Obtaining Nucleic Acids

The present invention provides methods for obtaining a nucleic acid comprising a nucleotide sequence for producing a dsRNA or siRNA. In one embodiment, such a method comprises: (a) analyzing one or more target gene(s) for their expression, function, and phenotype upon dsRNA-mediated gene suppression in a nematode; (b) probing a cDNA or gDNA library with a hybridization probe comprising all or a portion of a nucleotide sequence or a homolog thereof from a targeted nematode that displays an altered, e.g. reduced, nematode growth or development phenotype in a dsRNA-mediated suppression analysis; (c) identifying a DNA clone that hybridizes with the hybridization probe; (d) isolating the DNA clone identified in step (b); and (e) sequencing the cDNA or gDNA fragment that comprises the clone isolated in step (d) wherein the sequenced nucleic acid molecule transcribes all or a substantial portion of the RNA nucleotide acid sequence or a homolog thereof.

In another embodiment, a method of the present invention for obtaining a nucleic acid fragment comprising a nucleotide sequence for producing a substantial portion of a dsRNA or siRNA comprises: (a) synthesizing first and a second oligonucleotide primers corresponding to a portion of one of the nucleotide sequences from a targeted pathogen; and (b) amplifying a cDNA or gDNA insert present in a cloning vector using the first and second oligonucleotide primers of step (a) wherein the amplified nucleic acid molecule transcribes a substantial portion of the a substantial portion of a dsRNA or siRNA of the present invention.

In practicing the present invention, a target gene may be derived from *H. glycines* or another nematode. It is contemplated that several criteria may be employed in the selection of preferred target genes. The *H. glycines* gene may be one which has a *C. elegans* ortholog with a likelihood for a strong phenotype upon RNAi knockdown of expression, including a P0 phenotype. Such targets are often those with protein products involved in core cellular processes such as DNA replication, cell cycle, transcription, RNA processing, translation, protein trafficking, secretion, protein modification, protein stability and degradation, energy production, intermediary metabolism, cell structure, signal transduction, channels and transporters, and endocytosis. In certain embodiments it is advantageous to select a gene for which a small drop in expression level results in deleterious effects for the pathogen.

As used herein, the term "derived from" refers to a specified nucleotide sequence that may be obtained from a particular specified source or species, albeit not necessarily directly from that specified source or species.

In one embodiment, a gene is selected that is essentially involved in the growth and development, of a plant-parasitic nematode. Other target genes for use in the present invention may include, for example, those that play important roles in nematode viability, growth, development, infectivity, and establishment of feeding sites. These target genes may be one of the house keeping genes, transcription factors and the like. Additionally, the nucleotide sequences for use in the present invention may also be derived from homologs, including orthologs, of plant, viral, bacterial or insect genes whose functions have been established from literature and the nucleotide sequences of which share substantial similarity with the target genes in the genome of a target nematode. According to one aspect of the present invention for nematode control, the target sequences may essentially be derived from the targeted plant-parasitic nematode. Some of the exemplary target sequences cloned from a nematode that encode proteins or fragments thereof which are homologues of known proteins may be found in the Sequence Listing, for instance SEQ ID NOs:301-1026, SEQ ID NOs:1269-1702, and SEQ ID NOs:1920-1929.

For the purpose of the present invention, the dsRNA or siRNA molecules may be obtained by polymerase chain (PCR™) amplification of a target gene sequences derived from a gDNA or cDNA library or portions thereof. The DNA library may be prepared using methods known to the ordinary skilled in the art and DNA/RNA may be extracted. Genomic DNA or cDNA libraries generated from a target organism may be used for PCR™ amplification for production of the dsRNA or siRNA.

The target genes may be then be PCR™ amplified and sequenced using the methods readily available in the art. One skilled in the art may be able to modify the PCR™ conditions to ensure optimal PCR™ product formation. The confirmed PCR™ product may be used as a template for in vitro transcription to generate sense and antisense RNA with the included minimal promoters. In one embodiment, the present invention comprises isolated and purified nucleotide sequences that may be used as plant-parasitic nematode control agents. The isolated and purified nucleotide sequences may comprise those as set forth in the sequence listing.

As used herein, the phrase "coding sequence", "structural nucleotide sequence" or "structural nucleic acid molecule" refers to a nucleotide sequence that is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA, cDNA, EST and recombinant nucleotide sequences.

The term "recombinant DNA" or "recombinant nucleotide sequence" refers to DNA that contains a genetically engineered modification through manipulation via mutagenesis, restriction enzymes, and the like.

For many of the plant-parasitic nematodes that are potential targets for control by the present invention, there may be limited information regarding the sequences of most genes or the phenotype resulting from mutation of particular genes. Therefore, it is contemplated that selection of appropriate genes for use in the present invention may be accomplished through use of information available from study of the corresponding genes in a model organism such in *C. elegans*, in which the genes have been characterized, according to the analysis described in Examples 1-8. In some cases it will be possible to obtain the sequence of a corresponding gene from a target nematode by searching databases such as GenBank using either the name of the gene or the sequence from, for example, a nematode from which the gene has been cloned. Once the sequence is obtained, PCR™ may be used to amplify an appropriately selected segment of the gene in the target nematode for use in the present invention. PCR™ primers may be designed based on the sequence as found in another organism from which the gene has been cloned. The primers are designed to amplify a DNA segment of sufficient length for use in the present invention. DNA (either genomic DNA or cDNA) is prepared from the target plant-parasitic nematode, and the PCR™ primers are used to amplify the DNA segment. Amplification conditions are selected so that amplification will occur even if the primers do not exactly match the target sequence. Alternately, the gene (or a portion thereof) may be cloned from a gDNA or cDNA library prepared from a plant-parasitic nematode species, using the known gene as a probe. Techniques for performing PCR™ and cloning from libraries are known. Further details of the process by which DNA segments from target plant-parasitic nematodes species may be isolated based on the sequence of genes previously cloned from other species are provided in the Examples. One of ordinary skill in the art will recognize that a variety of techniques may be used to isolate gene segments from plant-parasitic nematodes that correspond to genes previously isolated from other species.

EXAMPLES

The inventors herein have identified a means for controlling plant-parasitic nematodes by providing double stranded ribonucleic acid molecules to plant-parasitic nematodes, and a means to select sequences that encode these double stranded ribonucleic acid molecules. Double stranded ribonucleic acid molecules that function upon ingestion to inhibit a biological function in a nematode may result, for example, in one or more of the following attributes: reduction in growth of a nematode, inhibition of development of a nematode, or reduction of viability. Any one or any combination of these attributes can result in an effective inhibition of plant infection or colonization, and in the case of a plant pathogenic nematode, inhibition of plant disease, and/or reduction in severity of disease symptoms.

Example 1

Criteria for Target Gene Selection

To rank genes by likely essentiality of function in the nematode lifecycle, information from *C. elegans* RNA interference (RNAi) experiments available at wormbase.org was combined with additional experimental information. Using the >40,000 phenotype data points in wormbase, all ~20,000 *C. elegans* genes were ranked for their potency of phenotype, level of confidence in phenotype, and likelihood of effects at multiple stages in the lifecycle. 715 *C. elegans* genes with BLAST amino acid homology to *H. glycines* of at least e-10 (see orthology determination below) had scores in this phenotype scoring system of 44 or better, where 1 is best. Below, phenotype statistics are provided for just the targets eventually making the top 300 list (using all criteria). As the phenotype ranking is dependent upon currently available information, it is not meant to be all inclusive capturing every gene that could be a good target, but rather to provide a list of high quality targets likely to be successful in *H. glycines* RNAi based on information in hand.

The following analysis of phenotypes evident following RNAi treatment was performed prior to the recent publication of Sonnichsen et al. *C. elegans* genome RNAi survey (Sonnichsen et al., 2005). This group tested 19,075 genes by injection of dsRNA into the gonads of *C. elegans* wild type strain N2 hermaphrodites and looked for effects on that animal and its progeny. They found effects for just 1,668 genes (8.7%). Providing additional support to the robustness of the top 300 list (FIG. 3), 293 were among the genes tested by Sonnichsen et al. and 257 had phenotypes (87.7%) including 176 Emb (embryonic lethal), 34 Lva (larval arrest), 34 Ste (sterile), 8 Lvl (larval lethal), 2 Stp (sterile progeny), 1 Bmd (body morphological defect), 1 Dpy (dumpy), 1 Egl (egg laying abnormal). 36 had wild type (WT) reports. Wild type reports increased toward the bottom of the list: 7 WT reports in 1-100, 13 WT in 101-200, 16 WT in 201-300.

RNAi phenotype reports were categorized into four groups. First, reports of lethality in the larval stages (lethal=let, larval lethal=lvl, larval arrest=lva) were placed together and given greatest weight. Such phenotypes if mimicked in *H. glycines* would be advantageous as dsRNA delivery from the plant to the nematode would begin as the second stage juvenile worm, a stage analogous to the dauer larva, enters the plant. Delivery would continue through development of J2, J3, and J4 juvenile or larval stages at the feeding site. Disrupting nematode physiology during these larval stages could prevent feeding site formation in the plant roots in the P0 (primary) generation.

Second, reports of molting (mlt), blistering (bli), and rupture (nip) defects were placed together and given second greatest weight. Such phenotypes are rare relative to other more commonly observed effects such as lethality or sterility. Nematodes, including both *C. elegans* and *H. glycines* are covered by a cuticle of collagen. Molting defects could block shedding and reformation of the cuticle between larval stages (J2→J3, J3→J4, J4→A) and therefore developmental progression. Blister phenotypes often also involve defects in the cuticle. Rupture phenotypes in *C. elegans* are not well understood but may involve loss of body integrity or osmotic shifts. Rupture phenotypes are particularly attractive for SCN control as they are likely irreversible with no opportunity for the worm to recover as may be the case for temporary blocks to metabolism or development.

Third, sterile (ste) and embryonic (emb) lethality phenotypes were placed together and given third greatest weight. In *C. elegans*, the germ line tissue, where many genes involved in fertility and embryonic development are active (maternal factors), is particularly sensitive to RNAi. In the context of an SCN infection, a sterile or embryonic lethal block to the lifecycle alone could prevent formation of a second generation but would allow initial feeding site formation and plant root system damage. Fourth, other major defects in the physiology including growth defective (gro), sick (sck), uncoordinated (unc), paralyzed (prl, prz) phenotypes were placed together and given fourth greatest weight. In the female *H. glycines*, once a feeding site is formed the worm discontinues moving and body wall musculature plays a limited role in survival. However, male worms become mobile as adults so that they can seek, find, and fertilize females. Therefore, blocking of muscle and nervous system structures important for normal movement could interfere with fertilization and formation of a second generation. For the purposes of this ranking, other non-lethal RNAi phenotypes (dumpy, short, long, body morphology defect, etc.) were not included. Phenotypes observed by genetic mutation were also not used in this ranking system.

To rank genes based on wormbase RNAi information, genes with multiple phenotypic reports and multiple different phenotypes were favored over genes with single phenotypic reports and single phenotypes. Multiple reports of phenotypes are helpful as they add confidence to the assignment of phenotype to a gene. Based on experiments from multiple groups, *C. elegans* RNAi experiments have a false negative and false positive rate of ~10-15%. Evidence of phenotypes from more than one report decreases the likelihood of inclusion of false positives in the list. Because *C. elegans* RNAi does not result in complete transcript elimination (knockdown is estimated at 90%) and is often non-uniform through the population, single gene RNAi experiments often result in the observation of multiple phenotypes over the course of the life cycle. Therefore, reporting of the phenotype of a given gene as "ste, emb, lvl" may mean that it is required throughout the lifecycle whereas a phenotype of "emb" alone may mean that the gene is only required for one step in embryonic development. For the purposes of parasite control, genes required for multiple steps and multiple processes in the lifecycle are more attractive targets than those required at just one stage as this provides more opportunities for a dsRNA to interfere with the lifecycle and block infection.

In each of these four categories, *C. elegans* RNAi reports were totaled and weighted. The first report of a phenotype in an N2 (wild type) background for a gene from a given laboratory was given a weight of 1. The second, third, etc. report of a phenotype from that same laboratory was given a discounted weight of 0.7. Therefore, independent reports from two laboratories (score=2) would be favored over two reports from the same laboratory (score=1.7) that might be vulnerable to a systematic error (e.g. wrong clone selected and used twice). Reports of phenotypes in the rrf-3(−/−) genetic background which is more sensitive to RNAi than N2 were given a discounted score of 0.6.

Figure 1:
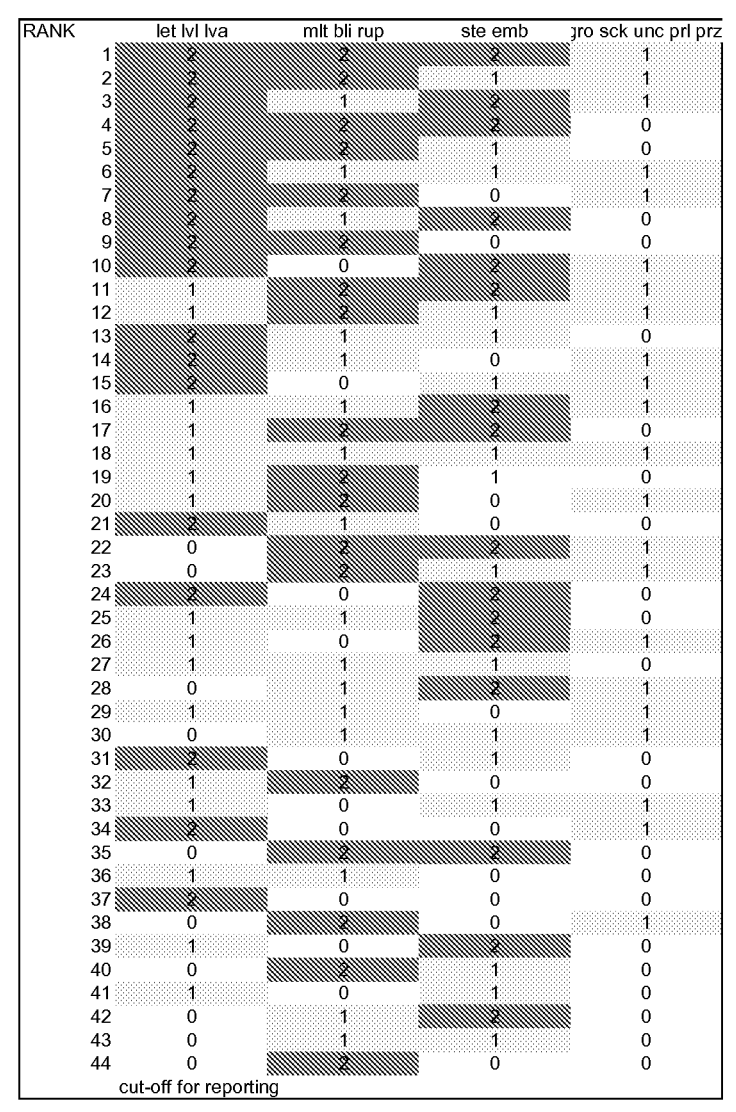

With these categories and weightings, targets were ranked on a scale from a score of 1 to 44 or higher based on their tally in the matrix shown in FIG. 1. For instance, to receive a score of 3, targets had to have a let lvl lva score of ≥2, a mlt bli nip score of X≥1, a ste emb score of ≥2, and an other phenotype score of ≥1. Most genes in *C. elegans* have a score worse than 44. 715 genes had a score of 44 or better and a potential homolog in *H. glycines*. For the top 300 targets, following ranking on all criteria, the average phenotype score was 22±9. The top score was a 3 (6 targets) and only 10 targets had a score less than 10. The most common categories were scores of 10 (61 targets with a let lvl lva score of ≥2, a mlt bli nip score of 0, a ste emb score of ≥2 and an other phenotype score of ≥1), 15 (23 targets), 24 (26 targets), 26 (93 targets), and 33 (19 targets). Averages and standard deviations for tallies in each category were let lvl lva score=1.9±1, mlt bli nip score=0.3±0.7, ste emb score=2.8±1.7, and an other phenotype score=1.6±1.3. mlt bli nip were the most rare phenotypes with only 56 targets having a score ≥0. Totals of targets with scores ≥0 in the other categories were 284 for let lvl lva, 281 for ste emb score of ≥2, and 258 for other phenotype.

In addition to reports of visible phenotypes from wormbase, reports of wild type (i.e. no phenotype) for each target were also recorded. Wild type findings were viewed as a negative for target ranking and most targets with high numbers of wild type reports were removed from consideration for the top 300 list. All wild type reports were given a score of 1 except those from Vidal et al. which were given a score of 0.3 since this group's methodology seems to have resulted in a higher percentage of wild type reports than all other reporting groups. In addition to total wild type tally, % wild type relative to all other reports was also calculated. For the top 300 targets, the averages and standard deviations for wild type tally and wild type percent were 0.14±0.41 and 1.9±5.1%. 250 of the 300 targets had no wild type reports. For the 50 targets with wild type reports, the wild type tally and percentages were 0.85±0.65 and 11.3±7.3%. In only 24 cases were wild type reports >10% of all reports with the highest being 33%.

Next, RNAi data was compared to that available in wormbase. RNAi experiments have been performed on more than 1,500 *C. elegans* genes of interest in feeding assays with N2, rrf-3, and other strains. Of the 715 *C. elegans* genes under consideration with BLAST amino acid homology to the *H. glycines* and wormbase phenotype scores of 44 or better (FIG. 1), information was available for about 75. Additionally, 3 genes with P0 (first generation) effects in assays not on the list of 715 were added to the list. 10 target genes of the original 715 showed no phenotype in an assay (multiple replicates with sequence confirmation of constructs) and were therefore excluded from the top 300. Phenotypes were observed for 39 target genes in the top 300 including lvl, lva, nip, ste, emb, unc, sck and additional phenotypes not included in the ranking system such as growth defective (gro), sterile progeny (stp), dumpy (dpy), and body morphology defect (bmd).

Example 2

C. elegans P-Zero (P0) RNAi Screens

In addition to the standard RNAi assay, additional *C. elegans* RNAi screens were performed. One of these was a P0 lethal screen.

P-Zero (P0) or Rapid Onset RNAi Effects in *C. elegans*

To control *Heterodera glycines* by providing dsRNA from a transgenic soy plant, finding genes that are sensitive to rapid onset RNAi effects could be useful. Such genes might block mature feeding site formation by the J2 while slow onset genes might not show an effect until the next generation. *C. elegans* genes where effects are seen in the exposed animal, so called P0 (P-zero) generation effects, might predict *H. glycines* orthologs with high and rapid sensitivity to RNAi.

All large scale screens for RNAi effects in *C. elegans* have exposed initial worms as L4s or adults (the genetic P0 (P-zero) generation) to dsRNA and looked for phenotypes in their progeny, the F1 and F2 generation. Sterility of the initial P0 animal was also observed in many cases. None of the microinjection screens (Gonczy et al., 2000; Piano et al. 2000; Piano et al., 2002) or feeding screens (Fraser et al., 2000; Kamath et al., 2003) note effects on the P0 animals other than sterility. Likewise, in a screen of over 1,200 *C. elegans* genes by feeding from L4 start, P0 phenotypes other than sterility were not observed. Wormbase (www.wormbase.org) records of RNAi phenotypes do not even note the generation in which an effect is observed (P0, F1, F2, etc.) so finding P0 candidates from these records is not possible. Maeda et al. 2000 performed RNAi on 2,500 *C. elegans* genes by soaking of L4s. Interestingly, in the supplementary online material accompanying the publication, Maeda et al. note 26 cases where P0 effects other than sterility were observed ranging from unhealthy to slow growing to lethality. These targets were investigated experimentally to see if any of the genes were actually legitimate P0 effects (FIG. 2).

Of the 26 Maeda et al. entries 21 corresponded to wormbase.org entries while 5 were clones of unclear origin. 19 genes have been successfully cloned into RNAi *E. coli* feeding constructs and sequence verified while 2 had cloning difficulties. 17 of the 19 completed clones have so far been tested for P0 phenotypes. Experiments are in progress to finish testing of two more clones and repeat test six others that have only been tested once to confirm results. Additionally, 7 targets of interest were tested in the same assay for a total of 24. Data was collected from two life-cycle starting points. First, a P0 L4 start was performed to mimic both the Maeda assay and the standard *E. coli* feeding assay. Second, a P0 egg start was performed to expose the P0 animal to dsRNA throughout development, a similar situation to that which may be encountered by a *Heterodera glycines* nematode upon infection of a plant producing a dsRNA. For the egg start, the assumption is that the first dsRNA exposure occurs as the L1 larva hatches and begins to feed.

From the 17 tested Maeda et al. (2001) candidates and 7 additional targets, 6 were found to have P0 phenotypes other than sterility from an egg start in the feeding assay (3 from Maeda and 3 from the additional list). These were Y57G11C.15 (sec61 alpha), C47E12.5 (uba-1), and R07E4.6 (kin-2) from Maeda and C34G6.6 (pan-1), F52B11.3 (pan-2), and T25C8.2 (act-5) from the additional list. For the L4 start, only three genes showed a P0 phenotypes other than sterility. The genes with L4 start phenotypes were a subset of the 6 showing an egg start phenotype: Y57G11C.15 (sec61 alpha) and R07E4.6 (kin-2) from Maeda and T25C8.2 (act-5) from the additional list. Of the remaining genes tested to date from the Maeda candidates, 4 had less severe phenotypes such as sterility and F1 larval arrest while 9 are fully wild type and were likely false positives in the Maeda screen. It remains possible however that genes lacking a phenotype in a bacterial feeding assay would have a phenotype in a soaking assay.

In addition to studies with N2 *C. elegans* worms (laboratory standard strain), studies were also performed for 22 of the genes in a fog-2(q71) mutant background. fog-2(q71) is a mutant that feminizes the germ line of the hermaphrodite and is maintained as a male/female strain. Female worms were picked away from males as larva prior to fertilization.

Such virgin female worms are easy to maintain for many days as they age since there is no F1 generation present to overgrow the plate and may therefore aid in seeing late onset effects in the P0 adult worm. P0 results observed in fog-2 (q71) were identical to those seen in N2 and no additional phenotypes were detected. fog-2 tests on subsequent genes were therefore discontinued.

The studies showed that in C. elegans obtaining a P0 phenotype other than sterility from an L4 start is a very rare event but that examples do exist such as Y57G11C.15 (sec61 alpha), R07E4.6 (kin-2), and T25C8.2 (act-5) (FIG. 2). Evidence suggests that most of the P0 phenotypes other than sterility recorded by Maeda et al. in their supplementary materials were false positives. This is supported by other evidence: in addition to the present data at least six genes had been tested by other laboratories and found to have only wild type phenotypes in all generations (P0, F1, etc.). P0 phenotypes other than sterility from an L4 start are presumably rare as the adult already has many of the proteins necessary for survival and the slow kinetics of RNAi takes time to degrade all transcripts. Genes showing an effect under such conditions may be ones where the worm is especially sensitive to their disruption and therefore ranked highly among targets for consideration. P0 phenotypes other than sterility from an egg start are less rare and are seen in several of the targets of interest known to have severe phenotypes (e.g. pan-1, pan-2). Presumably, a larger survey of targets with strong phenotypes would find more.

Of the six targets in which a P0 lethal phenotype was confirmed, all have reasonably strong orthologs among the H. glycines sequences kin-2 was already confirmed as having a P0 phenotype and was therefore ranked in the top 10. pan-1 and pan-2 are both already among the top 100 using our wormbase RNAi phenotype ranking system (FIG. 1) and additional H. glycines sequence information and will also be considered. Pan-1, which was missing from the ESTs, is newly identified in H. glycines based on Genome Survey sequencing. act-5, uba-1, and sec61 alpha were not yet among the top several hundred targets using the wormbase RNAi phenotype ranking system because they lacked let, lvl, lva, mlt, bli, and nip phenotype reports in wormbase. Final rank positions of these six targets among the top 300 are Y57G11C.15 (sec61 alpha)=#2, C47E12.5 (uba-1)=#3, and R07E4.6 (kin-2)=#4, C34G6.6 (pan-1)=#7, F52B11.3 (pan-2)=#30, and T25C8.2 (act-5)=#21.

Example 3

C. elegans Intestine-Specific RNAi Screen

A second additional screen was also performed to aid in the selection of target genes (Table 1). A strain of C. elegans that is sensitive to RNAi only in the intestine was previously generated. This strain can be used to rapidly screen the set of genes previously shown to be essential to viability and development by RNAi to identify those that are essential specifically in the intestine. Such genes may be advantageous targets with plant-delivered H. glycines RNAi as the intestine is believed to be the first tissue to come in contact with the entering dsRNA. Further, genes encoding secreted and transmembrane proteins may be vulnerable to disruption by the expression in the plant of nematocidal proteins that disrupt the function of these gene products.

The C. elegans intestine-specific RNAi strain was generated by introducing a transgene that drives expression of the wild-type sid-1 gene under the control of an intestine specific-promoter in an otherwise sid-1 minus background (Strain HC75). sid-1 is essential for systemic RNAi in C. elegans and encodes a transmembrane protein that is a putative dsRNA transporter (Winston, et al., 2002). Three lines, each driving expression from a different intestinal promoter, have been tested for sensitivity to RNAi. The promoters used are 5' regions of elt-2, ges-1, and ile-1. Feeding dsRNA from unc-54 (body wall muscle), dpy-7 (hypodermis), and act-1 (multiple tissues) showed no phenotype in these strains although all three dsRNAs produced the expected phenotype in wild-type (N2) worm controls. On the other hand, feeding dsRNA from act-5, an intestine-specific actin, and ile-1, a gene with intestinal localization, in these strains resulted in sterility. These observations support the conclusion that these strains are sensitive to RNAi in the intestine but not in a number of other tissues. The ges-1::sid-1 strain was selected for screening. Phenotypes in this strain are weaker than in N2 even for genes that only have roles in the intestine, probably because ges-1 expression is non-uniform or weaker than endogenous SID-1 intestinal expression such that SID-1 is not always present at the levels it would be in N2. However, phenotypes, such as 50% sterility are easily scored relative to controls and are reproducible. 130 genes have been examined to date in the intestinal-RNAi strain, with a focus on secreted and transmembrane targets and 57 have been observed to have phenotypes (Table 1). Of the 715 gene targets under consideration for the top 300 list, 24 had phenotypes in the intestinal RNAi strain whereas 3 were wild type. In ranking otherwise equally weighted targets preference was given to genes showing intestinal RNAi strain phenotypes and 14 such genes made the top 300 list. The 10 that did not either had weak intestinal RNAi phenotypes (e.g. 25% sterile) or other drawbacks (weak homology, non-orthology, etc.).

TABLE 1

C. elegans Intestinal RNAi Strain Phenotypes

| Gene | Intestinal RNAi Phenotype | Gene | Intestinal RNAi Phenotype |
| --- | --- | --- | --- |
| act-5 | 80% sterile | C01G8.5 | 40% sterile |
| Ile-1 | 80% sterile | R13H4.4 | 30% sterile |
| C16A3.3 | 20-70% sterile | C25A11.4 | 40% sterile |
| C47E12.5 | 40-99% sterile | T26E3.3 | 15% sterile |
| C48E7.6 | 20-40% sterile | F54G8.3 | 20% sterile |
| D1014.3 | 30-80% sterile | ZK1058.2 | 50-80% sterile |
| D1069.3 | 15-50% sterile | K07D8.1 | 25% sterile |
| T10H9.3 | 20-40% sterile | H19M22.2 | 45% sterile |
| T24H7.1 | 15-35% sterile | F42C5.10 | 65% sterile |
| ZK973.6 | 20-30% sterile | T03E6.7 | EMB |
| C01F1.2 | 15-40% sterile | R03E1.2 | 75% sterile |
| C54G4.8 | 50-80% sterile | Y55H10A.1 | LVA, 80% sterile |
| F10D7.5 | 15-40% sterile | C23H3.4 | 80% sterile |
| F11G11.5 | 15-50% sterile | F43D9.3 | 55% sterile |
| F32B5.8 | 20-25% sterile | Y57G11C.15 | 80% sterile |
| F33A8.1 | 60-97% sterile | F49C12.13 | 55% sterile |
| F34D10.2 | 20-30% sterile | T01H3.1 | 60% sterile |
| F39B2.11 | 20-25% sterile | T04A8.9 | 20-80% sterile |
| F54C9.2 | 15-25% sterile | H19M22.2 | 45-55% sterile |
| F55A11.2 | 10-15% sterile | K02B12.3 | 20-50% sterile |
| F55A12.7 | 50-60% sterile | W04A4.5 | 25-50% sterile |
| F55A12.8 | 20% sterile | Y47G6A.23 | 25-50% sterile |
| F55F10.1 | 20-25% sterile | C16D9.2 | 30-35% sterile |
| K07A12.3 | 15-25% sterile | F52C6.3 | 35% sterile |
| K07B1.5 | 25-30% sterile | F53B8.1 | 65% sterile |
| K07D8.1 | 25% sterile | C49C3.11 | 35% sterile |
| K12D12.2 | 40-70% sterile | F41G3.4 | 35% sterile |
| R04F11.2 | 40-70% sterile | Y57G11C.31 | 25% sterile |
| T01B11.3 | 10-30% sterile | | |

Example 4

Information on the C. elegans Gene Orthologs—Putative Molecular Function

Besides phenotype, additional information extracted from wormbase included gene name, wormpep protein ID, expression pattern, subcellular localization, prominent motifs, brief identification, concise description, and gene ontology terms. Preference for ranking was given to target genes with known molecular function over those with completely unknown function. We observed that genes with strong phenotypes were in general those with protein products involved in core cellular processes such as DNA replication, cell cycle, transcription, RNA processing, translation including ribosome and tRNA function, protein trafficking, secretion, protein modification, protein stability and degradation, energy production including mitochondrial function, intermediary metabolism, cell structure, signal transduction, channels and transporters, and endocytosis. Of the 300 selected targets, 275 belong to one of these categories (Table 2). Of the top 100, 98 belonged to one of these categories. The most frequently observed categories among targets with strong phenotypes were translation/ribosome/tRNAs, transcription/RNA processing, and Protein stability/degradation/proteosome.

complex may result in complex misassembly or other functional failure. Recent findings in *S. cerevisiae* support this interpretation (Papp et al., 2003).

Example 5

Sequence Homology, Identity, and Orthology Assignment

To identify *Heterodera glycines* orthologs of characterized *C. elegans* genes, homology searches were performed using the BLAST suite of programs (Altschul et al., 1990). Using predicted protein sequences for *C. elegans* genes (Wormpep) TBLASTN was used to search both *H. glycines* clustered ESTs and other sequences available from Genbank as well as recently generated proprietary genome survey sequences. Bitscore, e-value, and % identity were tracked. For consideration as a target, a *C. elegans* gene had to have a TBLASTN match to an ortholog or homolog in *H. glycines* with an e-value of at least e-10 or better. 715 *C. elegans* genes with RNAi phenotypes ranking from 1-44 (FIG. 1) met this minimal criterion. For these 715 genes, *H. glycines* matches were:

TABLE 2

Categorization of *C. elegans* 300 Top Targets by Putative Cellular Function

|   | DNA replication, repair, modify, cell cycle, chromatin | Transcription/ RNA processing | Translation/ ribosome/ tRNAs | Protein trafficking/ secretion/ nuclear import/ export | Protein modification | Protein stability/ degradation/ proteosome | Energy production/ mitochondria | Metabolism/ Other Enzymes | Cell structure/ extracellular matrix | Receptors/ Signal transduction/ kinases | Channels/ Transporters | Endocytosis | Other/ Unknown |
|---|---|---|---|---|---|---|---|---|---|---|---|---|---|
| totals 1-300 | 22 | 41 | 65 | 22 | 3 | 31 | 14 | 28 | 21 | 20 | 1 | 8 | 25 |
| % | 7% | 14% | 22% | 7% | 1% | 10% | 5% | 9% | 7% | 7% | 0% | 3% | 8% |
| 1-100 | 7 | 13 | 14 | 4 | 2 | 13 | 8 | 13 | 8 | 11 | 0 | 6 | 2 |
| 101-200 | 5 | 14 | 34 | 6 | 0 | 11 | 3 | 8 | 6 | 4 | 0 | 1 | 8 |
| 201-300 | 10 | 14 | 17 | 12 | 1 | 7 | 3 | 7 | 7 | 5 | 1 | 1 | 15 |

Tracking of putative cellular function insures that suitable diversity is maintained in the top targets list and that the target list does not become too dependent upon one or a few processes which might function differently in *H. glycines* than *C. elegans*. In conception, low priority is given to developmental processes believed to be rapidly evolving in nematodes such as sex determination since such processes are less likely to be conserved between *H. glycines* and *C. elegans*. In practice, few such genes scores well enough in RNAi phenotype to come into consideration for the top 300 list. Interestingly, considering strength of *C. elegans* phenotype alone (score from 1-44 and wild type reports) even prior to inclusion of information on sequence conservation, highly ranked targets greatly over represent core cellular processes involving large multi-subunit complexes such as the ribosome and proteosome. This may result simply from the importance of translation and protein degradation to cellular survival. One additional interpretation of this finding is that subunits of large complexes tend to have strong phenotype following RNAi knockdown as they are more dosage sensitive than proteins not acting in complexes. For example, while a monomer enzyme may retain adequate flux through a metabolic pathway with only 10% of its normal protein dose, imbalance between subunit doses in a large

| BLAST | Mean ± SD | Range |
|---|---|---|
| % ID | 56 ± 18 | 96-22 |
| Bitscore | 184 ± 141 | 1031-52 |
| E-value | e−48 (median) | 0-e−11 |

To build the top 300 list (FIG. 3), favorable amino acid level sequence similar between *C. elegans* and *H. glycines* was the second most important factor in ranking after RNAi phenotype. Targets features of % ID, bitscore, and e-value were divided into quartiles. Top ranking targets in addition to having strong RNAi phenotypes also had favorable homology features indicative of orthology: bitscore (>100), e-value (<e-20), and percentage identity (>40%). To insure orthology assignment, targets were also tested for reciprocal BLAST matching so that when the selected *H. glycines* sequence was checked by BLAST back to the *C. elegans* wormpep list (BLASTX), the original starting sequence was identified. 25 genes that would otherwise have made the top 300 failed this reciprocal BLAST test indicating that the genes in *C. elegans* and *H. glycines* were unlikely to be orthologs. Of the final 300, 296 appeared to be clear orthologs with reciprocal BLAST top matches in both directions, 1 was tied for top match (2 close homologs in *C. elegans*), and 3 were within 5% of the top bitscore (these were kept because of strong phenotypes among all the top *C. elegans* homologs). For the top 300 genes, *H. glycines* matches were:

| BLAST | Mean ± SD | Range |
|---|---|---|
| % ID | 65 ± 15 | 96-30 |
| Bitscore | 253 ± 158 | 1031-71 |
| E-value | e−61 (median) | 0-e−13 |

Of the top 300 targets, 63 appear to have been identified specifically due to Genome Survey sequencing. Matches in the ESTs or other publicly available sequences are either missing or of substantially weaker scores (mostly paralogs). The rank of these genes among the top 300 is as follows:
23 in top 100: 1, 5, 7, 9, 15, 33, 35, 37, 38, 40, 44, 51, 53, 58, 60, 67, 68, 75, 80, 82, 83, 88, 96
15 in 2nd 100: 102, 115, 134, 142, 148, 151, 152, 156, 163, 164, 191, 193, 199, 200
26 in 3rd 100: 206, 208, 211, 219, 226, 231, 237, 241, 242, 247, 251, 254, 256, 258, 260, 261, 263, 267, 271, 272, 280, 281, 289, 292, 298, 300.

Example 6

Gene Expression in *H. glycines* and Other Tylenchids

The expression of target genes in *H. glycines* and other Tylenchid plant parasitic nematodes was also monitored. Even within *H. glycines*, this process was imprecise since the identified transcript from the top 300 list may be the actual gene of interest in the cases where the top hit was an EST (237 out of 300) or a related homolog where the top match was to the genomic sequence (63 out of 300). Likewise, matches in related Tylenchids may be orthologs or homologs. Nevertheless, this information provides a starting point for looking at stage of expression. Expression in J2, J3, and J4 is particularly attractive as double stranded RNA delivery should be possible from the plant at these stages through the feeding site while the cyst is forming. Of genes with EST representation in *H. glycines*, 47% were represented by a single EST. 53% of genes were represented by two or more ESTs. 64% had representation in stages J2, J3, or J4. 165 of the 300 targets had orthologs or homologs among ESTs and other sequencing available from other Tylenchid plant parasitic nematodes including *Heterodera schachtii*, *Globodera rostochiensis*, *Globodera pallida*, *Meloidogyne incognita*, *Meloidogyne javanica*, *Meloidogyne arenaria*, *Meloidogyne hapla*, *Meloidogyne chitwoodi*, *Meloidogyne paranaensis*, *Pratylenchus vulnus*, *Pratylenchus penetrans*, *Radopholus similis* (Table 3).

TABLE 3

Evidence of Expression of Top 300 Targets in *H. glycines* and other Tylenchid species.

|  | total H.g ESTs | J2, J3, J4 H.g ESTs | Total ESTs Other Species |
|---|---|---|---|
| mean | 4.7 | 2.3 | 14.0 |
| sd | 22.0 | 5.3 | 64.3 |
| median | 1 | 1 | 1 |
| zeros | 22 | 122 | 135 |
| ones | 131 | 66 | 38 |
| twos | 43 | 46 | 12 |
| three or more | 102 | 64 | 113 |

Example 7

Target List for *H. glycines* RNAi

Disruption of target gene function within the plant pathogen soybean cyst nematode, *Heterodera glycines*, can be accomplished by RNA interference and can result in disruption of the pathogen's lifecycle. Optimal target genes for disruption include life-cycle essential genes where disruption results in high penetrance death of the parasite populations or "genetic death" by blocking of reproduction with minimal damage to the plant and minimal viable escaping worms reaching the next generation. The inventors have provided a process for selecting RNAi targets and a list of 300 target genes predicted to be essential to *H. glycines* reproduction. Key features used to predict targets include orthology to *C. elegans* known genes with strong and reproducible RNA interference phenotypes. The complete top 300 target list is provided in FIG. 3. Table 4 lists selected gene targets for assaying in plant tissues.

TABLE 4

Selected Gene Targets for Soybean Hairy Root and in planta Assays

| Gene Name | Matching Nucleotide Sequence | Location on Nucleotide Sequence | Peptide Sequence |
|---|---|---|---|
| Bli-3 | SeqID_1304 | 12-552 | SeqID_1889 |
| Bli-3 | SeqID_1487 | 12-552 | SeqID_1889 |
| C23H3.4 | SeqID_510 | 925-735 | SeqID_1056 |
| C23H3.4 | SeqID_814 | 586-776 | SeqID_1056 |
| C26E6.4 | SeqID_539 | 2836-3029 | SeqID_1051 |
| C34G6.6 | SeqID_511 | 3917-3429 | SeqID_1233 |
| C34G6.6 | SeqID_790 | 244-732 | SeqID_1233 |
| Cct-4 | SeqID_1318 | 193-568 | SeqID_1741 |
| Cct-4 | SeqID_1537 | 193-568 | SeqID_1741 |
| Cgh-1 | SeqID_1289 | 319-795 | SeqID_1722 |
| Cgh-1 | SeqID_1513 | 280-756 | SeqID_1722 |
| Cgh-1 | SeqID_1289 | 1587-1761 | SeqID_1722 |
| Crs-1 | SeqID_535 | 1783-1487 | SeqID_1035 |
| Crs-1 | SeqID_792 | 1353-1649 | SeqID_1035 |
| Cyc-1 | SeqID_513 | 1375-1154 | SeqID_1046 |
| Cyc-1 | SeqID_804 | 529-750 | SeqID_1046 |
| F01G10.1 | SeqID_509 | 3122-3454 | SeqID_1055 |
| F01G10.1 | SeqID_813 | 690-1022 | SeqID_1055 |
| F52B11.3 | SeqID_508 | 3280-3088 | SeqID_1053 |
| F52B11.3 | SeqID_811 | 1036-1228 | SeqID_1053 |
| F54B3.3 | SeqID_524 | 2457-2222 | SeqID_1058 |
| F54B3.3 | SeqID_816 | 266-501 | SeqID_1058 |
| Kin-2 | SeqID_506 | 1310-1023 | SeqID_1032 |
| Kin-2 | SeqID_787 | 79-366 | SeqID_1032 |
| Kin-2 | SeqID_1921 | 15-464 | SeqID_1931 |
| Kin-2 | SeqID_1921 | 465-714 | SeqID_1931 |
| Kin-2 | SeqID_1926 | 211-460 | SeqID_1931 |
| Kin-2 | SeqID_787 | 265-514 | SeqID_1032 |
| Kin-2 | SeqID_787 | 514-663 | SeqID_1032 |
| Kin-2 | SeqID_1921 | 340-586 | SeqID_1931 |
| Kin-2 | SeqID_1926 | 86-332 | SeqID_1931 |
| Kin-2 | SeqID_787 | 140-386 | SeqID_1032 |
| Let-767 | SeqID_1306 | 328-687 | SeqID_1735 |

TABLE 4-continued

Selected Gene Targets for Soybean Hairy Root and in planta Assays

| Gene Name | Matching Nucleotide Sequence | Location on Nucleotide Sequence | Peptide Sequence |
|---|---|---|---|
| Let-767 | SeqID_1528 | 295-654 | SeqID_1735 |
| Pas-4 | SeqID_1292 | 564-894 | SeqID_1724 |
| Pas-6 | SeqID_1290 | 314-859 | SeqID_1723 |
| Ran-1 | SeqID_1307 | 550-777 | SeqID_1736 |
| Rpt-1 | SeqID_1310 | 328-581 | SeqID_1737 |
| Rpt-1 | SeqID_1531 | 328-581 | SeqID_1737 |
| Rpt-1 | SeqID_523 | 1356-1609 | SeqID_1047 |
| Rpt-1 | SeqID_805 | 668-921 | SeqID_1047 |
| Sec61 alpha | SeqID_1330 | 93-488 | SeqID_1751 |
| Sec61 alpha | SeqID_1548 | 93-488 | SeqID_1751 |
| Top-1 | SeqID_1298 | 1-449 | SeqID_1729 |
| Top-1 | SeqID_1521 | 1-449 | SeqID_1729 |
| Top-1 | SeqID_1920 | 1569-2017 | SeqID_1930 |
| Top-1 | SeqID_1925 | 1565-2013 | SeqID_1930 |
| Uba-1 | SeqID_1923 | 1977-2184 | SeqID_1933 |
| Uba-1 | SeqID_1928 | 1715-1922 | SeqID_1933 |
| Uba-1 | SeqID_505 | 2500-2708 | SeqID_1031 |
| Uba-1 | SeqID_786 | 1562-1770 | SeqID_1031 |
| Vab-10 | SeqID_542 | 2871-3759 | SeqID_1028 |
| Vab-10 | SeqID_788 | 444-1332 | SeqID_1028 |
| Vha-12 | SeqID_1303 | 44-496 | SeqID_1733 |
| Vha-12 | SeqID_1526 | 1-453 | SeqID_1733 |
| Vha-12 | SeqID_793 | 1-453 | SeqID_1036 |
| Vha-13 | SeqID_1312 | 16-255 | SeqID_1906 |
| Vha-13 | SeqID_1533 | 16-255 | SeqID_1906 |
| Vha-13 | SeqID_514 | 1979-2218 | SeqID_1048 |
| Vha-13 | SeqID_806 | 707-946 | SeqID_1048 |
| Vha-15 | SeqID_519 | 1318-1137 | SeqID_1033 |
| Vha-15 | SeqID_789 | 997-1178 | SeqID_1033 |
| Y48B6A.3 | SeqID_1302 | 1755-2384 | SeqID_1732 |
| Y48B6A.3 | SeqID_1525 | 1697-2326 | SeqID_1732 |
| Y55H10A.1 | SeqID_1327 | 524-830 | SeqID_1748 |
| Y55H10A.1 | SeqID_1545 | 524-830 | SeqID_1748 |
| ZK1127.5 | SeqID_538 | 285-535 | SeqID_1050 |
| ZK1127.5 | SeqID_808 | 50-300 | SeqID_1050 |

Example 8

Selected *H. glycines* Genes Showing Efficacy in Blocking Soybean Cyst Nematode Infection of Soybean Results from soaking assays show that orthologs (and fragments of such orthologs) of pas-4 (e.g. found at nucleotides 1-544 of SEQ ID NO:1292), pas-5 (e.g. found in SEQ ID NOs:525, 569, 797, nucleotides 1-672 of SEQ ID NO:1293, or in SEQ ID NO:1516), pas-6 (e.g. found at nucleotides 314-859 of SEQ ID NO:1290), and cgh-1 (e.g. found at nucleotides 931-1567 of SEQ ID NO:1289), among others, demonstrate efficacy in blocking soybean cyst nematode (SCN) reproduction. Each of these genes are found among the top 16 entries in FIG. 3.

Selected genes or gene fragments were also tested in a soybean hairy root assay (e.g. Narayanan et al., 1999), and plant tissues demonstrated resistance to SCN as shown in Table 5:

TABLE 5

| Hairy root assay results demonstrating SCN resistance activity. | | | | | | |
|---|---|---|---|---|---|---|
| Gene Name | Locus | Class I | Class II | Class III | Class IV | Total Exp |
| Sec61 alpha | Y57G11C.15 | 2 | 1 | 2 | 0 | 7 |
| Uba-1 | C47E12.5 | 8 | 2 | 2 | 0 | 16 |
| Kin-2 | R07E4.6 | 20 | 8 | 3 | 4 | 32 |
| Vab-10 | ZK1151.1 | 1 | 1 | 2 | 0 | 7 |
| Vha-15 | T14F9.1 | 4 | 2 | 1 | 0 | 8 |
| C34G6.6 | C34G6.6 | 1 | 2 | 0 | 1 | 7 |
| Y48B6A.3 | Y48B6A.3 | 0 | 1 | 0 | 0 | 2 |
| Crs-1 | Y23H5A.7 | 1 | 0 | 0 | 0 | 2 |
| Vha-12 | F20B6.2 | 0 | 1 | 0 | 0 | 4 |
| Pas-4 | C36B1.4 | 2 | 0 | 0 | 0 | 6 |
| Bli-3 | F56C11.1 | 3 | 0 | 0 | 0 | 3 |
| Cgh-1 | C07H6.5 | 1 | 0 | 0 | 1 | 9 |
| Let-767 | C56G2.6 | 3 | 0 | 1 | 0 | 4 |
| Pas-6 | CD4.6 | 2 | 5 | 0 | 1 | 7 |
| Ran-1 | K01G5.4 | 2 | 2 | 0 | 0 | 5 |
| Cyc-1 | C54G4.8 | 1 | 0 | 0 | 0 | 2 |
| Rpt-1 | C52E4.4 | 2 | 0 | 0 | 0 | 6 |
| Vha-13 | Y49A3A.2 | 3 | 2 | 1 | 0 | 8 |
| Top-1 | M01E5.5 | 18 | 8 | 2 | 4 | 26 |
| ZK1127.5 | ZK1127.5 | 0 | 2 | 0 | 0 | 2 |
| C26E6.4 | C26E6.4 | 1 | 1 | 1 | 0 | 3 |
| F52B11.3 | F52B11.3 | 2 | 1 | 1 | 0 | 3 |
| F01G10.1 | F01G10.1 | 6 | 1 | 3 | 1 | 10 |
| C23H3.4 | C23H3.4 | 2 | 1 | 0 | 0 | 5 |
| Cct-4 | K01C8.10 | 3 | 1 | 0 | 0 | 4 |
| F54B3.3 | F54B3.3 | 0 | 1 | 0 | 0 | 2 |
| Y55H10A.1 | Y55H10A.1 | 3 | 1 | 1 | 0 | 6 |

Classification of Efficacy for Table 5

Class IV: greater than or equal to 50% reduction in mean cyst number relative to mean cyst number for transgenic empty vector wild type control;

Class III: 35-49% reduction in mean cyst number relative to mean cyst number for transgenic empty vector wild type control;

Class II: 20-34% reduction in mean cyst number relative to mean cyst number for transgenic empty vector wild type control Class I: having individual transformation events with greater efficacy than highest event efficacy seen with transgenic empty vector wild type control Transgenic soybean plants were prepared expressing fragments of genes encoding, for instance, Pas-4, Pas-5, Cgh-1, or Pas-6, and these plants were tested for SCN resistance. Results are shown in Table 6, demonstrating efficacy in reducing SCN infection and/or reproduction.

TABLE 6

| Transgenic plant analysis for SCN resistance | | | | | | | | |
|---|---|---|---|---|---|---|---|---|
| Gene Name | Locus | Pro-moter | Soy line | Class I | Class II | Class III | Class IV | Total Events tested |
| Pas-4 | C36B1.4 | FMV | Lee 74 | 6 | 3 | 1 | 0 | 12 |
| | | | A3244 | 6 | 2 | 0 | 0 | |
| Pas-5 | F25H2.9 | FMV | Lee 74 | 4 | 5 | 5 | 1 | 18 |
| | | | A3244 | 0 | 1 | 0 | 0 | |
| Pas-5 | F25H2.9 | E35S | Lee 74 | 2 | 4 | 4 | 2 | 16 |
| | | | A3244 | 1 | 1 | 1 | 0 | |

TABLE 6-continued Transgenic plant analysis for SCN resistance

| Gene Name | Locus | Promoter | Soy line | Class I | Class II | Class III | Class IV | Total Events tested |
|---|---|---|---|---|---|---|---|---|
| Cgh-1 | C07H6.5 | FMV | Lee 74 | 4 | 2 | 2 | 2 | 11 |
| | | | A3244 | 0 | 2 | 1 | 1 | |
| Cgh-1 | C07H6.5 | E35S | Lee 74 | 5 | 13 | 2 | 2 | 27 |
| | | | A3244 | 6 | 2 | 0 | 2 | |
| Pas-6 | CD4.6 | FMV | Lee 74 | 5 | 1 | 2 | 1 | 14 |
| | | | A3244 | 1 | 1 | 2 | 0 | |
| Pas-6 | CD4.6 | E35S | Lee 74 | 7 | 5 | 0 | 0 | 20 |
| | | | A3244 | 3 | 1 | 0 | 0 | |

Classification of Efficacy for Table 6:
Class I: 10-20% reduction in mean cyst number relative to mean cyst number for Lee 74 or A3244;
Class II: 20-35% reduction in mean cyst number relative to mean cyst number for Lee 74 or A3244;
Class III: 36-50% reduction in mean cyst number relative to mean cyst number for Lee 74 or A3244;
Class IV: >50% reduction in mean cyst number relative to mean cyst number for Lee 74 or A3244

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references are incorporated herein by reference:
U.S. Pat. No. 4,536,475; U.S. Pat. No. 4,693,977; U.S. Pat. No. 4,886,937; U.S. Pat. No. 4,940,838; U.S. Pat. No. 4,959,317; U.S. Pat. No. 5,015,580; U.S. Pat. No. 5,107,065; U.S. Pat. No. 5,110,732; U.S. Pat. No. 5,231,020; U.S. Pat. No. 5,283,184; U.S. Pat. No. 5,302,523; U.S. Pat. No. 5,384,253; U.S. Pat. No. 5,464,763; U.S. Pat. No. 5,464,765; U.S. Pat. No. 5,501,967; U.S. Pat. No. 5,508,184; U.S. Pat. No. 5,527,695; U.S. Pat. No. 5,538,880; U.S. Pat. No. 5,459,252; U.S. Pat. No. 5,550,318; U.S. Pat. No. 5,563,055; U.S. Pat. No. 5,591,616; U.S. Pat. No. 5,593,874; U.S. Pat. No. 5,633,435; U.S. Pat. No. 5,693,512; U.S. Pat. No. 5,698,425; U.S. Pat. No. 5,712,135; U.S. Pat. No. 5,759,829; U.S. Pat. No. 5,780,708; U.S. Pat. No. 5,789,214; U.S. Pat. No. 5,804,693; U.S. Pat. No. 5,824,877; U.S. Pat. No. 5,837,848; U.S. Pat. No. 5,981,840; U.S. Pat. No. 6,118,047; U.S. Pat. No. 6,160,208; U.S. Pat. No. 6,326,193; U.S. Pat. No. 6,384,301; U.S. Pat. No. 6,399,861; U.S. Pat. No. 6,403,865; U.S. Pat. No. 6,506,559
U.S. patent application Ser. No. 10/465,800; U.S. patent application Ser. No. 11/360,355
U.S. Pub. 2002/0048814; U.S. Pub. 2003/0018993; U.S. Pub. 2003/0061626; U.S. Pub. 2003/0150017; U.S. Pub. 2003/0175965; U.S. Pub. 2004-0029283; U.S. Pub. 2004/0098761; U.S. Pub. 2004/0133943; U.S. Pub. 2005/0188438; U.S. Pub. 2006/0037101; US Pub. 2006/0200878 A1
Aboobaker and Blaxter, *Mol. Biochem. Parasitol.*, 129:41-51, 2003.
Altschul et al., *J. Mol. Biol.*, 215:403-410, 1990.
Ashrafi et al., *Nature,* 421:268-72, 2003.
Ausubel et al., In: *Current Protocols in Molecular Biology*, John, Wiley & Sons, Inc, New York, 1998.
Barker et al., In: *Plant and Soil Nematodes: Societal Impact and Focus for the Future*, Comm. Natl. Needs Priorities Nematol., Cooperative State Research Service, US Dept. Arig. Soc. Nematologists, 1994.
Bevan et al., *Nature,* 304:184-187, 1983.
Böckenhoff and Grundler *Parasitology* 109: 249-254, 1994.
Böckenhoff et al. *Plant Physiol* 112:1421-7, 1996.
Broothaerts et al., *Nature*, 433:629-633, 2005.
Brutlag et al., *Computers and Chemistry,* 17:203-207, 1993.
De Meutter et al. *Mol Plant Path* 6:321-325, 2005.
Dellaporta et al., In: *Chromosome Structure and Function: Impact of New Concepts*, 18th Stadler Genetics Symposium, 11:263-282, 1988.
Elbashir et al., *Genes Dev.,* 5(2):188-200, 2001.
EP 0 120 516
EP 0 122 791
Fairbairn et al., "Plant Delivered RNAi (PD-RNAi): A novel strategy to control plant parasitic nematodes by inactivating nematode genes in planta", (Annual Meeting Abstract #372) American Society for Plant Biology, 2005.
Fire et al., *Nature,* 391(6669):806-811, 1998.
Fraser et al., *Nature,* 408:325-330, 2000.
Gheysen and Fenoll, *Annu. Rev. Phytopathol.* 40:191-219, 2002.
Gonczy et al., *Nature,* 408:331-336, 2000.
Gruber et al., In: *Vectors for Plant Transformation*, Methods in Plant Molecular Biology and Biotechnology, Glick and Thompson (Eds.), CRC Press, Inc., Boca Raton, 89-119, 1993.
Hamilton and Baulcombe, *Science,* 286:950-952, 1999.
Hannon, *Nature,* 418:244-251, 2002
Haymes et al., In: *Nucleic acid hybridization, a practical approach*, IRL Press, Washington, D.C., 1985.
Herrera-Estrella et al., *Nature,* 303:209-213, 1983.
Hirel et al., *Plant Molecular Biology,* 20:207-218, 1992.
Horsch et al., *Science,* 227:1229, 1985.
Hoth et al. *Plant Physiol* 138:383-392, 2005.
Hussein et al., *Mol. Biochem. Parasitol.,* 122:91-94, 2002.

Ikatu et al., *Bio/Technol.*, 8:241-242, 1990.
Jefferson et al., *EMBO J.*, 6:3901-3907, 1987.
Juergensen et al. *Plant Physiol* 131:61-69, 2003.
Kaeppler et al., *Plant Cell Rep.*, 8:415-418, 1990.
Kamath et al., *Genome Biol.*, 2:R02, 2001.
Kamath et al., *Nature*, 421:231-237, 2003.
Katz et al., *J. Gen Microbiol.*, 129:2703-2714, 1983.
Klee et al., *Bio/Technol.*, 3:637-642, 1985.
Kwa et al., *J. Mol. Biol.*, 3:246:500-510, 1995.
Lustigman et al., *Mol. Biochem. Parasitol.*, 138:165-70, 2004.
Maeda et al., *Curr. Biol.*, 11:171-176, 2001.
Mazarei et al. *Mol Plant Path* 5:409-423, 2004.
Martinez et al., *Cell*, 110:563-574, 2002.
McCarter et al., *Genome Biology*, 4:R26, 1-19, 2003.
McCarter, *Trends in Parasitology*, 20:462-468, 2004.
McManus and Sharp, *Nat. Rev. Genet.*, 3:737-47, 2002.
Miki et al., In: *Procedures for Introducing Foreign DNA into Plants*, Methods in Plant Molecular Biology and Biotechnology, Glick and Thompson (Eds.), CRC Press, Inc., Boca Raton, 67-88, 1993.
Moloney et al., *Plant Cell Reports*, 8:238, 1989.
Narayanan et al., *Crop Sci.* 39:1680-1686, 1999.
Odell et al., *Nature*, 313:810-812, 1985.
Omirulleh et al., *Plant Mol. Biol.*, 21:415-428, 1993.
Opperman et al., *Science* 263:221-223, 1994.
Ow et al., *Science*, 234:856-859, 1986.
Padgette et al., *Crop Sci.*, 35:1451-1461, 1995.
Papp et al., *Nature*, 424:194-197, 2003.
Parkinson et al., *Nature Genetics*, 36:1259-1267, 2004.
PCT Appln. WO 06/073727
PCT Appln. WO 05/019408
PCT Appln. WO 03/052110 A2.
PCT Appln. WO 97/32016
PCT Appln. WO 99/49029
PCT Appln. WO 99/53050
PCT Appln. WO94/01550
PCT Appln. WO98/05770
Piano et al., *Curr Biol.*, 10:1619-1622, 2000.
Piano et al., *Curr Biol.*, 12:1959-64, 2002.
Potrykus et al., *Mol. Gen. Genet.*, 199:183-188, 1985.
Redmond et al., *Mol. Biochem. Parasitol.*,112:125-31, 2001.
Reynolds et al. *Nat Biotechnol.* 22:326-330, 2004.
Sambrook et al., (ed.), *Molecular Cloning*, Cold Spring Harbor Laboratory Press, Cold Spring Harbor, N.Y., 1989.
Simmer et al., *PLoS Biol.*, 1:E12, 2003.
Sonnichsen et al., *Nature*, 434:462-469, 2005.
Sutcliffe, *Proc. Natl. Acad. Sci. USA*, 75:3737-3741, 1978.
Thurau et al. *Plant Mol Biol* 52:643-660, 2003.
Urwin et al., *Mol. Plant Microbe. Interact.*, 15:747-752, 2002.
Vaghchhipawala et al. *Genome* 47:404-413, 2004.
Van Heeke and Schuster, *J. Biol. Chem.*, 264:5503-5509, 1989.
Winston et al., *Science*, 295:2456-2459, 2002.
Zukowski et al., *Proc. Natl. Acad. Sci. USA*, 80:1101-1105, 1983.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09988642B2). An electronic copy of the "Sequence Listing" will also be available from the USPTO upon request and payment of the fee set forth in 37 CFR 1.19(b)(3).

What is claimed is:

1. A method for controlling a plant-parasitic nematode population comprising providing an agent comprising a double stranded ribonucleotide sequence that functions upon being taken up by the nematode to inhibit a biological function of Top-1 within said nematode, wherein the double stranded ribonucleotide sequence comprises at least 21 contiguous nucleotides of a nucleotide sequence selected from the group consisting of SEQ ID NO:1298, SEQ ID NO:1521, SEQ ID NO:1920, or SEQ ID NO:1925, wherein said nematode is *Heterodera glycines*.

2. A method for controlling a plant-parasitic nematode population comprising providing an agent comprising a first polynucleotide sequence that functions upon being taken up by the nematode to inhibit a biological function of Top-1 within said nematode, wherein said first polynucleotide sequence exhibits from about 95 to about 100% nucleotide sequence identity along at least 21 contiguous nucleotides of a coding sequence derived from said nematode and is hybridized to a second polynucleotide sequence that is complementary to said first polynucleotide sequence, and wherein said coding sequence derived from said nematode is selected from the group consisting of SEQ ID NO:1298, SEQ ID NO:1521, SEQ ID NO:1920, or SEQ ID NO:1925, wherein said nematode is *Heterodera glycines*.

3. A method of controlling plant nematode pest infestation in a plant comprising providing in the diet of a plant nematode pest a dsRNA comprising:

a) a sense nucleotide sequence comprising a fragment of at least 21 contiguous nucleotides of a nucleic acid sequence of SEQ ID NO:1298, SEQ ID NO:1521, SEQ ID NO:1920 or SEQ ID NO:1925; and b) a sequence complementary to said sense nucleotide sequence, wherein uptake of the dsRNA by the plant nematode pest inhibits a biological function of Top-1 within said plant nematode pest, wherein said nematode is *Heterodera glycines*.

4. The method of claim 3, wherein said diet comprises a plant cell transformed to express said dsRNA.

5. The method of claim 1, wherein the double stranded ribonucleotide sequence comprises at least 21 contiguous nucleotides of SEQ ID NO:1298.

6. The method of claim 1, wherein the double stranded ribonucleotide sequence comprises at least 21 contiguous nucleotides of SEQ ID NO: 1521.

7. The method of claim 1, wherein the double stranded ribonucleotide sequence comprises at least 21 contiguous nucleotides of SEQ ID NO: 1920.

8. The method of claim 1, wherein the double stranded ribonucleotide sequence comprises at least 21 contiguous nucleotides of SEQ ID NO: 1925.

9. The method of claim 2, wherein the first polynucleotide sequence comprises at least 21 contiguous nucleotides of SEQ ID NO:1298.

10. The method of claim 2, wherein the first polynucleotide sequence comprises at least 21 contiguous nucleotides of SEQ ID NO:1521.

11. The method of claim 2, wherein the first polynucleotide sequence comprises at least 21 contiguous nucleotides of SEQ ID NO:1920.

12. The method of claim 2, wherein the first polynucleotide sequence comprises at least 21 contiguous nucleotides of SEQ ID NO:1925.

13. The method of claim 3, wherein the sense nucleotide sequence comprises at least 21 contiguous nucleotides of SEQ ID NO:1298.

14. The method of claim 3, wherein the sense nucleotide sequence comprises at least 21 contiguous nucleotides of SEQ ID NO:1521.

15. The method of claim 3, wherein the sense nucleotide sequence comprises at least 21 contiguous nucleotides of SEQ ID NO:1920.

16. The method of claim 3, wherein the sense nucleotide sequence comprises at least 21 contiguous nucleotides of SEQ ID NO:1925.

* * * * *